United States Patent
Rabuka et al.

(10) Patent No.: US 9,951,367 B2
(45) Date of Patent: Apr. 24, 2018

(54) ACTIVATED FORMYLGLYCINE-GENERATING ENZYMES AND METHODS OF PRODUCING AND USING THE SAME

(71) Applicant: R.P. Scherer Technologies, LLC, Carson City, NV (US)

(72) Inventors: David Rabuka, Kensington, CA (US); Gregory W. deHart, El Cerrito, CA (US); Patrick Holder, Oakland, CA (US); Jeanne Baker, Redwood City, CA (US)

(73) Assignee: R.P. Scherer Technologies, LLC, Carson City, NV (US)

( * ) Notice: Subject to any disclaimer, the term of this patent is extended or adjusted under 35 U.S.C. 154(b) by 59 days.

(21) Appl. No.: 14/975,403

(22) Filed: Dec. 18, 2015

(65) Prior Publication Data

US 2016/0230205 A1    Aug. 11, 2016

Related U.S. Application Data

(60) Provisional application No. 62/112,422, filed on Feb. 5, 2015, provisional application No. 62/134,461, filed on Mar. 17, 2015.

(51) Int. Cl.
| | |
|---|---|
| *C07K 19/00* | (2006.01) |
| *C07K 16/00* | (2006.01) |
| *A61K 38/00* | (2006.01) |
| *C12N 9/02* | (2006.01) |
| *C12P 21/00* | (2006.01) |
| *C07K 16/32* | (2006.01) |
| *A61K 47/68* | (2017.01) |

(52) U.S. Cl.
CPC ............ *C12P 21/005* (2013.01); *A61K 47/68* (2017.08); *C07K 16/00* (2013.01); *C07K 16/32* (2013.01); *C12N 9/0051* (2013.01); *C07K 2317/14* (2013.01); *C07K 2317/40* (2013.01); *C12Y 108/99* (2013.01)

(58) Field of Classification Search
CPC ........ A61K 38/00; A61K 38/17; A61K 38/43; A61K 39/00; C07K 16/00; C07K 19/00
See application file for complete search history.

(56) References Cited

U.S. PATENT DOCUMENTS

| | | |
|---|---|---|
| 2008/0187956 A1 | 8/2008 | Carrico et al. |
| 2011/0117621 A1 | 5/2011 | Rush et al. |
| 2013/0028881 A1 | 1/2013 | Von Figura et al. |
| 2014/0004097 A1 | 1/2014 | Zhang et al. |

FOREIGN PATENT DOCUMENTS

| | | |
|---|---|---|
| WO | WO 2004072275 | 8/2004 |
| WO | WO 2010081110 | 7/2010 |

OTHER PUBLICATIONS

DMEM/F-12 product sheet from ThermoFisher Scientific [Found online Jul. 5, 2016] at https:www.thermofisher.com/order/catalog/product/11320033> 3 pages.
Holder, et al. (2015) "Reconstitution of formylglycine-generating enzyme with copper (II) for aldehyde tag coversion" J. Biol. Chem. 290(25): 15730-15740.
Mariappan, et al. (2008) "The Non-catalytic N-terminal Extension of Formykglycine-generating Enzyme is Required for its Biologicla Activity and Retention in the Endoplasmic Reticulum." J. Biol. Chem. 283(17): 11556-11564.
PCT/US2015/066878 International Search Report & Written Opinion dated Jun. 3, 2016, 19 pages.
Cosma, et al., (2003) "The Multiple Sulfatase Deficiency Gene Encodes an Essential and Limiting Factor for the Activity of Sulfatases" Cell 113(4):445-456.
Dierks, et al., (1997) "Conversion of Cysteine to Formylglycine: A Protein Modification in the Endoplasmic Reticulum" Proc Natl Acad Sci USA, 94(22):11963-11968.
Dierks, et al., (1998) "Conversion of Cysteine to Formylglycine in Eukaryotic Sulfatases Occurs by a Common Mechanism in the Endoplasmic Reticulum" FEBS Lett. 423(1):61-65.
Dierks, et al., (2003) "Multiple Sulfatase Deficiency is Caused by Mutations in the Gene Encoding the Human Cα-Formylglycine Generating Enzyme" Cell 113(4):435-444.
Dierks, et al., (2005) "Molecular Basis for Multiple Sulfatase Deficiency and Mechanism for Formylglycine Generation of the Human Formylglycine-Generating Enzyme" Cell 121(4):541-552.
Fang, et al., (2004) "Post-Translational Formylglycine Modification of Bacterial Sulfatases by the Radical S-Adenosylmethionine Protein AtsB" J Biol Chem. 279(15):14570-8 [Epub Jan. 2, 2004].
Landgrebe, et al., (2003) "The Human SUMF1 Gene, Required for Posttranslational Sulfatase Modification, Defines a New Gene Family Which is Conserved from Pro- to Eukaryotes" Gene 316:47-56.
Prescher, et al., (2005) "Chemistry in Living Systems" Nat. Chem. Biol. 1(1):13-21.
Preusser, et al., (2005) "Molecular Characterization of the Human Cα-formylglycine-generating Enzyme" J. Biol. Chem. 280(15):14900-14910.
Rabuka, et al., (2012) "Site-specific chemical protein conjugation using genetically encoded aldehyde tags" Nature Protocols 7:1052-1067.
Roeser, et al., (2006) "A General Binding Mechanism for All Human Sulfatases by the Formylglycine-Generating Enzyme" Proc Natl Acad Sci USA 103(1):81-86.
Szameit, et al., (1999) "The Iron Sulfur Protein AtsB is Required for Posttranslational Formation of Formylglycine in the Klebsiella Sulfatase" J Biol Chem 274(22):15375-15381.

*Primary Examiner* — Maryam Monshipouri
(74) *Attorney, Agent, or Firm* — Rudy J. Ng; Brian E. Davy; Bozicevic, Field & Francis LLP

(57) ABSTRACT

The present disclosure provides activated formylglycine-generating enzymes (FGE), methods of producing activated FGE, and their use in methods of producing a protein comprising a formylglycine (FGly) residue. The methods of producing activated FGE, as well as methods of use of activated FGE in producing FGly-containing proteins, include both cell-based and cell-free methods. Compositions and kits that find use, e.g., in practicing the methods of the present disclosure are also provided.

16 Claims, 23 Drawing Sheets

A

B

FIG. 7, continued
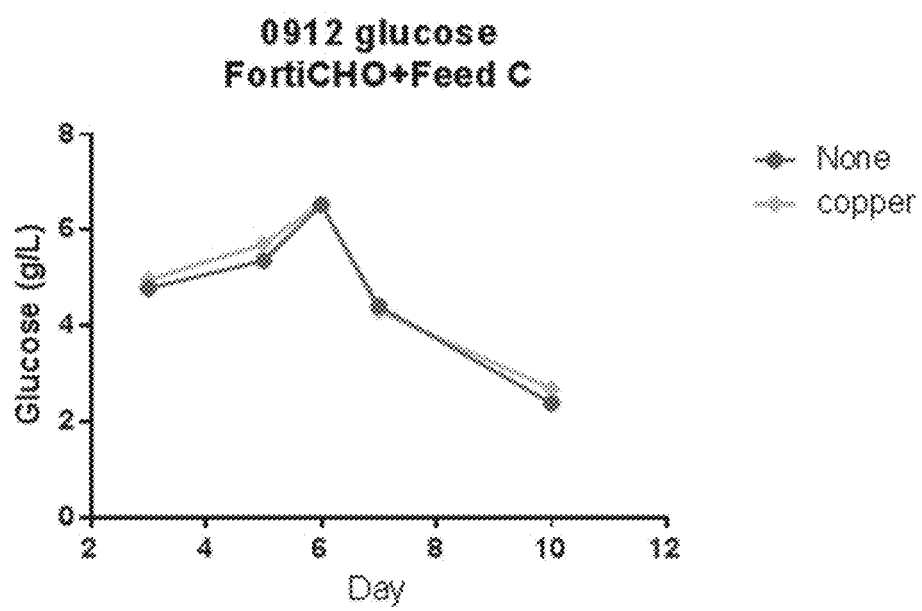

FIG. 15, continued
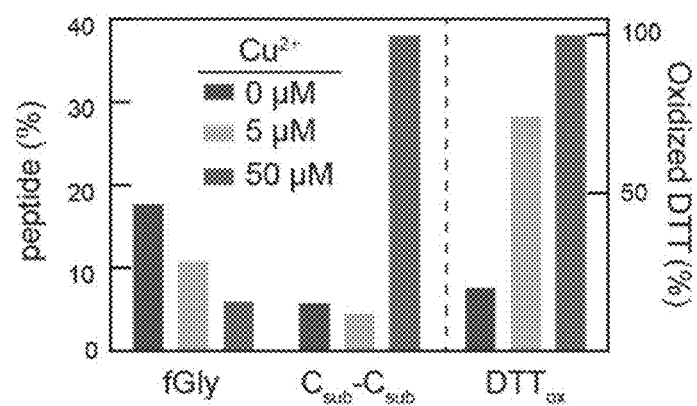

SEQUENCE LISTING

```
<160> NUMBER OF SEQ ID NOS: 12

<210> SEQ ID NO 1
<211> LENGTH: 374
<212> TYPE: PRT
<213> ORGANISM: Homo sapiens

<400> SEQUENCE: 1

Met Ala Ala Pro Ala Leu Gly Leu Val Cys Gly Arg Cys Pro Glu Leu
1               5                   10                  15

Gly Leu Val Leu Leu Leu Leu Leu Ser Leu Leu Cys Gly Ala Ala
            20                  25                  30

Gly Ser Gln Glu Ala Gly Thr Gly Ala Gly Ala Gly Ser Leu Ala Gly
        35                  40                  45

Ser Cys Gly Cys Gly Thr Pro Gln Arg Pro Gly Ala His Gly Ser Ser
    50                  55                  60

Ala Ala Ala His Arg Tyr Ser Arg Glu Ala Asn Ala Pro Gly Pro Val
65                  70                  75                  80

Pro Gly Glu Arg Gln Leu Ala His Ser Lys Met Val Pro Ile Pro Ala
                85                  90                  95

Gly Val Phe Thr Met Gly Thr Asp Asp Pro Gln Ile Lys Gln Asp Gly
            100                 105                 110

Glu Ala Pro Ala Arg Arg Val Thr Ile Asp Ala Phe Tyr Met Asp Ala
        115                 120                 125

Tyr Glu Val Ser Asn Thr Glu Phe Glu Lys Phe Val Asn Ser Thr Gly
    130                 135                 140
```

-continued

```
Tyr Leu Thr Glu Ala Glu Lys Phe Gly Asp Ser Phe Val Phe Glu Gly
145                 150                 155                 160

Met Leu Ser Glu Gln Val Lys Thr Asn Ile Gln Gln Ala Val Ala Ala
                165                 170                 175

Ala Pro Trp Trp Leu Pro Val Lys Gly Ala Asn Trp Arg His Pro Glu
            180                 185                 190

Gly Pro Asp Ser Thr Ile Leu His Arg Pro Asp His Pro Val Leu His
        195                 200                 205

Val Ser Trp Asn Asp Ala Val Ala Tyr Cys Thr Trp Ala Gly Lys Arg
    210                 215                 220

Leu Pro Thr Glu Ala Glu Trp Glu Tyr Ser Cys Arg Gly Gly Leu His
225                 230                 235                 240

Asn Arg Leu Phe Pro Trp Gly Asn Lys Leu Gln Pro Lys Gly Gln His
                245                 250                 255

Tyr Ala Asn Ile Trp Gln Gly Glu Phe Pro Val Thr Asn Thr Gly Glu
            260                 265                 270

Asp Gly Phe Gln Gly Thr Ala Pro Val Asp Ala Phe Pro Pro Asn Gly
        275                 280                 285

Tyr Gly Leu Tyr Asn Ile Val Gly Asn Ala Trp Glu Trp Thr Ser Asp
    290                 295                 300

Trp Trp Thr Val His His Ser Val Glu Glu Thr Leu Asn Pro Lys Gly
305                 310                 315                 320

Pro Pro Ser Gly Lys Asp Arg Val Lys Lys Gly Gly Ser Tyr Met Cys
                325                 330                 335

His Arg Ser Tyr Cys Tyr Arg Tyr Arg Cys Ala Ala Arg Ser Gln Asn
            340                 345                 350

Thr Pro Asp Ser Ser Ala Ser Asn Leu Gly Phe Arg Cys Ala Ala Asp
        355                 360                 365

Arg Leu Pro Thr Met Asp
    370

<210> SEQ ID NO 2
<211> LENGTH: 302
<212> TYPE: PRT
<213> ORGANISM: Artificial Sequence
<220> FEATURE:
<223> OTHER INFORMATION: Synthetic polypeptide

<400> SEQUENCE: 2

Glu Ala Asn Ala Pro Gly Pro Val Pro Gly Glu Arg Gln Leu Ala His
1               5                   10                  15

Ser Lys Met Val Pro Ile Pro Ala Gly Val Phe Thr Met Gly Thr Asp
                20                  25                  30

Asp Pro Gln Ile Lys Gln Asp Gly Glu Ala Pro Ala Arg Arg Val Thr
            35                  40                  45

Ile Asp Ala Phe Tyr Met Asp Ala Tyr Glu Val Ser Asn Thr Glu Phe
        50                  55                  60

Glu Lys Phe Val Asn Ser Thr Gly Tyr Leu Thr Ala Glu Lys Phe
65              70                  75                  80

Gly Asp Ser Phe Val Phe Glu Gly Met Leu Ser Glu Gln Val Lys Thr
                85                  90                  95

Asn Ile Gln Gln Ala Val Ala Ala Ala Pro Trp Trp Leu Pro Val Lys
            100                 105                 110

Gly Ala Asn Trp Arg His Pro Glu Gly Pro Asp Ser Thr Ile Leu His
        115                 120                 125
```

```
Arg Pro Asp His Pro Val Leu His Val Ser Trp Asn Asp Ala Val Ala
    130                 135                 140

Tyr Cys Thr Trp Ala Gly Lys Arg Leu Pro Thr Glu Ala Glu Trp Glu
145                 150                 155                 160

Tyr Ser Cys Arg Gly Gly Leu His Asn Arg Leu Phe Pro Trp Gly Asn
                165                 170                 175

Lys Leu Gln Pro Lys Gly Gln His Tyr Ala Asn Ile Trp Gln Gly Glu
            180                 185                 190

Phe Pro Val Thr Asn Thr Gly Glu Asp Gly Phe Gln Gly Thr Ala Pro
        195                 200                 205

Val Asp Ala Phe Pro Pro Asn Gly Tyr Gly Leu Tyr Asn Ile Val Gly
    210                 215                 220

Asn Ala Trp Glu Trp Thr Ser Asp Trp Trp Thr Val His His Ser Val
225                 230                 235                 240

Glu Glu Thr Leu Asn Pro Lys Gly Pro Pro Ser Gly Lys Asp Arg Val
                245                 250                 255

Lys Lys Gly Gly Ser Tyr Met Cys His Arg Ser Tyr Cys Tyr Arg Tyr
            260                 265                 270

Arg Cys Ala Ala Arg Ser Gln Asn Thr Pro Asp Ser Ser Ala Ser Asn
        275                 280                 285

Leu Gly Phe Arg Cys Ala Ala Asp Arg Leu Pro Thr Met Asp
    290                 295                 300

<210> SEQ ID NO 3
<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Xaa at position 2 is Cys or Ser

<400> SEQUENCE: 3

Leu Xaa Thr Pro Ser Arg
1               5

<210> SEQ ID NO 4
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 4

Leu Cys Thr Pro Ser Arg
1               5

<210> SEQ ID NO 5
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 5

Leu Ser Thr Pro Ser Arg
1               5

<210> SEQ ID NO 6
```

```
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 6

Asp Arg Ser Leu
1

<210> SEQ ID NO 7
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 7

Lys Asp Glu Leu
1

<210> SEQ ID NO 8
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 8

Ala Leu Cys Thr Pro Ser Arg Gly Ser Leu Phe Thr Gly Arg
1               5                   10

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 9
gaggctaacg ctccgggccc                                           20

<210> SEQ ID NO 10
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 10
gtccatagtg ggcaggcggt c                                         21

<210> SEQ ID NO 11
<211> LENGTH: 296
<212> TYPE: PRT
<213> ORGANISM: Artificial sequence
<220> FEATURE:
<223> OTHER INFORMATION: Synthetic polypeptide

<400> SEQUENCE: 11

Asp Arg Ser Leu Glu Ala Asn Ala Pro Gly Pro Val Pro Gly Glu Arg
1               5                   10                  15

Gln Leu Ala His Ser Lys Met Val Pro Ile Pro Ala Gly Val Phe Thr
                20                  25                  30

Met Gly Thr Asp Asp Pro Gln Ile Lys Gln Asp Gly Glu Ala Pro Ala
            35                  40                  45
```

```
Arg Arg Val Thr Ile Asp Ala Phe Tyr Met Asp Ala Tyr Glu Val Ser
    50              55                  60
Asn Thr Glu Phe Glu Lys Phe Val Asn Ser Thr Gly Tyr Leu Thr Glu
65              70                  75                  80
Val Ala Ala Ala Pro Trp Trp Leu Pro Val Lys Gly Ala Asn Trp Arg
                85                  90                  95
His Pro Glu Gly Pro Asp Ser Thr Ile Leu His Arg Pro Asp His Pro
            100                 105                 110
Val Leu His Val Ser Trp Asn Asp Ala Val Ala Tyr Cys Thr Trp Ala
        115                 120                 125
Gly Lys Arg Leu Pro Thr Glu Ala Glu Trp Glu Tyr Ser Cys Arg Gly
    130                 135                 140
Gly Leu His Asn Arg Leu Phe Pro Trp Gly Asn Lys Leu Gln Pro Lys
145                 150                 155                 160
Gly Gln His Tyr Ala Asn Ile Trp Gln Gly Glu Phe Pro Val Thr Asn
            165                 170                 175
Thr Gly Glu Asp Gly Phe Gln Gly Thr Ala Pro Val Asp Ala Phe Pro
            180                 185                 190
Pro Asn Gly Tyr Gly Leu Tyr Asn Ile Val Gly Asn Ala Trp Glu Trp
            195                 200                 205
Thr Ser Asp Trp Trp Thr Val His His Ser Val Glu Glu Thr Leu Asn
        210                 215                 220
Pro Lys Gly Pro Pro Ser Gly Lys Asp Arg Val Lys Lys Gly Gly Ser
225                 230                 235                 240
Tyr Met Cys His Arg Ser Tyr Cys Tyr Arg Tyr Arg Cys Ala Ala Arg
                245                 250                 255
Ser Gln Asn Thr Pro Asp Ser Ser Ala Ser Asn Leu Gly Phe Arg Cys
            260                 265                 270
Ala Ala Asp Arg Leu Pro Thr Met Asp Lys Gly Glu Asn Leu Tyr Phe
        275                 280                 285
Gln Gly His His His His His His
    290                 295

<210> SEQ ID NO 12
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 12

Ser Leu Cys Thr Pro Ser Arg Gly Ser
1               5
```

ACTIVATED FORMYLGLYCINE-GENERATING ENZYMES AND METHODS OF PRODUCING AND USING THE SAME

CROSS-REFERENCE TO RELATED APPLICATIONS

This application claims the benefit of U.S. Provisional Patent Application No. 62/112,422, filed Feb. 5, 2015, and U.S. Provisional Patent Application No. 62/134,461, filed Mar. 17, 2015, which applications are incorporated herein by reference in their entireties.

INTRODUCTION

The properties of therapeutic proteins can be enhanced by site-specific protein conjugation. Recombinant proteins expressed in mammalian cells can be site-specifically modified via one or more genetically encoded aldehyde groups. For example, a peptide sequence recognized by the endoplasmic reticulum (ER)-resident formylglycine generating enzyme (FGE), which can be as short as 5 residues, may be genetically encoded into heterologous proteins expressed in mammalian cells. FGE co-translationally converts a cysteine or serine residue of the FGE recognition site to a formylglycine residue, thereby producing proteins bearing a unique aldehyde group. This aldehyde group may be utilized for site-specific conjugation of an agent of interest (e.g., a therapeutic agent, an imaging agent, etc.) to the protein.

SUMMARY

The present disclosure provides activated formylglycine-generating enzymes (FGE), methods of producing activated FGE, and their use in methods of producing a protein comprising a formylglycine (FGly) residue. The methods of producing activated FGE, as well as methods of use of activated FGE in producing FGly-containing proteins, include both cell-based and cell-free methods, Compositions and kits that find use, e.g., in practicing the methods of the present disclosure are also provided.

Aspects of the present disclosure include a method of producing a protein comprising a formylglycine residue. The method includes combining an activated formylglycine-generating enzyme (FGE) with a protein comprising an FGE recognition site under conditions in which the activated FGE converts a cysteine residue or a serine residue of the FGE recognition site to a formylglycine residue, to produce a protein comprising a formylglycine residue.

In some embodiments, the combining includes culturing a cell that includes a formylglycine-generating enzyme (FGE), and the protein having the FGE recognition site, in a cell culture medium comprising $Cu^{2+}$ under cell culture conditions in which the FGE converts the cysteine residue or the serine residue of the FGE recognition site to the formylglycine residue.

In some embodiments, the $Cu^{2+}$ is present in the cell culture medium at a concentration of from 1 nM to 10 mM.

In some embodiments, the $Cu^{2+}$ is present in the cell culture medium at a concentration of from 1 μM to 1 mM.

In some embodiments in which the method of producing a protein comprising a formylglycine residue involve a cell, the FGE is endogenous to the cell and/or the cell is genetically modified to express an FGE, and the protein containing an FGE recognition site is endogenous to the cell and/or the cell is genetically modified to express the protein containing an FGE recognition site. Either or both of the FGE and the protein containing an FGE recognition site may be endogenous to the cell, or the cell may be genetically modified to express either or both of the FGE and the protein containing an FGE recognition site. Where the cell is genetically modified to express an FGE, the cell may also express an FGE endogenous to the cell.

In some embodiments, the cell is a eukaryotic cell.

In some embodiments, the eukaryotic cell is a mammalian cell.

In some embodiments, the mammalian cell is selected from: a CHO cell, a HEK cell, a BHK cell, a COS cell, a Vero cell, a Hela cell, an NIH 3T3 cell, a Huh-7 cell, a PC12 cell, a RAT1 cell, a mouse L cell, an HLHepG2 cell, an NSO cell, a C127 cell, a hybridoma cell, a PerC6 cell, a CAP cell, and a Sp-2/0 cell.

In some embodiments, the mammalian cell is a human cell.

In some embodiments, the eukaryotic cell is a yeast cell.

In some embodiments, the eukaryotic cell is an insect cell.

In some embodiments, the combining includes expressing an FGE and the protein comprising the FGE recognition site in a cell-free reaction mixture that includes $Cu^{2+}$ under conditions in which the FGE converts the cysteine residue or the serine residue of the FGE recognition site to the formylglycine residue.

In some embodiments, the activated FGE and the protein having the FGE recognition site are combined in a reaction mixture that includes a reducing agent. In some embodiments, the reducing agent promotes conversion of the cysteine residue or the serine residue of the FGE recognition site to the formylglycine residue. In some embodiments, the reducing agent is 2-mercaptoethanol.

In some embodiments, the activated FGE and the protein having the FGE recognition site are combined in a cell-free reaction mixture.

In some embodiments, prior to combining the activated FGE with the protein having the FGE recognition site, the method includes activating an FGE with $Cu^{2+}$.

In some embodiments, elemental oxygen is present as a terminal oxidant.

In some embodiments, the elemental oxygen is provided by oxygen, a mixture of oxygen and hydrogen sulfide, or oxygen under basic conditions.

In some embodiments, the elemental oxygen is a terminal oxidant in a reaction catalyzed by $Cu^{2+}$.

In some embodiments, the $Cu^{2+}$ is provided by a source of $Cu^{2+}$ selected from copper sulfate, copper citrate, copper tartrate, Fehling's reagent, and Benedict's reagent.

In some embodiments, the source of $Cu^{2+}$ is copper sulfate.

In some embodiments, when the activated FGE and the protein having the FGE recognition site are combined in a cell-free reaction mixture, the activated FGE is an N-terminally truncated FGE. The N-terminally truncated FGE may be an N-terminally truncated human FGE.

In some embodiments, the protein is an antibody or antibody fragment.

In some embodiments, the antibody or antibody fragment is selected from: an IgG or fragment thereof, a Fab, a F(ab')2, a Fab', an Fv, an ScFv, a bispecific antibody or fragment thereof, a diabody or fragment thereof, a chimeric antibody or fragment thereof, a monoclonal antibody or fragment thereof, a humanized antibody or fragment thereof, and a fully human antibody or fragment thereof.

In some embodiments, the antibody specifically binds to a tumor-associated antigen or a tumor-specific antigen.

In some embodiments, the tumor associated antigen or tumor-specific antigen is selected from: HER2, CD19, CD22, CD30, CD33, CD56, CD66/CEACAM5, CD70, CD74, CD79b, CD138, Nectin-4, Mesothelin, Transmembrane glycoprotein NMB (GPNMB), Prostate-Specific Membrane Antigen (PSMA), SLC44A4, CA6, and CA-IX.

In some embodiments, the protein is a ligand.

In some embodiments, the ligand is a growth factor.

In some embodiments, the ligand is a hormone.

In some embodiments, the method further includes conjugating an agent to the protein having the formylglycine residue via an aldehyde moiety of the formylglycine residue.

In some embodiments, the agent is a therapeutic agent.

In some embodiments, the therapeutic agent is selected from: a cytotoxic agent, an antiproliferative agent, an antineoplastic agent, an antibiotic agent, an antifungal agent, and an antiviral agent.

In some embodiments, the agent is an imaging agent.

In some embodiments, the imaging agent is selected from: a fluorescent dye, a near-infrared (NIR) imaging agent, and a single-photon emission computed tomography (SPECT)/CT imaging agent, a nuclear magnetic resonance (NMR) imaging agent, a magnetic resonance imaging (MRI) agent, a positron-emission tomography (PET) agent, an x-ray imaging agent, a computed tomography (CT) imaging agent, a K-edge imaging agent, an ultrasound imaging agent, a photoacoustic imaging agent, an acoustic optical imaging agent, microwave imaging agent, a nuclear imaging agent, and combinations thereof.

Aspects of the present disclosure include a composition that includes a cell culture medium that includes $Cu^{2+}$, and a cell present in the cell culture medium, where the cell expresses formylglycine-generating enzyme (FGE).

In some embodiments, the $Cu^{2+}$ is present in the cell culture medium at a concentration of from 0.1 μM to 10 mM.

In some embodiments, the $Cu^{2+}$ is present in the cell culture medium at a concentration of from 1 μM to 1 mM.

In some embodiments in which the composition includes a cell, the FGE is endogenous to the cell and/or the cell is genetically modified to express an FGE, and the protein containing an FGE recognition site is endogenous to the cell and/or the cell is genetically modified to express the protein containing an FGE recognition site. Either of both of the FGE and the protein containing an FGE recognition site may be endogenous to the cell, or the cell may be genetically modified to express either or both of the FGE and the protein containing an FGE recognition site. Where the cell is genetically modified to express an FGE, the cell may also express an FGE endogenous to the cell.

In some embodiments, the cell is a eukaryotic cell.

In some embodiments, the eukaryotic cell is a mammalian cell.

In some embodiments, the mammalian cell is selected from: a CHO cell, a HEK cell, a BHK cell, a COS cell, a Vero cell, a Hela cell, an NIH 3T3 cell, a Huh-7 cell, a PC12 cell, a RAT1 cell, a mouse L cell, an HLHepG2 cell, an NSO cell, a C127 cell, a hybridoma cell, a PerC6 cell, a CAP cell, and a Sp-2/0 cell.

In some embodiments, the eukaryotic cell is a yeast cell.

In some embodiments, the eukaryotic cell is an insect cell.

In some embodiments, the cell is a prokaryotic cell.

Aspects of the present disclosure include a method that includes culturing a cell that includes a nucleic acid encoding a formylglycine-generating enzyme (FGE) in a cell culture medium that has $Cu^{2+}$, where the culturing is under conditions in which the FGE is expressed in the cell.

In some embodiments, the $Cu^{2+}$ is present in the cell culture medium at a concentration of from 0.1 μM to 10 mM.

In some embodiments, the $Cu^{2+}$ is present in the cell culture medium at a concentration of from 1 μM to 1 mM.

In some embodiments, the cell is a eukaryotic cell.

In some embodiments, the eukaryotic cell is a mammalian cell.

In some embodiments, the mammalian cell is selected from: a CHO cell, a HEK cell, a BHK cell, a COS cell, a Vero cell, a Hela cell, an NIH 3T3 cell, a Huh-7 cell, a PC12 cell, a RAT1 cell, a mouse L cell, an HLHepG2 cell, an NSO cell, a C127 cell, a hybridoma cell, a PerC6 cell, a CAP cell, and a Sp-2/0 cell.

In some embodiments, the eukaryotic cell is a yeast cell.

In some embodiments, the eukaryotic cell is an insect cell.

In some embodiments, the cell is a prokaryotic cell.

Aspects of the present disclosure include a method of producing an activated formylglycine-generating enzyme (FGE), where the method includes treating an FGE with $Cu^{2+}$ to produce an activated FGE.

In some embodiments, treating the FGE with $Cu^{2+}$ includes culturing a cell that has a nucleic acid encoding the FGE in a cell culture medium that has $Cu^{2+}$, where the culturing is under conditions in which the FGE is expressed in the cell.

In some embodiments, the $Cu^{2+}$ is present in the cell culture medium at a concentration of from 0.1 μM to 10 mM.

In some embodiments, the $Cu^{2+}$ is present in the cell culture medium at a concentration of from 1 μM to 1 mM.

In some embodiments, the cell is a eukaryotic cell.

In some embodiments, the eukaryotic cell is a mammalian cell.

In some embodiments, the mammalian cell is selected from: a CHO cell, a HEK cell, a BHK cell, a COS cell, a Vero cell, a Hela cell, an NIH 3T3 cell, a Huh-7 cell, a PC12 cell, a RAT1 cell, a mouse L cell, an HLHepG2 cell, an NSO cell, a C127 cell, a hybridoma cell, a PerC6 cell, a CAP cell, and a Sp-2/0 cell.

In some embodiments, the eukaryotic cell is a yeast cell.

In some embodiments, the eukaryotic cell is an insect cell.

In some embodiments, the cell is a prokaryotic cell.

In some embodiments, the method further includes purifying the FGE from the cell.

In some embodiments, treating the FGE includes expressing the FGE in a cell-free reaction mixture comprising $Cu^{2+}$.

In some embodiments, the FGE is treated with $Cu^{2+}$ in a cell-free reaction mixture.

In some embodiments, elemental oxygen is present as a terminal oxidant.

In some embodiments, the elemental oxygen is provided by oxygen, a mixture of oxygen and hydrogen sulfide, or oxygen under basic conditions.

In some embodiments, the elemental oxygen is a terminal oxidant in a reaction catalyzed by $Cu^{2+}$.

In some embodiments, the $Cu^{2+}$ is provided by a source of $Cu^{2+}$ selected from: copper sulfate, copper citrate, copper tartrate, Fehling's reagent, and Benedict's reagent.

In some embodiments, the method further includes purifying the FGE from the $Cu^{2+}$.

In some embodiments, when the FGE is treated with $Cu^{2+}$ in a cell-free reaction mixture, the FGE is an N-terminally truncated FGE. In some embodiments, the FGE is an N-terminally truncated human FGE.

Aspects of the present disclosure include an activated formylglycine-generating enzyme (FGE) produced by the method disclosed herein.

Aspects of the present disclosure include a cell-free composition that includes an activated formylglycine-generating enzyme (FGE), and a buffer. In some embodiments, the activated FGE included in the cell-free composition is an N-terminally truncated FGE (e.g., an N-terminally truncated human FGE).

In some embodiments, the composition includes a protein having an FGE recognition site.

Aspects of the present disclosure include a kit. The kit includes an activated formylglycine-generating enzyme (FGE), and instructions for using the activated FGE to convert a cysteine residue or a serine residue present in an FGE recognition site of a protein to a formylglycine residue. In some embodiments, the activated FGE included in the kit is an N-terminally truncated FGE (e.g., an N-terminally truncated human FGE).

Aspects of the present disclosure include a kit that includes a nucleic acid that encodes a formylglycine-generating enzyme (FGE), and $Cu^{2+}$ or a source of $Cu^{2+}$.

In some embodiments, the kit also includes cells suitable for expressing the FGE encoded by the nucleic acid. Such cells may express an endogenous FGE and/or express an endogenous protein containing an FGE recognition site.

BRIEF DESCRIPTION OF THE FIGURES

FIG. 3, Panel B shows data comparing the protein titer of $Cu^{2+}$-treated cells and untreated cells. FIG. 3, Panel C provides data showing in vivo FGE activation/increased conversion in $Cu^{2+}$-treated cells according to an embodiment of the present disclosure.

FIG. 7, Panel B shows a graph of lactate consumption in the presence or absence of $Cu^{2+}$. FIG. 7, Panel C shows a graph of glucose consumption in the presence or absence of $Cu^{2+}$.

FIG. 10, panel a, Lanes show intermediate stages of purification of Sc-FGE as follows: 1—total soluble protein after cell lysis; 2—total soluble protein after DNA precipitation with 1% w/v streptomycin sulfate; 3—soluble protein in the flow-through recovered from loading the lysate on Ni-NTA resin; 4—soluble protein in the wash fractions of Ni-NTA chromatography; and 5—soluble protein in the elution fractions of Ni-NTA chromatography. FIG. 10, panel b, shows the final purity of 10 production batches of Hs-cFGE expressed in Hi5 cells.

FIG. 11 shows LC/MS characterization of starting material and product peptides. Shown are spectra of the peaks with retention t=2.1 min (FIG. 11, panel a), and t=3.3 min (FIG. 11, panel b) from FIG. 14, panel a.

FIG. 12, panel a, shows a graph indicating that the identity of the $C_{sub}$-$C_{sub}$ dimer was confirmed by LC-MS of a side product peak that formed during in vitro conversion with FGE. FIG. 12, panel b, shows a graph indicating that addition of hydrogen peroxide to FGE reaction mixtures rapidly formed substrate dimer and inhibited product formation. FIG. 12, panel c, shows a graph indicating that product formation was also inhibited by the presence of $Cu^{2+}$ in reaction mixtures. This inhibition was a result of consuming DTT (FIG. 12, panel d) and trapping substrate by dimerization (FIG. 12, panel e).

FIG. 13, panel a, shows LC/MS identification of Csub-BME. FIG. 13, panel b, shows an expanded HPLC trace of an FGE reaction mixture containing BME as the stoichiometric reductant. Product formation catalyzed by FGE, in the absence of reducing agent (FIG. 13, panel c), with 2.5 mol equiv of reducing agent (FIG. 13, panel d) and, with 100 mol equiv of reducing agent (FIG. 13, panel e).

FIG. 14, panel a, shows data where a 14-amino acid peptide substrate was used to measure the kinetics of FGE catalysis. The Cys- and fGly-containing peptides were separated by RP-HPLC, and their quantities were determined by integrating the peak areas at 215 nm. The asterisk indicates an impurity formed during peptide synthesis. FIG. 14, panel b, shows data indicating that the initial velocity of the reaction ($v_0$) was determined by extrapolating a plot of the instantaneous reaction velocity (p/t) versus time (t) to the y-axis (t=0). FIG. 14, panel c, shows a schematic indicating that wild-type Hs-FGE contains three primary domains: an ER-directing signal sequence, an N-terminal extension that interacts with ERp44 for ER retention, and a catalytic core. FIG. 14, panel d, shows a graph showing the specific activity of eukaryotic and prokaryotic FGEs as purified from cell culture. Full length (Hs-FGE) and the core lacking the NTE (Hs-cFGE) had similar specific activities. Despite high sequence and structural homology with Hs-cFGE, the prokaryotic Sc-FGE as produced in E. coli was less active than Hs-cFGE.

FIG. 15, panel a, shows a graph indicating that, as produced in E. coli, Sc-FGE had low specific activity. Treatment of Sc-FGE with two-electron oxidants or reductants (DHAA or DTT, respectively) did not change the activity of the enzyme. In contrast, treatment with an excess of $CuSO_4$ followed by gel filtration to remove the $Cu^{2+}$ significantly increased FGE activity. FIG. 15, panel b, shows a graph indicating that substoichiometric amounts of $Cu^{2+}$ did not fully activate Sc-FGE.

Addition of 1 or more molar equiv of $Cu^{2+}$ fully activated the enzyme. FIG. 15, panel c, shows a graph indicating that, as purified, Sc-FGE contained ~0.01 Cu/FGE, and Hs-cFGE contained 0.34 Cu/FGE. After activation in vitro, Sc-FGE and Hs-FGE contained 1.1 and 1.4 Cu/FGE, respectively. In all cases, the amount of copper contained in preparations of purified enzyme correlated with the specific activity of the enzyme. FIG. 15, panel d, shows formation of the oxidized form of DTT as well as $C_{sub}$-$C_{sub}$ as a result of copper-catalyzed disulfide formation.

FIG. 16, panel a, shows a schematic of Hs-cFGE, which contains two structural disulfides and two active site cysteines, which can form a disulfide in the apoenzyme. FIG. 16, panel b, shows a graph indicating that the redox state of $C_{341}$ can be measured by LC-MS/MS. After activation with $Cu^{2+}$, the amount of $C_{341}$ accessible to solution was ~28%. Upon treatment with reducing agent (DTT) the amount of accessible $C_{341}$ increased to 93%. However, the specific activity of the enzyme did not decrease. Treatment with DTT did not affect $C_{235}$-containing structural disulfide.

FIG. 17, panel a, shows a graph indicating that pretreatment of activated FGEs with EDTA or KCN resulted in little to no change in specific activity. Only Hs-cFGE activity decreased modestly after KCN treatment. FIG. 17, panel b, shows a graph indicating that both Sc-FGE and c, Hs-cFGE were inhibited during turnover in a concentration-dependent manner by $CN^-$ which was a strong ligand for copper. FIG. 17, panel d, shows pretreatment of activated Sc-FGE (n=6) with reductants (DTT, TCEP) or a metal chelator (EDTA) do not change the specific activity of the enzyme. When the reductant and chelator are combined (15 mM each, 1 h, 37° C.), the FGE activity is nearly eliminated.

FIG. 18, panel a, shows a Michaelis-Menten plot correlating substrate concentration with $v_0$ for Sc-FGE and for Hs-cFGE (FIG. 18, panel b). The data were fit to the Michaelis-Menten equation by nonlinear regression to determine the kinetic parameters (FIG. 18, panel c).

FIG. 19, panel a, shows a graph of product formation in FGE reaction mixtures across a range of 0-10 mM βME. Without βME, fGly and $C_{sub}$-$C_{sub}$ formed at comparable rates. As [βME] was increased, $C_{sub}$-$C_{sub}$ was replaced by $C_{sub}$-βME, and product formed at a higher rate. FIG. 19, panel b, shows a graph indicating that the initial velocity of FGE catalysis with βME was higher than with DTT. FIG. 19, panel c, shows a schematic indicating that these data confirm that formation of [E•S] resulted, i, in a disulfide between E and S. Catalysis ii, converted substrate to product, which was then released iii. In the presence of thiol reducing agents, the rate of catalysis defined by $k_{cat}$ was in competition with thiol-disulfide exchange iv, with rate constant $k_{DS}$, which dissociated the E•S complex and released $C_{sub}$-R. This species can then react with another equivalent of reducing agent v, to regenerate free substrate. When the reagent added was a strong non-thiol reductant (e.g. TCEP) or a thiol that can cyclize (DTT), iv and V collapsed to a single step. When the reducing agent was a monothiol, the $C_{sub}$-R can persist long enough to reform [E•S] with rate constant $k_{DS}$.

FIG. 20, panel a, shows a schematic indicating that the aldehyde tag was installed in three regions (hinge, $CH_2$, and $CH_3$) of the heavy chain of an IgG1 heavy chain. After reaction with FGE in vitro, the quantities of Cys and fGly were determined. Under optimized conditions, the yield of conversion from Cys to fGly was consistently 85-95%. FIG. 20, panel b, shows a graph indicating that the yield of biocatalytic fGly production was independent of reaction scale, as measured in 0.8, 8.0 and 80.0 mg test cases on two individual mAbs. FIG. 20, panel c, shows a graph of a representative example from a larger scale reaction. After conversion with FGE, the fGly content was 98.1%, corresponding to a conversion yield of 97.8%.

FIG. 21, panel a, shows a schematic indicating that a monoclonal antibody was disassembled and digested, and the Cys and fGly functional groups were trapped as the carboxyamidomethyl (CAM) and methyl oxime (MeOx) species, respectively, for characterization, through the following steps: i) DTT, 37° C., 15 min; ii) HCl, then $NH_4HCO_3$; iii) trypsin, iodoacetamide, pH 8, 37° C., 1 h; iv) methoxylamine, pH 5.5, 16 h FIG. 21, panel b, shows a graph indicating that each aldehyde tag location was characterized by a unique tryptic peptide containing the installed tag sequence. Here, a 9-mer peptide was generated by trypsin. Targeted MRM-MS was used to quantify the peptides modified as CAM or MeOx. The five most intense precursor/product ion transitions were chosen for peak area integration. FIG. 21, panel c shows an ion chromatogram of the CAM- and MeOx-containing peptides. The MeOx-containing peptide separated into the diastereomers present as a result of oxime formation.

FIG. 22, panel a, and FIG. 22, panel b, shows graphs of ELISA measurements of antibody/antigen affinity for two IgG1 mAbs. FIG. 22, panel c, shows a graph indicating that measurement of the proportion of oxidized methionine at position 252 in the $CH_3$ domain of an IgG1 scaffold was unchanged over the course of the reaction.

DETAILED DESCRIPTION

Figure 1:
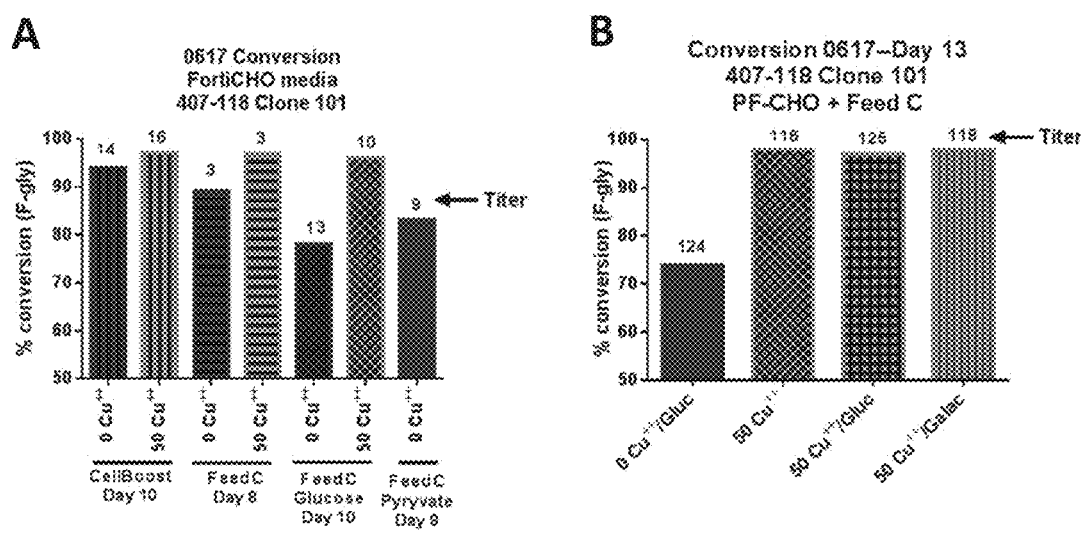
FIG. 1, Panels A-B provide data showing in vivo FGE activation/increased conversion in $Cu^{2+}$-treated cells according to certain embodiments of the present disclosure.

The present disclosure provides activated formylglycine-generating enzymes (FGE), methods of producing activated FGE, and their use in methods of producing a protein comprising a formylglycine (FGly) residue. The methods of producing activated FGE, as well as methods of use of activated FGE in producing FGly-containing proteins, include both cell-based and cell-free methods, Compositions and kits that find use, e.g., in practicing the methods of the present disclosure are also provided.

Before the methods and compositions of the present disclosure are described in greater detail, it is to be understood that the methods and compositions are not limited to particular embodiments described, as such may, of course, vary. It is also to be understood that the terminology used herein is for the purpose of describing particular embodiments only, and is not intended to be limiting, since the scope of the methods and compositions will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within by the methods and compositions. The upper and lower limits of these smaller ranges may independently be included in the smaller ranges and are also encompassed within by the methods and compositions, subject to any specifically excluded limit in the stated range. Where the stated range includes one or both of the limits, ranges excluding either or both of those included limits are also included in the methods and compositions.

Unless defined otherwise, all technical and scientific terms used herein have the same meaning as commonly understood by one of ordinary skill in the art to which the methods belong. Although any methods and compositions similar or equivalent to those described herein can also be used in the practice or testing of the methods and compositions, representative illustrative methods and compositions are now described.

Any publications and patents cited in this specification are herein incorporated by reference as if each individual publication or patent were specifically and individually indicated to be incorporated by reference and are incorporated herein by reference to disclose and describe the materials and/or methods and compositions in connection with which the publications are cited. The citation of any publication is for its disclosure prior to the filing date and should not be construed as an admission that the present methods and compositions are not entitled to antedate such publication, as the date of publication provided may be different from the actual publication date which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the methods and compositions, which are, for clarity, described in the context of separate embodiments, may also be provided in combination in a single embodiment. Conversely, various features of the methods and compositions, which are, for brevity, described in the context of a single embodiment, may also be provided separately or in any suitable sub-combination. All combinations of the embodiments are specifically embraced by the present disclosure and are disclosed herein just as if each and every combination was individually and explicitly disclosed, to the extent that such combinations embrace operable processes and/or devices. In addition, all sub-combinations listed in the embodiments describing such variables are also specifically embraced by the present methods and compositions and are disclosed herein just as if each and every such sub-combination was individually and explicitly disclosed herein.

As will be apparent to those of skill in the art upon reading this disclosure, each of the individual embodiments described and illustrated herein has discrete components and features which may be readily separated from or combined with the features of any of the other embodiments without departing from the scope or spirit of the present methods. Any recited method can be carried out in the order of events recited or in any other order that is logically possible.

Formylglycine-Generating Enzymes, FGE Recognition Sequences, and Target Proteins Aspects of the present disclosure include methods of making activated formylglycine-generating enzymes (FGEs), and methods of use of activated FGEs to produce formylglycine-containing proteins by conversion of an amino acid in an FGE recognition sequence in a protein of interest. Compositions that include activated FGEs and proteins of interest, which proteins include one or more FGE recognition sequences and/or one or more formylglycine residues, are also provided.

Described below are examples of FGEs that may be activated for use in the methods and compositions of the present disclosure, examples of FGE recognition sequences that may be provided in a protein of interest, and examples of proteins of interest which may be converted by FGE to include a formylglycine residue useful, e.g., for conjugating an agent (e.g., a therapeutic agent, an imaging agent, etc.) to the protein of interest.

Formylglycine-generating Enzymes

As used herein, a "formylglycine-generating enzyme" (or "FGE") is an enzyme that oxidizes cysteine or serine in a sulfatase motif (or "FGE recognition site") to a 2-formylglycine (FGly) residue (also referred to herein as a formylglycine residue). Thus, an "FGE" is used herein to refer to any enzyme that can act as an FGly-generating enzyme to mediate conversion of a cysteine ("Cys" or "C") of an FGE recognition site to FGly or that can mediate conversion of serine ("Ser" or "S") of an FGE recognition site to FGly. By "conversion" as used in the context of action of an FGE on an FGE recognition site refers to biochemical modification of a cysteine or serine residue in an FGE recognition site to a formylglycine (FGly) residue (e.g., Cys to FGly, or Ser to FGly). FGE recognition sites modified by an FGE to contain an FGly may be referred to herein as a "converted FGE recognition site".

It should be noted that in general, the literature refers to FGly-generating enzymes that convert a Cys to FGly in an FGE recognition site as FGEs, and refers to enzymes that convert Ser to FGly in an FGE recognition site as Ats-B-like. However, for purposes of the present disclosure "FGE" is used generically to refer to any enzyme that exhibits an FGly-generating enzyme activity at an FGE recognition site, with the understanding that an appropriate FGE may be selected according to the FGE recognition site (i.e., Cys-containing or Ser-containing) and/or the target protein containing the FGE recognition site.

As evidenced by the ubiquitous presence of sulfatases having an FGly at the active site, FGEs are found in a wide variety of cell types, including both eukaryotes and prokaryotes. There are at least two forms of FGEs. Eukaryotic sulfatases generally contain a cysteine in their sulfatase motif and are modified by the "SUMF1-type" FGE (see, e.g., Cosma et al. Cell 2003, 113, (4), 445-56; Dierks et al. Cell 2003, 113, (4), 435-44), which may be encoded by a SUMF1 gene. Prokaryotic sulfatases can contain either a cysteine or a serine in their sulfatase motif and are modified either by the "SUMF1-type" FGE or the "AtsB-type" FGE, respectively (see, e.g., Szameit et al. J Biol Chem 1999, 274, (22), 15375-81). Examples of prokaryotic FGEs include a *Mycobacterium tuberculosis* (Mtb) FGE and a *Streptomyces coelicolor* FGE. FGEs are also found in deuterostomia, including vertebrates and echinodermata (see, e.g., Pepe et al. (2003) Cell 113, 445-456, Dierks et al. (2003) Cell 113, 435-444; Cosma et al. (2004) Hum. Mutat. 23, 576-581).

In eukaryotes, FGE activity on a protein containing an FGE recognition sequence may occur during or shortly after translation of the protein in the endoplasmic reticulum (ER) (Dierks et al. Proc Natl Acad Sci USA 1997, 94(22):11963-8). Without being bound by theory, in prokaryotes it is thought that SUMF1-type FGE functions in the cytosol and AtsB-type FGE functions near or at the cell membrane. A SUMF2 FGE has also been described in deuterostomia, including vertebrates and echinodermata (see, e.g., Pepe et al. (2003) Cell 113, 445-456, Dierks et al. (2003) Cell 113, 435-444; Cosma et al. (2004) Hum. Mutat. 23, 576-581).

An FGE for use in the methods and compositions disclosed herein can be obtained from naturally occurring sources or synthetically produced. For example, an appropriate FGE can be derived from biological sources which naturally produce an FGE or which are genetically modified to express a recombinant gene encoding an FGE. When the methods described herein involve use of a host cell, the FGE may be native to the host cell, or the host cell can be genetically modified to express an FGE. Accordingly, the present disclosure also provides recombinant host cells genetically modified to express an FGE, which FGE may be selected so as to be compatible for use in conversion of a target protein having a selected FGE recognition site. In some embodiments, it may be desired to use a sulfatase motif compatible with a human FGE (see, e.g., the SUMF1-type FGE, see, e.g., Cosma et al. Cell 113, 445-56 (2003); Dierks et al. Cell 113, 435-44 (2003)), and express the protein having an FGE recognition site in a human cell that expresses a human FGE, or in a host cell, usually a mammalian cell, genetically modified to express a human FGE.

In certain embodiments, the FGE is a eukaryotic FGE, such as, but not limited to, a mammalian FGE. In some instances, the mammalian FGE is a human FGE. In certain embodiments, the FGE is a prokaryotic FGE, such as, but not limited to, a bacterial FGE. In some instances, the bacterial FGE is a *Mycobacterium tuberculosis* (Mtb) FGE or a *Streptomyces coelicolor* (*S. coelicolor*) FGE.

FGEs, as well as nucleic acids encoding a number of FGEs, are known in the art. See, for example in: Preusser et al. 2005 J. Biol. Chem. 280(15):14900-10 (Epub 2005 Jan. 18) (describing human FGEs and nucleic acids encoding the same); Fang et al. 2004 J Biol Chem. 279(15):14570-8 (Epub 2004 Jan. 28) (describing the bacterial formylglycine-generating sulfatase-modifying enzyme AtsB of *Klebsiella pneumonia* and nucleic acids encoding the same); Landgrebe et al. Gene 2003 Oct. 16; 316:47-56 (describing the identification of the gene (SUMF1) encoding human FGE and its conservation with prokaryotic genes encoding FGEs); Dierks et al. 1998 FEBS Lett. 423(1):61-5; Dierks et al. Cell. 2003 May 16; 113(4):435-44 (describing the gene encoding human FGE and mutations therein that cause Multiple Sulfatase Deficiency (MSD)); Cosma et al (2003 May 16) Cell 113(4):445-56 (describing the gene encoding human FGE and mutations therein that cause Multiple Sulfatase Deficiency (MSD)); Baenziger (2003 May 16) Cell 113(4):421-2 (review); Dierks et al. Cell. 2005 May 20; 121(4):541-52; Roeser et al. (2006 Jan. 3) Proc Natl Acad Sci USA 103(1):81-6; WO 2004/072275 (describing nucleic acids encoding human FGE and variants thereof); GenBank Accession No. NM_182760 (a single nucleotide variant of human FGE); and Carlson et al. *J Biol Chem.* 2008 283: 20117-20125 (describing nucleic acids that encode *Mycobacterium tuberculosis* (Mtb) FGE and *Streptomyces coelicolor* (*S. coelicolor*) FGE).

According to certain embodiments, the FGE is a full-length FGE. By "full-length" is meant the FGE has a complete, mature amino acid sequence of a wild-type FGE, including any wild-type isoforms (e.g., as a result of alternative splicing) of the corresponding wild-type FGE. As one example of a full-length FGE, the FGE may be a full-length human FGE, such as the full-length human FGE that includes an amino acid sequence having at least 80%, 85%, 90%, 95%, or more (e.g., 100%) sequence identity to the amino acid sequence (SEQ ID NO: 1)
MAAPALGLVCGRCPELGLVLLLLLLSLLCGAAGSQEAGTGAGAGSLAGSC

GCGTPQRPGAHGSSAAAHRYSREANAPGPVPGERQLAHSKMVPIPAGVFT

MGTDDPQIKQDGEAPARRVTIDAFYMDAYEVSNTEFEKFVNSTGYLTEAE

KFGDSFVFEGMLSEQVKTNIQQAVAAAPWWLPVKGANWRHPEGPDSTILH

RPDHPVLHVSWNDAVAYCTWAGKRLPTEAEWEYSCRGGLHNRLFPWGNKL

QPKGQHYANIWQGEFPVTNTGEDGFQGTAPVDAFPPNGYGLYNIVGNAWE

WTSDWWTVHHSVEETLNPKGPPSGKDRVKKGGSYMCHRSYCYRYRCAARS

QNTPDSSASNLGFRCAADRLPTMD;

provided in Table 4 below).

In other embodiments, the FGE is an N-terminally truncated FGE that retains formylglycine-generating activity. By "N-terminally truncated" is meant the FGE includes fewer than the number of amino acids present at the N-terminus of the corresponding wild-type FGE, including any wild-type isoforms (e.g., as a result of alternative splicing) of the corresponding wild-type FGE. Whether an N-terminally truncated FGE retains formylglycine-generating activity may be determined using any convenient approach, including combining the truncated FGE in vitro with a protein that includes an FGE recognition site under conditions in which an FGE having formylglycine-generating activity would convert a cysteine (or serine) residue of the FGE recognition site to a formylglycine residue, and determining whether the cysteine (or serine) residue of the FGE recognition site was converted to a formylglycine residue. Example in vitro reaction conditions and methods for detecting conversion to a formylglycine residue are described elsewhere herein.

In certain aspects, the N-terminally-truncated FGE (e.g., a human FGE truncated at the N-terminus) has a 1-72 amino acid N-terminal truncation, and maybe lack 1-5 amino acids, 1-10 amino acids, 1-15 amino acids, 1-20 amino acids, 1-25 amino acids, 1-30 amino acids, 1-35 amino acids, 1-40 amino acids, 1-45 amino acids, 1-50 amino acids, 1-55 amino acids, 1-60 amino acids, or 1-70 amino acids at the N-terminus relative to the corresponding full-length FGE.

In certain aspects, the truncated FGE is a human FGE truncated at the N-terminus, where the N-terminally-truncated human FGE is from 300 to 373 amino acids in length (e.g., 302 to 373 amino acids in length), such as from 302 to 370, from 302 to 360, from 302 to 350, from 302 to 340, from 302 to 330, from 302 to 320, or from 302 to 310 amino acids in length.

According to certain embodiments, the N-terminally truncated FGE corresponds in length to a naturally-occurring FGE protease cleavage product. For example, the N-terminally truncated FGE may correspond in length to a furin cleavage product of a human FGE. The furin enzyme cleaves between the arginine at position 72 and the glutamic acid at position 73 of human FGE, resulting in a cleavage product having a 72-amino acid N-terminal truncation relative to a human FGE that is not cleaved by the furin enzyme. According to one embodiment, the N-terminally truncated human FGE corresponds to the furin cleavage product of a human FGE that results in a 72 amino acid N-terminal truncation relative to a full-length human FGE, as shown in Table 4 (SEQ ID NO: 1).

TABLE 4

Example full-length human FGE (non-underlined and underlined amino acids) and example truncated human FGE (underlined only)

| | |
|---|---|
| Full-length human FGE (non-underlined and underlined amino acids) (SEQ ID NO: 1) | MAAPALGLVCGRCPELGLVLLLLLLSLLCGAA GSQEAGTGAGAGSLAGSCGCGTPQRPGAHGSS AAAHRYSREANAPGPVPGERQLAHSKMVPIPA GVFTMGTDDPQIKQDGEAPARRVTIDAFYMDA YEVSNTEFEKFVNSTGYLTEAEKFGDSFVFEG MLSEQVKTNIQQAVAAAPWWLPVKGANWRHPE GPDSTILHRPDHPVLHVSWNDAVAYCTWAGKR |
| N-terminally truncated human FGE (underlined amino acids only) (SEQ ID NO: 2) | LPTEAEWEYSCRGGLHNRLFPWGNKLQPKGQH YANIWQGEFPVTNTGEDGFQGTAPVDAFPPNG YGLYNIVGNAWEWTSDWWTVHHSVEETLNPKG PPSGKDRVKKGGSYMCHRSYCYRYRCAARSQN TPDSSASNLGFRCAADRLPTMD |

Nucleic acids encoding a full-length FGE or a truncated FGE, as well as expression vectors including the same, may be prepared using any suitable approach, including a recombinant DNA-based approach. As an example, a nucleic acid encoding a truncated FGE may be prepared by restriction digestion of a nucleic acid encoding a full-length FGE, or PCR amplification of the region encoding the truncated FGE using a nucleic acid encoding the full-length FGE as template. Such restriction digestion or amplification products may be cloned into an expression vector suitable for expression of the full-length or truncated FGE in a host cell of interest. The host cell of interest may then be transformed/transfected with the expression vector for subsequent production of the FGE in the host cell. Expression vectors and host cells that find use in producing full-length and truncated FGEs are described hereinbelow.

FGEs (e.g., full-length FGEs or N-terminally truncated FGEs) can be provided as a fusion protein in which the FGE is fused to an amino acid sequence heterologous to the FGE (e.g., a purification tag, a protease recognition sequence, secretion signal sequence, an endoplasmic reticulum (ER)-directing signal sequence, an ER retention sequence (e.g., KDEL (Lys-Asp-Glu-Leu)(SEQ ID NO:7)), and/or the like). FGEs disclosed herein (e.g., full-length FGEs, N-terminally truncated FGEs, and/or fusion proteins thereof) may be used in the methods as disclosed herein to provide activated FGEs.

FGE Recognition Sites

The FGE recognition site (also referred to herein as a "sulfatase motif") of the protein may vary. A minimal recognition site is usually 5 or 6 amino acid residues in length, usually no more than 6 amino acid residues in length.

The entire recognition site provided in the protein is at least 5 or 6 amino acid residues, and can be, for example, from 5 to 16, 6-16, 5-15, 6-15, 5-14, 6-14, 5-13, 6-13, 5-12, 6-12, 5-11, 6-11, 5-10, 6-10, 5-9, 6-9, 5-8, or 6-8 amino acid residues in length, so as to define an FGE recognition site of less than 16, 15, 14, 13, 12, 11, 10, 9, 8, 7 or 6 amino acid residues in length. In certain embodiments, the FGE recognition site of the protein is described by the formula:

$$X^1Z^1X^2Z^2X^3Z^3 \qquad (I)$$

where $Z^1$ is cysteine or serine (which can also be represented by (C/S));

$Z^2$ is either a proline or alanine residue (which can also be represented by (P/A));

$Z^3$ is a basic amino acid (e.g., arginine (R), and may be lysine (K) or histidine (H), usually lysine), or an aliphatic amino acid (alanine (A), glycine (G), leucine (L), valine (V), isoleucine (I), or proline (P), usually A, G, L, V, or I;

$X^1$ is present or absent and, when present, can be any amino acid, though usually an aliphatic amino acid, a sulfur-containing amino acid, or a polar, uncharged amino acid, (i.e., other than an aromatic amino acid or a charged amino acid), usually L, M, V, S or T, more usually L, M, S or V, with the proviso that when the FGE recognition site is at the N-terminus of the target polypeptide, $X^1$ is present; and $X^2$ and $X^3$ independently can be any amino acid, though usually an aliphatic amino acid, a polar, uncharged amino acid, or a sulfur containing amino acid (i.e., other than an aromatic amino acid or a charged amino acid), e.g., S, T, A, V, G or C; e.g., S, T, A, V or G. In one example, the FGE recognition site of the protein is of the formula L(C/S)TPSR (SEQ ID NO: 3), e.g., LCTPSR (SEQ ID NO: 4) or LSTPSR (SEQ ID NO: 5).

Examples of FGE recognition sites are described in, e.g., U.S. Pat. No. 7,985,783 and U.S. Patent Application Publication No. US2011/0117621, the disclosures of which are incorporated herein by reference in their entireties for all purposes.

Proteins that Include FGE Recognition Sites

The protein containing an FGE recognition site may be any protein of interest and includes proteins to which it is desirable to conjugate an agent of interest, e.g., a therapeutic agent, an imaging agent, etc. Proteins of interest include those having a naturally-occurring amino acid sequence, a native amino acid sequence having an N-terminal methionine, fragments of naturally-occurring proteins, and non-naturally occurring proteins and fragments thereof. In some embodiments, the protein is a protein other than a sulfatase or fragment thereof, other than a reporter protein, or other than preprolactin or prolactin.

The protein containing the FGE recognition sequence can be of the same or different origin as the FGE. Where the methods of the present disclosure involve a cell-based method, the protein containing the FGE recognition site may be endogenous to the host cell (e.g., a sulfatase) and/or the host cell may be genetically modified to express the protein containing an FGE recognition sequence. In this embodiment, the FGE may be endogenous to the host cell and/or the host cell may be genetically modified to express an FGE.

In certain aspects, the protein is a protein that may provide for a therapeutic or other clinical benefit, including proteins for which attachment to a moiety can provide for one or more of, for example, increased cytotoxicity upon binding of the protein to a target cell (e.g., a cancer cell), imaging (e.g., in vivo imaging) of a cell to which the protein binds, an increase in serum half-life, a decrease in an adverse immune response, additional or alternate biological activity or functionality, or other benefit or reduction of an adverse side effect. Where the therapeutic protein is an antigen for a vaccine, modification can provide for an enhanced immunogenicity of the protein.

The protein may be a member of a class of proteins, such as therapeutic proteins, including, but not limited to, cytokines, chemokines, ligands, growth factors, hormones, growth hormones, enzymes (e.g., sulfatases, e.g., a human sulfatase or functional fragment thereof), antibodies and antibody fragments (including antigen-binding antibody fragments), and antigens. Further examples include erythropoietin (EPO, e.g., native EPO, synthetic EPO (see, e.g., US 2003/0191291), human growth hormone (hGH), bovine growth hormone (bGH), follicle stimulating hormone (FSH), interferon (e.g., IFN-gamma, IFN-beta, IFN-alpha, IFN-omega, consensus interferon, and the like), insulin, insulin-like growth factor (e.g., IGF-I, IGF-II), blood factors (e.g., Factor VIII, Factor IX, Factor X, tissue plasminogen activator (TPA), and the like), colony stimulating factors (e.g., granulocyte-CSF (G-CSF), macrophage-CSF (M-CSF), granulocyte-macrophage-CSF (GM-CSF), and the like), transforming growth factors (e.g., TGF-beta, TGF-alpha), interleukins (e.g., IL-1, IL-2, IL-3, IL-4, IL-5, IL-6, IL-7, IL-8, IL-12, and the like), epidermal growth factor (EGF), platelet-derived growth factor (PDGF), fibroblast growth factors (FGFs, e.g., aFGF, bFGF), glial cell line-derived growth factor (GDNF), nerve growth factor (NGF), RANTES, and the like.

In some embodiments, the protein may provide a scaffold for attachment of a moiety of interest, such as a drug and/or imaging agent. Examples of such proteins include, but are not limited to, serum albumin (e.g., human serum albumin, bovine serum albumin), an Fc polypeptide (e.g., IgG Fc fragment (e.g., IgG1 Fc fragment, IgG2 Fc fragment, IgG3 Fc fragment, or IgG4 Fc fragment)), and the like. Here the protein is an Fc polypeptide, the Fc polypeptide may be a mammalian Fc polypeptide (e.g., human Fc polypeptide).

According to certain embodiments, the protein is an antibody or an antibody fragment. The terms "antibody" and "immunoglobulin" include antibodies or immunoglobulins of any isotype, whole antibodies (e.g., antibodies composed of a tetramer which in turn is composed of two heterodimers of a heavy and light chain polypeptide, including whole IgG, IgA, IgD, IgE, or IgM antibodies); half antibodies (e.g., antibodies that include a single dimer of a heavy and light chain polypeptide); antibody fragments (e.g., fragments of whole antibodies, such as fragments of IgG, IgA, IgD, IgE, or IgM antibodies) which retain specific binding to an antigen of interest, including, but not limited to Fab, F(ab')2, Fab', Fv, scFv, bispecific antibodies and diabodies; chimeric antibodies; monoclonal antibodies; humanized antibodies (e.g., humanized monoclonal antibodies, or humanized antibody fragments); or fully human antibodies (an antibody that comprises human immunoglobulin protein sequences only). Also included are human monoclonal antibodies that possess somatic mutations and/or N- or P-nucleotide additions and deletions as a result of V-D-J rearrangement. Also included are human antibodies to which synthetic sequences have been inserted into the complementarity determining regions (CDRs) (see, e.g., Miersch S & Sidhu S S (2012) Synthetic antibodies: concepts, potential and practical considerations. Methods 57(4):486-98; and Knappik et al. (2000) Fully synthetic human combinatorial antibody libraries (HuCAL) based on modular consensus frameworks and CDRs randomized with trinucleotides. *J. Mol. Biol.* 296(1): 57-86). In certain aspects, an antibody of the present disclosure is selected from an IgG (e.g., an IgG1, IgG2, IgG3 or IgG4 antibody), Fab, F(ab')2, and Fab'.

Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')2 fragment that has two antigen combining sites and is still capable of cross-linking antigen.

"Fv" comprises the minimum antibody fragment which contains a complete antigen-recognition and antigen-binding site. This region consists of a dimer of one heavy- and one light-chain variable domain in tight, non-covalent association. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The "Fab" fragment also contains the constant domain of the light chain and the first constant domain (CH1) of the heavy chain. Fab fragments differ from Fab' fragments by the addition of a few residues at the carboxyl terminus of the heavy chain CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

"Single-chain Fv" or "sFv" antibody fragments comprise the $V_H$ and $V_L$ domains of an antibody, where these domains are present in a single polypeptide chain. In some embodiments, the Fv polypeptide further comprises a polypeptide linker between the $V_H$ and $V_L$ domains, which enables the sFv to form the desired structure for antigen binding.

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites.

The term "recombinant" antibody as used herein is intended to include all antibodies that are prepared, expressed, created, or isolated by recombinant means, such as (i) antibodies expressed using a recombinant expression vector transfected into a host cell; (ii) antibodies isolated from a recombinant, combinatorial antibody library; (iii) antibodies isolated from an animal (e.g. a mouse) that is transgenic for human immunoglobulin genes; or (iv) antibodies prepared, expressed, created, or isolated by any other means that involves splicing of human immunoglobulin gene sequences to other DNA sequences, including, for example, in-vitro translation technology (see, e.g., Yin et al. (2012) A glycosylated antibodies and antibody fragments produced in a scalable in vitro transcription-translation system, *Landes Bioscience*, Volume 4, Issue 2). Such recombinant antibodies include humanized, CDR grafted, chimeric, deimmunized, and in vitro generated antibodies; and can optionally include constant regions derived from human germline immunoglobulin sequences.

By "humanized antibody" is meant immunoglobulins, half antibodies, immunoglobulin chains (e.g., a light chain polypeptide) or fragments thereof (such as Fv, scFv, Fab, Fab', F(ab')2 or other antigen-binding subsequences of antibodies) which contain sequence derived from both human and non-human immunoglobulin. The humanized antibodies may be human immunoglobulins (recipient antibody) in which residues from a complementary determining region (CDR) of the recipient are replaced by residues from a CDR of a non-human species (donor antibody) such as mouse, rat, lama, camel or rabbit having the desired specificity, affinity and capacity. In some instances, Fv framework residues of the human immunoglobulin are replaced by corresponding non-human residues. Furthermore, a humanized antibody may comprise residues which are found neither in the recipient antibody nor in the imported CDR or framework sequences.

Human light chain polypeptides are typically classified as kappa and lambda light chains. Furthermore, human heavy chain polypeptides are typically classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids.

In certain aspects, the protein comprising an FGE recognition site is an IgG or fragment thereof, a Fab, a F(ab')2, a Fab', an Fv, an ScFv, a bispecific antibody or fragment thereof, a diabody or fragment thereof, a chimeric antibody or fragment thereof, a monoclonal antibody or fragment thereof, a humanized antibody or fragment thereof, and a fully human antibody or fragment thereof.

Antigens of interest to which the antibody specifically binds include tumor-specific antigens, e.g., antigens present on the surface of malignant cells and not present on non-malignant cells. In other aspects, the antigen bound by the antibody is a tumor-associated antigen. By "tumor-associated antigen" is meant an antigen expressed on malignant cells with limited expression on cells of normal tissues, antigens that are expressed at much higher density on malignant versus normal cells, or antigens that are developmentally expressed.

Any tumor-associated antigen or tumor-specific antigen may be targeted by an antibody of the present disclosure. In certain aspects, when the methods of the present disclosure are for treatment of cancer, the antigen specifically bound by the antibody or antibody component of a conjugate of the present disclosure may include, but is not limited to, HER2, CD19, CD22, CD30, CD33, CD56, CD66/CEACAM5, CD70, CD74, CD79b, CD138, Nectin-4, Mesothelin, Transmembrane glycoprotein NMB (GPNMB), Prostate-Specific Membrane Antigen (PSMA), SLC44A4, CA6, CA-IX, or any other tumor-associated or tumor-specific antigens of interest.

By "specific binding" or "specifically binds" in the context of a characteristic of an antibody refers to the ability of an antibody to preferentially bind to a particular antigen that is present in a homogeneous mixture of different antigens. In certain embodiments, a specific binding interaction will discriminate between desirable and undesirable antigens (or "target" and "non-target" antigens) in a sample or organism (e.g., a human), in some embodiments more than about 10 to 100-fold or more (e.g., more than about 1000- or 10,000-fold). In certain embodiments, the affinity between an antibody and antigen when they are specifically bound in an antibody-antigen complex is characterized by a KD (dissociation constant) of less than $10^{-6}$ M, less than $10^{-7}$ M, less than $10^{-8}$ M, less than $10^{-9}$ M, less than $10^{-10}$ M, less than $10^{-11}$ M, or less than about $10^{-12}$ M or less.

Methods of Producing Activated FGEs

The present disclosure provides methods of producing activated FGEs. As used herein, an "activated formylglycine-generating enzyme" or "activated FGE" refers to an FGE that has been treated with an oxidation reagent by addition of oxidation reagent to a cell expressing an FGE and/or by addition of oxidation reagent to isolated FGE. Accordingly, in certain aspects, the present disclosure provides methods of producing an activated FGE, which methods include treating an FGE with an oxidation reagent to produce an activated FGE. By "oxidation reagent" is meant a reagent capable of oxidizing FGE (which may be referred to as an "oxidizing agent"), a reagent capable of catalyzing the oxidation of FGE, or a combination thereof. One example of a reagent capable of catalyzing the oxidation of FGE is $Cu^{2+}$. One example of an oxidation reagent that includes a reagent capable of oxidizing FGE and a reagent that catalyzes the oxidation of FGE is a reagent that includes elemental oxygen as a terminal oxidant and a transition metal, such as, but not limited to, $Cu^{2+}$. These and other suitable oxidation reagents are described below.

Activated FGE may be produced as part of an in vivo protein synthesis method in which the FGE is expressed and activated within a host cell, which method may optionally include co-expression of a protein of interest containing an FGE recognition site in the host cell. That is, the FGE may be present in a host cell, and the FGE is treated to produce an activated FGE by providing an oxidation reagent (e.g., $Cu^{2+}$) in a cell culture medium in which the host cell is being cultured. For example, the present inventors have found that treatment of FGE-expressing cells with an oxidation reagent such as $Cu^{2+}$ (by providing $Cu^{2+}$ in the cell culture medium) provides for FGE activation such that cysteine residues within FGE recognition sites of target proteins co-expressed in the treated cells are converted to formylglycine residues at an increased yield as compared to conversion in cells not treated with $Cu^{2+}$ but otherwise under identical conditions (see the Examples section below). For example, treatment of FGE-expressing cells with an oxidation reagent as described herein may produce an increase in the population of activated FGE produced by the FGE-expressing cells. Similarly, treatment of FGE-expressing cells with an oxidation reagent as described herein may produce a decrease in the population of FGE that is not activated FGE produced by the FGE-expressing cells.

Accordingly, in certain embodiments, the oxidation reagent is $Cu^{2+}$, and treating an FGE includes culturing a cell that includes a nucleic acid encoding the FGE in a cell culture medium that includes $Cu^{2+}$, where the culturing is under conditions in which the FGE is expressed in the cell. In certain aspects, the present disclosure provides methods that include culturing a cell that includes a nucleic acid encoding an FGE in a cell culture medium that includes $Cu^{2+}$, where the culturing is under conditions in which the FGE is expressed in the cell.

The source of $Cu^{2+}$ (e.g., a copper salt or other suitable $Cu^{2+}$ source) and the $Cu^{2+}$ concentration in the cell culture medium may be selected so as to be cell culture compatible, e.g., without affecting or substantially affecting cell viability, protein expression levels, etc. For example, when the host cell is a prokaryotic cell, the $Cu^{2+}$ source and concentration may be selected so as to be compatible with prokaryotic cell culture. Similarly, when the host cell is, e.g., a mammalian cell, the $Cu^{2+}$ source and concentration may be selected so as to be compatible with mammalian cell culture. Examples of culture conditions suitable for in vivo FGE activation in prokaryotic and mammalian cells are provided in the Examples section below.

In certain aspects, the $Cu^{2+}$ is provided by addition of a copper salt to the cell culture medium. Suitable copper salts include, but are not limited to, copper sulfate (i.e., copper(II) sulfate, $CuSO_4$), copper citrate, copper tartrate, copper nitrate, and any combination thereof.

The $Cu^{2+}$ is present in the cell culture medium at a concentration suitable for FGE activation. In certain aspects, the $Cu^{2+}$ is present in the cell culture medium at a concentration of from 1 nM to 100 mM, such as from 0.1 µM to 10 mM, from 0.5 µM to 5 mM, from 1 µM to 1 mM, from 2 µM to 500 µM, from 3 µM to 250 µM, from 4 µM to 150 µM, or from 5 µM to 100 µM (e.g., from 5 µM to 50 µM).

According to certain embodiments, the $Cu^{2+}$ is present in the cell culture medium at a concentration of 1 nM or more, 10 nM or more, 100 nM or more, 1 µM or more, 5 µM or more, 10 µM or more, 20 µM or more, 30 µM or more, 40 µM or more, 50 µM or more, 100 µM or more, 200 µM or more, 300 µM or more, 400 µM or more, 500 µM or more, 1 mM or more, 10 mM or more, or 100 mM or more. In certain aspects, the $Cu^{2+}$ is present in the cell culture medium at a concentration of 100 mM or less, 10 mM or less, 1 mM or less, 500 µM or less, 400 µM or less, 300 µM or less, 200 µM or less, 100 µM or less, 50 µM or less, 40 µM or less, 30 µM or less, 20 µM or less, 10 µM or less, 5 µM or less, 1 µM or less, 100 nM or less, 10 nM or less, or 1 nM or less.

Host cells suitable for in vivo FGE activation include, e.g., prokaryotic cells (e.g., *E. coli* cells) and eukaryotic cells (e.g., yeast cells, insect cells, mammalian cells, etc.). The cell may be genetically modified to express and FGE or interest and/or the FGE may be endogenous to the cell.

*Escherichia coli* is an example of a prokaryotic host cell which may be used to practice the methods of producing an activated FGE. Other microbial hosts suitable for use include bacilli, such as *Bacillus subtilis*, and other enterobacteriaceae, such as *Salmonella, Serratia*, and various *Pseudomonas* species. In these prokaryotic hosts, one can make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Other microbes, such as yeast, are also useful for practicing the methods of producing an activated FGE. *Saccharomyces* (e.g., *S. cerevisiae*) and *Pichia* are examples of suitable yeast host cells, with suitable vectors having expression control sequences (e.g., promoters), an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

In addition to microorganisms, mammalian cells may be employed to practice the methods of producing an activated FGE. The mammalian cell may be a rodent cell, a human cell, or any other mammalian cell of interest, including but not limited to a cell selected from: a CHO cell, a HEK cell, a BHK cell, a COS cell, a Vero cell, a Hela cell, an NIH 3T3 cell, a Huh-7 cell, a PC12 cell, a RAT1 cell, a mouse L cell, an HLHepG2 cell, an NSO cell, a C127 cell, a hybridoma cell, a PerC6 cell, a CAP cell, and a Sp-2/0 cell. Expression vectors for these cells can include expression control sequences, such as an origin of replication, a promoter, and an enhancer (Queen et al., Immunol. Rev. 89:49 (1986)), and necessary processing information sites, such as ribosome binding sites, RNA splice sites, polyadenylation sites, and transcriptional terminator sequences. Examples of suitable expression control sequences are promoters derived from immunoglobulin genes, SV40, adenovirus, bovine papilloma virus, cytomegalovirus and the like. See Co et al., J. Immunol. 148:1149 (1992).

Culture conditions suitable for expressing FGEs in host cells are described, for example in U.S. Pat. No. 7,985,783 and U.S. Patent Application Publication No. US2011/0117621, the disclosures of which are incorporated herein by reference in their entireties for all purposes. The FGE may be endogenous to the host cell, or the host cell may be recombinant for a suitable FGE that is heterologous to the host cell. FGE expression can be provided by an expression system endogenous to the FGE gene (e.g., expression is provided by a promoter and other control elements present in the native FGE gene of the host cell), or can be provided by from a recombinant expression system in which the FGE coding sequence is operably linked to a heterologous promoter to provide for constitutive or inducible expression. Use of a strong promoter to provide high levels of FGE expression may be of particular interest in certain embodiments. The type of cell culture medium and components therein may be selected so as to be compatible with the particular cell type in which the FGE is expressed.

The methods may further include purifying the activated FGE from the cell and/or the oxidation reagent. Any convenient protein purification procedures may be used to isolate the activated FGE. See, e.g., Guide to Protein Purification, 2nd Edition (Burgess & Deutscher ed.) (Academic Press, 2009) (ISBN: 9780123745361). For example, a lysate may be prepared from a cell that produces an activated FGE, and purified using HPLC, size exclusion chromatography, gel electrophoresis, affinity chromatography, and the like.

Activated FGE may also be produced as part of an in vitro, cell-free, protein synthesis method, which method may optionally include co-expression of a target polypeptide containing an FGE recognition sequence in the reaction mixture. Accordingly, in certain aspects, the methods of the present disclosure include expressing the FGE in a cell-free reaction mixture with an oxidation reagent, where the oxidation reagent can be $Cu^{2+}$. According to these aspects, the cell-free reaction mixture is such that the FGE is not expressed in a cell, but rather in a reaction mixture suitable for in vitro protein synthesis. Exemplary cell-free reaction mixtures include, but are not limited to, cell-free extracts, cell lysates, and reconstituted translation systems, along with the nucleic acid template(s) for synthesis of an FGE and any other desired proteins (e.g., a protein having an FGE recognition site as described elsewhere herein).

The cell-free reaction mixture may include monomers for a macromolecule to be synthesized, e.g. amino acids, nucleotides, etc., and such co-factors, enzymes and any other necessary reagents, e.g. ribosomes, tRNA, polymerases, transcriptional factors, etc. In addition to the above components such as a cell-free extract, nucleic acid template, and amino acids, materials specifically required for protein synthesis may be added to the reaction. The materials may include salts, folinic acid, cyclic AMP, inhibitors for protein or nucleic acid degrading enzymes, inhibitors or regulators of protein synthesis, adjusters of oxidation/reduction potentials, non-denaturing surfactants, buffer components, spermine, spermidine, putrescine, etc. Various cell-free synthesis reaction systems are described, for example, in Kim, D. M. and Swartz, J. R. Biotechnol. Bioeng. 66: 180-8 (1999); Kim, D. M. and Swartz, J. R. Biotechnol. Prog. 16:385-90 (2000); Kim, D. M. and Swartz, J. R. Biotechnol. Bioeng. 74:309-16 (2001); Swartz et al, Methods MoL Biol. 267: 169-82 (2004); Kim, D. M. and Swartz, J. R. Biotechnol. Bioeng. 85: 122-29 (2004); Jewett, M. C. and Swartz, J. R., Biotechnol. Bioeng. 86: 19-26 (2004); Yin, G. and Swartz, J. R., Biotechnol. Bioeng. 86: 188-95 (2004); Jewett, M. C. and Swartz, J. R., Biotechnol. Bioeng. 87:465-72 (2004); Voloshin, A. M. and Swartz, J. R., Biotechnol. Bioeng. 91:516-21 (2005). Additional conditions for the cell-free synthesis of proteins of interest are described in International Publication No. WO2010/081110, the disclosure of which is incorporated herein by reference in its entirety.

In certain embodiments, cell-free protein synthesis offers certain advantages over conventional in vivo protein expression methods. Cell-free systems can direct most, if not all, of the metabolic resources of the cell towards the exclusive production of one protein. Moreover, the lack of a cell wall and membrane components in vitro may be advantageous since it allows for control of the synthesis environment. For example, tRNA levels can be changed to reflect the codon usage of genes being expressed. The type or concentration of the oxidation reagent, the redox potential, pH, or ionic strength can also be altered with greater flexibility than with in vivo protein synthesis because concerns of cell growth or viability do not exist. Furthermore, direct recovery of purified, properly folded protein products can be easily achieved.

Activated FGE may also be produced as part of an in vitro activation method. According to such embodiments, the FGE is not expressed in the presence of an oxidation reagent. Such methods are based on the present inventors' discovery that expressing an FGE (e.g., in a cell or a cell-free translation system), purifying the FGE, and then treating the FGE with an oxidation reagent in vitro results in activation of the FGE. Such in vitro activated FGEs convert cysteine or serine residues within FGE recognition sites of target proteins at an increased efficiency as compared to conversion by non-activated FGEs under otherwise identical conditions (see the Examples section below).

The oxidation reagent used for the activation of FGE may be selected from any convenient oxidation reagent that is compatible with the desired reaction conditions. For example, the oxidation reagent may be elemental oxygen, such as elemental oxygen as a terminal oxidant. In some cases, elemental oxygen as a terminal oxidant may be provided as oxygen, a mixture of oxygen and hydrogen sulfide, oxygen under basic conditions, and the like.

In certain embodiments, the oxidation reagent is elemental oxygen, such as elemental oxygen as a terminal oxidant, where the reaction is catalyzed by a transition metal. In these instances, the oxidation reagent may include, but is not limited to, copper(II) (i.e., $Cu^{2+}$) or a source of copper(II) (e.g., copper sulfate ($CuSO_4$), copper citrate, copper tartrate, copper nitrate, Fehling's reagent, Benedict's reagent, etc.), which can catalyze oxygen activation. In some instances, the oxidation reagent (e.g., $Cu^{2+}$) that can catalyze oxygen activation is provided in the presence of oxygen. For example, the oxidation reagent may include oxygen and $Cu^{2+}$, a source of $Cu^{2+}$, or combinations thereof.

In certain embodiments, the oxidation reagent is copper (II) (i.e., $Cu^{2+}$) or a source of copper(II) (i.e., a source of $Cu^{2+}$). In some instances, the copper(II) or the source of copper(II) is provided in the presence of oxygen. In some cases, the oxidation reagent is copper(II), such as copper(II) and oxygen. In some cases, the oxidation reagent is a source of copper(II), such as a source of copper(II) and oxygen. In certain cases, the source of copper(II) is, but not limited to, copper sulfate, copper citrate, copper tartrate, Fehling's reagent, Benedict's reagent, combinations thereof, and the like. In some instances, the source of copper(II) is copper sulfate ($CuSO_4$).

Reaction conditions for the in vitro oxidation of proteins may vary according to the specific oxidation reagent employed. Example reaction conditions for the in vitro activation of FGE using example oxidation reagents are provided below in the Examples section.

Activation of the FGE may include combining in an FGE activation reaction mixture, an FGE, and an oxidation reagent. In some instances, the FGE activation reaction mixture is an aqueous solution. In certain cases, the FGE activation reaction mixture is a buffered aqueous solution, e.g., an aqueous solution that includes a buffer, such as, but not limited to, triethanolamine. In certain instances, the buffered aqueous solution has a pH range compatible with FGE, such as a pH range from 5 to 10, or from 5 to 9, or from 6 to 8, e.g., a pH of about 7, such as a pH of 7.4.

In certain embodiments, activation of the FGE may include combining in an FGE activation reaction mixture an FGE and an oxidation reagent, where the FGE is present in the FGE activation reaction mixture and the oxidation reagent is then added to the FGE activation reaction mixture. In other embodiments, activation of the FGE may include combining in an FGE activation reaction mixture, an FGE, and an oxidation reagent, where the oxidation reagent is present in the FGE activation reaction mixture and the FGE is then added to the FGE activation reaction mixture.

In certain embodiments, the mol ratio of FGE to oxidation reagent in the FGE activation reaction mixture is 5:1, or 4:1, or 3:1, or 2:1, or 1:1, or 1:2, or 1:3, or 1:4, or 1:5. In some instances, the mol ratio of FGE to oxidation reagent in the FGE activation reaction mixture is 1:2.

In certain cases, after the FGE and the oxidation reagent are combined in the FGE activation reaction mixture, the FGE activation reaction mixture is mixed. Any convenient method for mixing the FGE activation reaction mixture may be used, such as stirring, vortexing, and the like. The FGE activation reaction mixture may be mixed for a period of time to allow sufficient activation of the FGE to activated FGE, such as 15 min or more, or 30 min or more, or 45 min or more, or 1 hr or more, or 2 hr or more, or 3 hr or more, or 4 hr or more, or 5 hr or more. In some cases, the FGE activation reaction mixture is mixed for 1 hr. Mixing of the FGE activation reaction mixture may be performed at about room temperature, e.g., a temperature ranging from 20° C. to 30° C., such as 25° C. Temperatures suitable for activation may vary according to the particular oxidation reagent employed.

Sufficient activation of the FGE to activated FGE may be measured using an FGE activity assay as described herein. After sufficient activation of the FGE to activated FGE, the activated FGE may be separated from the FGE activation reaction mixture. Any convenient method for protein separation may be used to separate the activated FGE from the FGE activation reaction mixture, such as, but not limited to, dialysis, buffer exchange, diafiltration, precipitation, ion exchange chromatography, affinity chromatography, electrophoresis, and the like. In some instances, the activated FGE may be separated from the FGE activation reaction mixture by buffer exchange.

Also provided by the present disclosure is an activated FGE produced by any of the methods described herein for producing an activated FGE. According to certain embodiments, the activated FGE is not purified from the oxidation reagent. For example, the FGE may be present in the cell or reaction mixture in which the FGE was treated with the oxidation reagent. In other aspects, the activated FGE is separated from the FGE activation reaction mixture using a suitable protein separation procedure, including any such separation procedures described elsewhere herein.

Methods of Using Activated FGEs

The activated FGEs of the present disclosure find use in a variety of in vivo and in vitro applications in which it is desirable, e.g., to convert a cysteine residue or a serine residue of an FGE recognition site in a protein of interest (or "target protein") to a formylglycine residue. The aldehyde group of the formylglycine residue is useful, e.g., for site-specifically conjugating an agent of interest (e.g., a therapeutic agent, an imaging agent, etc.) to the target protein. Accordingly, the present disclosure provides methods of using activated FGEs.

In certain aspects, provided are methods of producing a protein that includes a formylglycine residue. The methods include combining an activated formylglycine-generating enzyme (FGE) with a protein that includes an FGE recognition site, under conditions in which the activated FGE converts a cysteine residue or a serine residue of the FGE recognition site to a formylglycine residue, to produce a protein including a formylglycine residue.

In some embodiments, the activated FGE and the protein having the FGE recognition site are combined in a reaction mixture that includes a reducing agent. In some embodiments, the reducing agent promotes conversion of the cysteine residue or the serine residue of the FGE recognition site to the formylglycine residue. In some embodiments, the reducing agent is 2-mercaptoethanol. As used herein, promoting the conversion of the cysteine residue or the serine residue of the FGE recognition site to the formylglycine residue refers to an increase in the amount (e.g., concentration) of fGly produced by the activated FGE as compared to a conversion reaction in the absence of the reducing agent. In certain cases, the reducing agent increases the amount of fGly produced by the activated FGE by 5% or more, or 10% or more, or 15% or more, or 20% or more, or 25% or more, or 30% or more, or 35% or more, or 40% or more, or 45% or more, or 50% or more, or 55% or more, or 60% or more, or 65% or more, or 70% or more, or 75% or more, or 80% or more, or 85% or more, or 90% or more, or 95% or more, or 100% or more, as compared to a conversion reaction in the absence of the reducing agent. In certain embodiments, the reducing agent increases the amount of fGly produced by the activated FGE by 50% or more, as compared to a conversion reaction in the absence of the reducing agent.

In Vivo Conversion

The protein that includes a formylglycine residue may be produced within a host cell as part of an in vivo protein synthesis and conversion method. According to certain embodiments, combining an activated FGE with a protein including an FGE recognition site includes culturing a cell that includes an FGE and a protein including an FGE recognition site. The culturing is in a cell culture medium that includes $Cu^{2+}$ as the oxidation reagent, under cell culture conditions in which the FGE converts a cysteine residue or a serine residue of the FGE recognition site to a formylglycine residue. In certain aspects, the cell includes nucleic acids that encode the FGE and the protein including an FGE recognition site, such that the FGE and protein including an FGE recognition site are co-expressed in the cell.

The source of $Cu^{2+}$ (e.g., a copper salt or other suitable $Cu^{2+}$ source) and the $Cu^{2+}$ concentration in the cell culture medium may be selected so as to be cell culture compatible, e.g., without affecting or substantially affecting cell viability, protein expression levels, etc. For example, when the host cell is a prokaryotic cell, the $Cu^{2+}$ source and concentration may be selected so as to be compatible with prokaryotic cell culture. Similarly, when the host cell is, e.g., a mammalian cell, the $Cu^{2+}$ source and concentration may be selected so as to be compatible with mammalian cell culture. Examples of culture conditions suitable for in vivo FGE activation in prokaryotic and mammalian cells are provided in the Examples section below.

In certain aspects, the $Cu^{2+}$ is provided by addition of a copper salt to the cell culture medium. Suitable copper salts include, but are not limited to, copper sulfate (i.e., copper(II) sulfate, $CuSO_4$), copper citrate, copper tartrate, copper nitrate, and any combination thereof.

The $Cu^{2+}$ is present in the cell culture medium at a concentration suitable for FGE activation. In certain aspects, the $Cu^{2+}$ is present in the cell culture medium at a concentration of from 1 nM to 100 mM, such as from 0.1 µM to 10 mM, from 0.5 µM to 5 mM, from 1 µM to 1 mM, from 2 µM to 500 µM, from 3 µM to 250 µM, from 4 µM to 150 µM, or from 5 µM to 100 µM (e.g., from 5 µM to 50 µM).

According to certain embodiments, the $Cu^{2+}$ is present in the cell culture medium at a concentration of 1 nM or more, 10 nM or more, 100 nM or more, 1 µM or more, 5 µM or more, 10 µM or more, 20 µM or more, 30 µM or more, 40 µM or more, 50 µM or more, 100 µM or more, 200 µM or more, 300 µM or more, 400 µM or more, 500 µM or more, 1 mM or more, 10 mM or more, or 100 mM or more. In certain aspects, the $Cu^{2+}$ is present in the cell culture medium at a concentration of 100 mM or less, 10 mM or less, 1 mM or less, 500 µM or less, 400 µM or less, 300 µM or less, 200 µM or less, 100 µM or less, 50 µM or less, 40 µM or less, 30 µM or less, 20 µM or less, 10 µM or less, 5 µM or less, 1 µM or less, 100 nM or less, 10 nM or less, or 1 nM or less.

Host cells suitable for co-expression of an FGE and a protein including an FGE recognition site include, e.g., prokaryotic cells (e.g., *E. coli* cells) and eukaryotic cells (e.g., yeast cells, insect cells, mammalian cells, etc.).

*Escherichia coli* is an example of a prokaryotic host cell which may be used to practice the methods of producing a protein that includes a formylglycine residue. Other microbial hosts suitable for use include bacilli, such as *Bacillus subtilis*, and other enterobacteriaceae, such as *Salmonella, Serratia*, and various *Pseudomonas* species. In these prokaryotic hosts, one can make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Other microbes, such as yeast, are also useful for practicing the methods of producing a protein that includes a formylglycine residue. *Saccharomyces* (e.g., *S. cerevisiae*) and *Pichia* are examples of suitable yeast host cells, with suitable vectors having expression control sequences (e.g., promoters), an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

In addition to microorganisms, mammalian cells may be employed to practice the methods of producing a protein that includes a formylglycine residue. The mammalian cell may be a rodent cell, a human cell, or any other mammalian cell of interest, including but not limited to a cell selected from: a CHO cell, a HEK cell, a BHK cell, a COS cell, a Vero cell, a Hela cell, an NIH 3T3 cell, a Huh -7 cell, a PC12 cell, a RAT1 cell, a mouse L cell, an HLHepG2 cell, an NSO cell, a C127 cell, a hybridoma cell, a PerC6 cell, a CAP cell, and a Sp-2/0 cell. Expression vectors for these cells can include expression control sequences, such as an origin of replication, a promoter, and an enhancer (Queen et al., Immunol. Rev. 89:49 (1986)), and necessary processing information sites, such as ribosome binding sites, RNA splice sites, polyadenylation sites, and transcriptional terminator sequences. Examples of suitable expression control sequences are promoters derived from immunoglobulin genes, SV40, adenovirus, bovine papilloma virus, cytomegalovirus and the like. See Co et al., J. Immunol. 148: 1149 (1992).

Cell-Free Conversion in the Context of an In Vitro Transcription Method

The protein that includes a formylglycine residue may be produced as part of an in vitro, cell-free, protein synthesis and conversion method. In certain aspects, the methods include expressing an FGE and the protein including an FGE recognition site in a cell-free reaction mixture that includes an oxidation reagent (e.g., $Cu^{2+}$) under conditions in which the FGE converts a cysteine residue or a serine residue of the FGE recognition site to a formylglycine residue. According to these aspects, the cell-free reaction mixture is such that the FGE and the protein including an FGE recognition site are not expressed in a cell, but rather in a reaction mixture suitable for in vitro protein synthesis. Exemplary cell-free reaction mixtures include, but are not limited to, cell-free extracts, cell lysates, and reconstituted translation systems, along with nucleic acid templates for synthesis of an FGE and the protein including an FGE recognition site. The components of the cell free reaction mixture may be as described hereinabove with respect to the in vitro, cell-free, protein synthesis methods for producing an activated FGE.

In Vitro Conversion Using Activated FGE

The protein that includes a formylglycine residue may be produced as part of an in vitro conversion method, in which an activated FGE and a protein including an FGE recognition site are combined in a cell-free reaction mixture. According to these embodiments, the FGE and the protein including an FGE recognition site are not expressed in the cell-free reaction mixture. Such methods are based on expressing an FGE (e.g., in a cell or a cell-free translation system), purifying the FGE, and then treating the FGE with an oxidation reagent in vitro to produce activation of the FGE. Such in vitro activated FGEs convert cysteine or serine residues within FGE recognition sites of proteins that include FGE recognition sites at an increased efficiency as compared to conversion by non-activated FGEs under otherwise identical conditions (see the Examples section below).

In some embodiments, the reaction mixture includes a copper(II) ion (i.e., $Cu^{2+}$), or a source of copper(II) ions, e.g., copper sulfate ($CuSO_4$), copper citrate, copper tartrate, and the like. Expressing the FGE and the protein having the FGE recognition site in the cell-free reaction mixture containing $Cu^{2+}$ may occur under conditions in which the FGE converts a cysteine residue or a serine residue of the FGE recognition site to a formylglycine (Fgly) residue, as described herein.

In certain embodiments, the in vitro method of producing a protein having an FGly residue includes combining an activated FGE and the protein having the FGE recognition site in a cell-free reaction mixture. In these embodiments, the FGE may be activated to form an activated FGE prior to combining the activated FGE and the protein having the FGE recognition site. By "activated" is meant that the activated FGE has a greater activity as compared to an FGE that has not been activated, e.g., a greater activity for the conversion of a cysteine or a serine residue in of the FGE recognition site to an FGly. For instance, an activated FGE may have an activity (as measured using an FGE activity assay as described herein) that is 1.5 times or more, 2 times or more, 5 times or more, 10 times or more, 20 times or more, 30 times or more, 40 times or more, 50 times or more, 60 times or more, 70 times or more, 80 times or more, 90 times or more, 100 times or more active, such as 200 times or more, including 300 times or more, or 400 times or more, or 500 times or more, or 600 times or more, or 700 times or more, or 800 times or more, or 900 times or more, or 1000 times or more, or 1500 times or more, or 2000 times or more, or 2500 times or more, or 3000 times or more, or 3500 times or more, or 4000 times or more, or 4500 times or more, or 5000 times or more, or 5500 times or more, or 6000 times or more, or 6500 times or more, or 7000 times or more, or 7500 times or more, or 8000 times or more, or 8500 times or more, or 9000 times or more, or 9500 times or more, or 10,000 times or more active than an FGE that has not been activated. In certain instances, the activated FGE has an activity (as measured using an FGE activity assay as described herein) that is 3000 times or more active than an FGE that has not been activated. In some cases, the activated FGE has an activity (as measured using an FGE activity assay as described herein) that is 1.5 to 10,000 times more, 2 to 10,000 times more, 5 to 10,000 times more, 10 to 10,000 times more, 20 to 10,000 times more, 30 to 10,000 times more, 40 to 10,000 times more, 50 to 10,000 times more, 60 to 10,000 times more, 70 to 10,000 times more, 80 to 10,000 times more, 90 to 10,000 times more, 100 to 10,000 times more active, such as 500 to 9000 times more, including 1000 to 8000 times more, or 1000 to 7000 times more, or 1000 to 6000 times more, or 1000 to 5000 times more, or 1000 to 4000 times, or 2000 to 4000 times more active than an FGE that has not been activated. In certain instances, the activated FGE has an activity (as measured using an FGE activity assay as described herein) that is 2000 to 4000 times more active than an FGE that has not been activated.

In certain embodiments, the FGE may be activated to form an activated FGE prior to combining the activated FGE and the protein having the FGE recognition site. As such, in some instances, the method includes activating the FGE with an oxidation reagent prior to combining the activated FGE with the protein having the FGE recognition site.

The oxidation reagent used for the activation of FGE may be selected from any convenient oxidation reagent that is compatible with the desired reaction conditions. For example, the oxidation reagent may be elemental oxygen, such as elemental oxygen as a terminal oxidant. In some cases, elemental oxygen as a terminal oxidant may be provided as oxygen, a mixture of oxygen and hydrogen sulfide, oxygen under basic conditions, and the like.

In certain embodiments, the oxidation reagent is elemental oxygen, such as elemental oxygen as a terminal oxidant, where the reaction is catalyzed by a transition metal. In these instances, the oxidation reagent may include, but is not limited to, copper(II), a source of copper(II) (e.g., copper sulfate, copper citrate, copper tartrate, Fehling's reagent, Benedict's reagent, etc.), which can catalyze oxygen activation. In some instances, the oxidation reagent (e.g., $Cu^{2+}$) that can catalyze oxygen activation is provided in the presence of oxygen. For example, the oxidation reagent may include oxygen and $Cu^{2+}$, a source of $Cu^{2+}$, or combinations thereof.

In certain embodiments, the oxidation reagent is copper (II) or a source of copper(II). In some instances, the copper (II) or the source of copper(II) is provided in the presence of oxygen. In some cases, the oxidation reagent is copper(II), such as copper(II) and oxygen. In some cases, the oxidation reagent is a source of copper(II), such as a source of copper(II) and oxygen. In certain cases, the source of copper(II) is, but not limited to, copper sulfate, copper citrate, copper tartrate, Fehling's reagent, Benedict's reagent, combinations thereof, and the like. In some instances, the source of copper(II) is copper sulfate.

As described above, in certain embodiments, the mol ratio of FGE to oxidation reagent is 5:1, or 4:1, or 3:1, or 2:1, or 1:1, or 1:2, or 1:3, or 1:4, or 1:5. In some instances, the mol ratio of FGE to oxidation reagent in the FGE activation reaction mixture is 1:2.

As described above, in certain embodiments, the in vitro method of producing a protein having an FGly residue includes combining an activated FGE and the protein having the FGE recognition site in a cell-free reaction mixture. As described above, the FGE may be activated to form an activated FGE prior to combining the activated FGE and the protein having the FGE recognition site. Approaches for producing an activated FGE are described in detail above in the description of the methods for producing activated FGEs.

In certain embodiments, the ratio of the activated FGE to the protein having the FGE recognition site (i.e., the ratio of activated FGE to protein in the conversion reaction) is 200% by mol or less, such as 150% by mol or less, or 100% by mol or less, or 75% by mol or less, or 50% by mol or less, or 25% by mol or less, or 10% by mol or less, or 5% by mol or less, or 3% by mol or less, or 1% by mol or less, or 0.7% by mol or less, or 0.5% by mol or less, or 0.4% by mol or less, or 0.3% by mol or less, or 0.2% by mol or less, or 0.1% by mol or less, or 0.07% by mol or less, or 0.05% by mol or less, or 0.03% by mol or less, or 0.01% by mol or less, or 0.005% by mol or less. In certain embodiments, the ratio of the activated FGE to the protein having the FGE recognition site is 0.1% by mol or less, such as 0.1% by mol.

According to certain embodiments, the methods of producing a protein comprising a formylglycine residue further include conjugating an agent to the produced protein via the aldehyde moiety of the formylglycine residue. In certain aspects, the agent is a therapeutic agent, an imaging agent, an agent that increases serum half-life of the protein upon administration to a subject, an agent that reduces immunogenicity of the protein upon administration to a subject, an agent that increases immunogenicity of the protein upon administration to a subject (e.g., when the protein is a vaccine), or any other desirable agents for conjugation to the produced protein.

According to certain embodiments, the methods include conjugating a therapeutic agent to the protein. In certain aspects, the therapeutic agent is selected from a cytotoxic agent, an antiproliferative agent, an antineoplastic agent, an antibiotic agent, an antifungal agent, and an antiviral agent.

According to certain embodiments, the agent of interest is an imaging agent. The imaging agent may be, e.g., a fluorescent dye, a near-infrared (NIR) imaging agent, and a single-photon emission computed tomography (SPECT)/CT imaging agent, a nuclear magnetic resonance (NMR) imaging agent, a magnetic resonance imaging (MRI) agent, a positron-emission tomography (PET) agent, an x-ray imaging agent, a computed tomography (CT) imaging agent, a K-edge imaging agent, an ultrasound imaging agent, a photoacoustic imaging agent, an acoustic optical imaging agent, microwave imaging agent, a nuclear imaging agent, and combinations thereof.

The agent of interest is provided as a component of a reactive partner for reaction with an aldehyde of the formylglycine residue of the produced protein. A wide range of commercially available reagents can be used to attach an agent of interest to the formylglycine residue of the protein. For example, aminooxy, hydrazide, or thiosemicarbazide derivatives of a number of agents of interest are suitable reactive partners, and are readily available or can be generated using standard chemical methods.

Compositions

The present disclosure provides compositions, which in certain aspects are compositions useful in practicing the methods of the present disclosure.

In a first aspect, provided is a composition that includes a cell culture medium that includes an oxidation reagent compatible with cell culture, such as $Cu^{2+}$ and a cell present in the cell culture medium, where the cell express an FGE.

The $Cu^{2+}$ may be present in the cell culture medium at any desired concentration, including concentrations suitable for FGE activation. In certain aspects, the $Cu^{2+}$ is present in the cell culture medium at a concentration of from 1 nM to 100 mM, such as from 0.1 μM to 10 mM, from 0.5 μM to 5 mM, from 1 μM to 1 mM, from 2 μM to 500 μM, from 3 μM to 250 μM, from 4 μM to 150 μM, or from 5 μM to 100 μM (e.g., from 5 μM to 50 μM).

According to certain embodiments, the $Cu^{2+}$ is present in the cell culture medium at a concentration of 1 nM or more, 10 nM or more, 100 nM or more, 1 μM or more, 5 μM or more, 10 μM or more, 20 μM or more, 30 μM or more, 40 μM or more, 50 μM or more, 100 μM or more, 200 μM or more, 300 μM or more, 400 μM or more, 500 μM or more, 1 mM or more, 10 mM or more, or 100 mM or more. In certain aspects, the $Cu^{2+}$ is present in the cell culture medium at a concentration of 100 mM or less, 10 mM or less, 1 mM or less, 500 μM or less, 400 μM or less, 300 μM or less, 200 μM or less, 100 μM or less, 50 μM or less, 40 μM or less, 30 μM or less, 20 μM or less, 10 μM or less, 5 μM or less, 1 μM or less, 100 nM or less, 10 nM or less, or 1 nM or less.

The cell present in the cell culture medium may be a prokaryotic cell (e.g., an E. coli cell) a eukaryotic cell (e.g., a yeast cell, an insect cell, a mammalian cell, etc.). The cell present in the cell culture medium may include a nucleic acid template from which the FGE is expressed, and optionally, a nucleic acid template for expression of a protein that includes an FGE recognition site.

In certain aspects, the cell present in the cell culture medium is a mammalian cell selected from a CHO cell, a HEK cell, a BHK cell, a COS cell, a Vero cell, a Hela cell, an NIH 3T3 cell, a Huh-7 cell, a PC12 cell, a RAT1 cell, a mouse L cell, an HLHepG2 cell, an NSO cell, a C127 cell, a hybridoma cell, a PerC6 cell, a CAP cell, and a Sp-2/0 cell.

Also provided are cell-free compositions. In certain aspects, the cell-free compositions include an activated FGE and a buffer. For example, the activated FGE may be present in a buffer. Any activated FGE of interest may be included in the cell-free composition, including an activated FGE produced by any of the methods described herein for producing an activated FGE. According to certain embodiments, the activated FGE is a purified activated FGE which has been separated from a reaction mixture (e.g., an in vivo or cell-free protein synthesis reaction mixture, and FGE activation reaction mixture, etc.), e.g., by dialysis, buffer exchange, diafiltration, precipitation, ion exchange chromatography, affinity chromatography, electrophoresis, and/or the like.

A buffer suitable for maintaining the activated FGE in an activated form may be employed. In certain aspects, the buffer is suitable for providing a buffered aqueous solution having a pH range compatible with the activated FGE, such as a pH range from 5 to 9, or from 6 to 8, e.g., a pH of about 7, such as a pH of 7.4.

The cell-free compositions of the present disclosure may further include a protein that includes an FGE recognition site. Any protein of interest having an FGE recognition site may be present in the cell-free composition, including any of the proteins described herein above in the section relating to proteins that include FGE recognition sites, e.g., an antibody or antibody fragment of interest having an FGE recognition site, etc.

Kits

Aspects of the present disclosure further include kits. Kits according to certain embodiments of the present disclosure find use in practicing the methods of the present disclosure.

According to one embodiment, provided is a kit that includes an activated FGE, and instructions for using the activated FGE to convert a cysteine residue or a serine residue present in an FGE recognition site of a protein to a formylglycine residue. Such kits may further include a buffer for use in preparing a reaction mixture in which the activated FGE may be used to convert a cysteine residue or a serine residue present in an FGE recognition site of a protein to a formylglycine residue. The FGE and the buffer may be provided in the same or different containers (e.g., tubes). A protein (e.g., an antibody or any other protein of interest) that includes a recognition site for the activated FGE may also be included in the kit.

Also provided are kits that include a nucleic acid that encodes an FGE, and an oxidation reagent. In certain aspects, the nucleic acid that encodes an FGE is an expression vector suitable for expressing the FGE in a prokaryotic or eukaryotic (e.g., mammalian) cell upon transformation or transfection of the vector into the cell. The oxidation reagent may be any suitable oxidation reagent for activating the FGE, including any of the oxidation reagents described above in the sections relating to the methods of the present disclosure. In certain aspects, the oxidation reagent is $Cu^{2+}$. The kit may further include cells (e.g., any of the prokaryotic or eukaryotic cells described herein) suitable for expressing the FGE encoded by the nucleic acid. Instructions, e.g., for activating the FGE with the oxidation reagent and/or transforming or transfecting a cell type of interest with the nucleic acid, may be included in the kit.

Components of the kits of the present disclosure may be present in separate containers, or multiple components may be present in a single container.

In addition to the above-mentioned components, a kit of the present disclosure may further include instructions for using the components of the kit, e.g., to practice the methods of the present disclosure. The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g., CD-ROM, Blu-Ray, Hard Disk Drive (HDD), computer readable memory (e.g., flash drive), etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

The following examples are put forth so as to provide those of ordinary skill in the art with a complete disclosure and description of how to make and use embodiments of the present disclosure, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. By "average" is meant the arithmetic mean. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

EXAMPLES

Equipment

Micropipettors (calibrated annually): ResearchPlus 2.5, 10, 20, 100, 200, 1000 (Eppendorf); Serological Pipettor: Pipettor Plus (Omega); Balances (Calibrated monthly): XS4001S, NewClassic MF (ML204), AT200 (Mettler Toledo); pH measurement (calibrated monthly): SevenCompact (Mettler Toledo), InLab Expert Pro electrode (Mettler Toledo), Orion Standards (Thermo Scientific); SDS-PAGE: PowerPac Basic (Bio-Rad), Mini-PROTEAN® Tetra System (Bio-Rad); PAGE gel imaging: Image Quant LAS 4000 (GE Healthcare); Well plate washer: ELx405 (BioTek); Well plate reader: SpectraMax M5 (Molecular Devices); Centrifuges: Sorvall RC 6 Plus (Thermo Scientific), 5415 R & 5810 R (Eppendorf); Reaction mixer: Thermomixer R (Eppendorf), Vortexer: vortex genie 2 (Scientific Industries); Shakers: Lab Companion SI-600R (JEIO Tech Co. Ltd.), Shaking Incubator (Shel Labs); PCR cycler: Mastercycler Pro (Eppendorf); sterilization: Hiclave (Hirayama).

Absorption Spectroscopy

UV and visible absorption spectra were recorded on a NanoDrop™ 2000 (Thermo Scientific) spectrophotometer with manufacturer-supplied software, or on a GENESYS™ 10S spectrophotometer (Thermo Scientific) controlled with VISIONlite™ software. Spectrometers were calibrated with NIST-traceable potassium dichromate standards for photometric accuracy (Starna Scientific and Thermo Scientific).

Reversed-phase HPLC

Reversed-phase High Performance Liquid Chromatography was performed on an 1100/1200 series instrument (Agilent Technologies) controlled with Agilent OpenLAB CDS Chemstation Edition. The instrument included an in-line solvent degasser, analytical quaternary pump, vial auotsampler, thermostatted column compartment, and diode array detector. Chromatography was achieved on an Aeris™ core-shell 250×2.1 mm XB-C18 Widepore column (Phenomenex, Inc.). Area under the curve (AUC) was calculated with Chemstation (Agilent).

LC/MS

Mass Spectrometry data were collected on a 4000 QTRAP® mass spectrometer (AB Sciex) with an 1100 series HPLC (Agilent Technologies) that included an inline solvent degasser, analytical binary pump, and a thermostatted vial/wellplate autosampler. Chromatography was performed on a Jupiter™ 150×1.0 mm C18 column (Phenomenex, Inc.) enclosed in a butterfly column heater set to 65° C. with a PST-CHC controller (Phoenix S&T). Calculation of LC-MRM (multiple reaction monitoring)/MS transition masses and integration of the resulting data was performed with Skyline 2.6.

FPLC

Fast Performance Liquid Chromatography was performed on a GE

Healthcare Akta Protein Purification System consisting of the UPC-900, P-900 and Frac-950 modules. Nickel affinity chromatography was performed with a HisTrap® Excel 5 mL column (GE Healthcare). Gel filtration was performed by hand with disposable Sephadex® G-25 columns (GE Healthcare).

ICP-MS

Inductively-coupled plasmon mass spectrometry (ICP-MS) was performed by the Catalent Center for Excellence in Analytical Services (Morrisville, N.C.). The ratio of copper and calcium were calculated as a mol ratio based upon protein concentrations measured from 280 nm absorption intensity of enzyme stock solutions (Table 3).

Competitive Enzyme-linked Immunosorbent Assay (ELISA) Assessment of Antibody Affinity ELISA plates (Maxisorp) were coated with 1 μg/mL of His-tagged CD22 (Sino Biological 11958-H08H) at 1 μg/mL in PBS for 16 h. at 4° C. The plate was then washed four times with PBS 0.1% Tween-20 (PBS-T), and then blocked with 200 μL ELISA blocker (Thermo). In a second plate, an 11-point standard curve was prepared from serial 3-fold dilutions (50 μL+100 μL) of a stock solution of the competitor antibody at 20 μg/mL into ELISA blocker. Next, biotin-tagged CD22 (100 μL of 10 ng/mL) was added at to all of the wells. Finally, the mixture of competitor and biotin-tagged CD22 was transferred to the coated ELISA plate (100 μL/well), which was incubated at RT for 1-2 h with shaking. The final concentration of biotin-tagged CD22 was 5 ng/mL and the highest concentration of the competitor was 10 μg/mL. The plate was washed four times with PBS-T; then, 100 μL of a 1:10,000 dilution (into blocking buffer) of Streptavidin-HRP (Thermo 21130) was added and the plate was incubated at RT with shaking for 1-2 h. Next, the plate was washed four times with PBS-T, and developed with 1-Step Ultra TMB (100 μL/well, Pierce #34038). The reaction was quenched with 50 μl 2 M sulfuric acid, and absorbance was measured at 450 nm. $EC_{50}$ values were determined by nonlinear regression.

Estimation of Uncertainty

When displayed on bar graphs, measurements of uncertainty represent 95% confidence intervals calculated from the standard error of the mean for a sample size (n) of three or more using the following equation:

$$\text{error} = 1.96 \times \left(\frac{s}{\sqrt{n}}\right)$$

where s is the measured standard deviation for n samples. Errors reported for the enzyme kinetic parameters represent the estimate of error calculated from the minimized sum of squares found during nonlinear regression of activity data to the Michaelis-Menten equation:

$$y = \frac{E_t \cdot k_{cat} \cdot x}{(K_M + x)}$$

TABLE 3

FGE preparations contain both copper and calcium as measured by ICP-MS.

| Preparation | [Protein] (μM)* | Ca (μg/L) | Ca (μM) | Ca (ratio) | Cu (μg/L) | Cu (uM) | Cu (ratio) |
|---|---|---|---|---|---|---|---|
| Sc-FGE | 131.4 | 375 | 373.75 | 2.84 | 111 | 1.74 | 0.01 |
| Hs-cFGE | 204.3 | 98 | 97.4 | 0.48 | 4368 | 68.73 | 0.34 |
| Sc-FGE +Cu | 64.5 | 55 | 54.99 | 0.85 | 4768 | 75.03 | 1.16 |
| Hs-FGE +Cu | 69.7 | 106 | 105.59 | 1.51 | 6112 | 96.18 | 1.38 |

*Protein concentrations were measured using the absorption at 280 nm of stock protein solutions. Extinction coefficients for protein were calculated from the primary sequence of the enzyme using the analysis tools on the ExPASy bioinformatics server. For Hs-cFGE, ε = 85,745 $M^{-1}$ $cm^{-1}$ and MW = 33,286 Da; for Sc-FGE, ε = 88,000 $M^{-1}$ cm−1 and MW = 37,432 Da.

where $E_t$ is the total enzyme in solution, and $k_{cat}$ and $K_M$ are the standard enzymatic parameters specified by the STRENDA commission. Units of enzyme specific activity are the katal, where 1 kat=1 mol·s$^{-1}$. Kinetic parameters were determined from nonlinear regression of [substrate] v. initial velocity using GraphPad prism.

Area under the curve (AUC) for HPLC runs was calculated by the Chemstation software using the "new exponential" algorithm and setting slope sensitivity of 1 mAU. Kinetic parameters were determined from nonlinear regression of [substrate] v. initial velocity using GraphPad Prism.

Software

All instrument data collection workstations were operated with PCs running Microsoft Windows OS and instrument control software as provided by the manufacturers. Data analysis was performed either on a PC running MS windows or an Apple iMac using OS×10.10. Linear and nonlinear regression was performed using Graph Pad Prism 6.0e. Integration of HPLC chromatograms was performed using OpenLAB CDS Chemstation Edition. Calculation of LC-MRM/MS transition masses and integration of the resulting data was performed with Skyline 2.6 (MacCoss Lab, University of Washington). Statistical calculations were performed with Microsoft Excel. Graphs and figures were prepared with Adobe Creative Suite. Rendering of protein crystal structures was performed with open source PyMOL 1.7.

Materials

Reagents, Materials, Chemicals, and Abbreviations

All water used was deionized 18 MΩ) was from a Milli-Q Integral 5 system (EMD Millipore). Commercially available chemicals were reagent grade (or higher, as indicated). Chemicals and materials were sourced as follows: Sigma-Aldrich—β-mercaptoethanol (βME), trifluoroacetic acid (TFA), methoxylamine hydrate, copper(II) sulfate pentahydrate, streptomycin sulfate, iodoacetamide (IAA); Acros—formic acid, triethanolamine (TEAM), dithiothreitol (DTT), glycerol, glucose, potassium phosphate monobasic, potassium phosphate dibasic; Fisher Scientific—imidazole, tyrptone, yeast extract, sodium chloride; Honeywell Burdick & Jackson—acetonitrile+0.1% TFA (HPLC grade), acetonitrile+0.1% formic acid (HPLC grade); Thermo Scientific—tris(carboxyethyl) phosphine, (TCEP), PageRuler Plus Protein Standard; Bio-Rad Laboratories—10× protein assay; IBI scientific—isopropylthiogalactoside (IPTG); Amresco—ampicillin sodium salt (USP); Roche diagnostics—cOmplete-mini EDTA-free protease inhibitor cocktail; EMD Millipore—BugBuster® Master Mix; Invitrogen—Ultracompetent *E. coli* BL21(DE3) cells.

Antibody Production

For antibody production, GPEx technology was used to generate bulk stable pools of antibody-expressing cells. Antibodies were purified from the conditioned medium using Protein A chromatography (MabSelect, GE Healthcare Life Sciences).

Peptide Synthesis

All peptide synthesis was performed on solid phase and purified to ≥95%.

Identification of Biological Materials

Sc-FGE—UniProt accession: Q9F3C7; PDB 2Q17.
Hs-FGE—UniProt accession: Q8NBK3; PDB 1Y1E.

Example 1

$Cu^{2+}$ Increases the Conversion Efficiency of FGE in Mammalian Cells In Vivo

The effect on conversion in the presence of $Cu^{2+}$ (copper sulfate) in the cell culture medium of mammalian cells expressing FGEs and proteins that include FGE recognition sites was investigated. CHO cells expressing a recombinant human FGE and recombinant αHER2 mAb (heavy and light chain in same cell) containing the FGE recognition sequence LCTPSR (SEQ ID NO:4) were cultured FortiCHO media with the CellBoost4 feed, Efficient Feed C, and Efficient Feed C, supplemented with glucose and/or galactose. FortiCHO media (Life Technologies), CellBoost4 (Thermo Scientific) feed and Efficient Feed C (Life Technologies).

A variety of conditions were tested, and the results are summarized below.

As shown in FIG. 1 (Panel A), $Cu^{2+}$ (50 μM Day 0) increased conversion in FortiCHO media with the CellBoost4 feed, Efficient Feed C, and Efficient Feed C+glucose. As shown in FIG. 1 (Panel B), $Cu^{2+}$ (50 μM Day 0) improved conversion in PF-CHO media with Efficient Feed C, including the addition of glucose or galactose.

Figure 2:
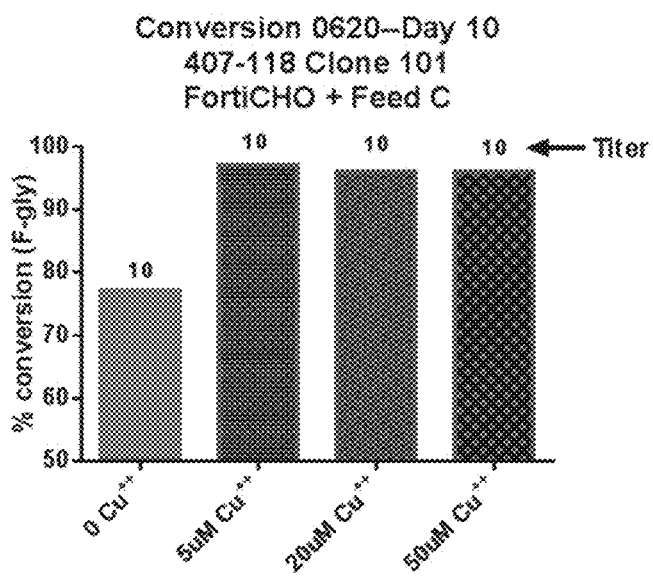
FIG. 2 provides data showing in vivo FGE activation/increased conversion in $Cu^{2+}$-treated cells according to certain embodiments of the present disclosure.

Addition of 5 μM or 20 μM $Cu^{2+}$ at Day 0 had the same effect on conversion as 50 μM, as shown in FIG. 2. Addition of 50 μM $Cu^{2+}$ at Day 3 or Day 5 had the same effect on conversion as addition on Day 0. $Cu^{2+}$ (50 μM D0) improved conversion under culture conditions that included PF-CHO, amino acids, AGT CD 5× medium, CellBoost4, glucose feed, and temperature shift.

The experiments described above demonstrated that culturing cells in the presence of $Cu^{2+}$ resulted in FGE activation and, in turn, increased conversion of the FGE recognition site in a target protein to include an FGly.

Experiments were also performed to test the effect on conversion in presence of various concentrations of other ion sources, such as iron(II) sulfate, $MnCl_2$, and $ZnCl_2$. The experimental conditions were the same as those used in the $Cu^{2+}$ experiments above. The results indicated that iron sulfate (0.1 mM or 0.5 mM Day 3), $MnCl_2$ (50 uM or 10 uM Day 0), and $ZnCl_2$ (50 uM Day 0) did not effect a detectable or significant increase in conversion of the target polypeptide.

Figure 3:
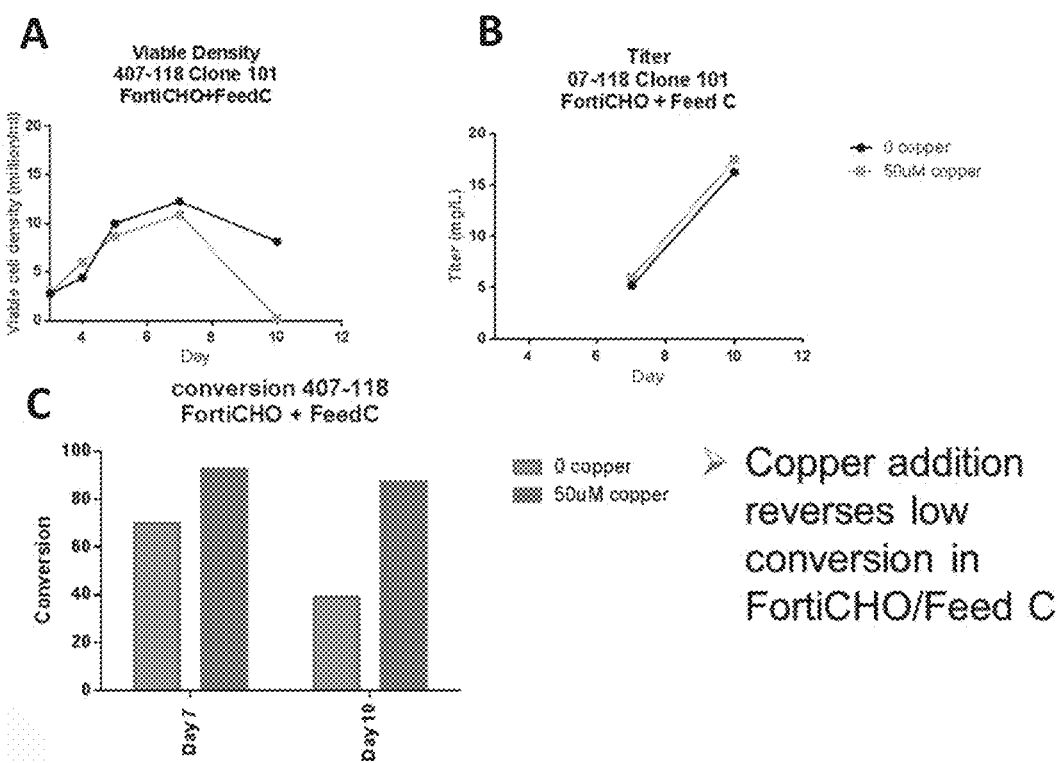
FIG. 3, Panel A shows data comparing the viable density of $Cu^{2+}$-treated cells and untreated cells.

FIG. 3, Panel A shows data comparing the viable density of $Cu^{2+}$-treated cells and untreated cells. FIG. 3, Panel B shows data comparing the protein titer of $Cu^{2+}$-treated cells and untreated cells. FIG. 3, Panel C shows data indicating in vivo FGE activation/increased conversion in $Cu^{2+}$-treated cells. The data shown in FIG. 3 indicate that the titer and cell viability does not significantly change in the presence of $Cu^{2+}$ as compared to experiments where no $Cu^{2+}$ was added.

Example 2

The Effect of Potential Stimulators of Lactate Consumption on Conversion Efficiency In Vivo As copper is a potential stimulator of lactate consumption, the ability of other potential stimulators of lactate consumption to activate FGE for increased conversion efficiency of the FGE recognition site in a target protein to include an FGly was investigated.

Experimental conditions were the same as those described in Example 1 above. Addition of lactate (Sigma) or pyruvate (Sigma) (1.5 g/L with feeds) to the cell culture medium did not increase conversion efficiency of the FGE. PowerFeedA (Lonza), reported to stimulate lactate consumption, did not increase conversion efficiency. Analysis of lactate levels showed no differences in lactate consumption in the presence or absence of $Cu^{2+}$, in spite of differences in conversion efficiency in the presence or absence of $Cu^{2+}$.

Figure 7:
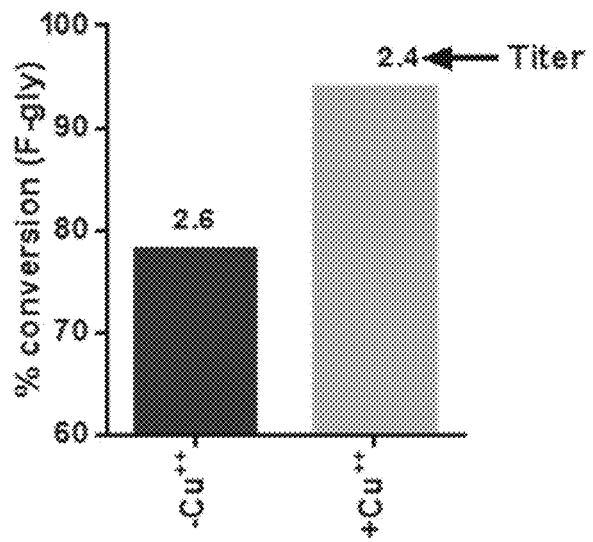
FIG. 7, Panel A shows a graph of % conversion in the presence of $Cu^{2+}$ or absence of $Cu^{2+}$ according to certain embodiments of the present disclosure.
Figure 7:
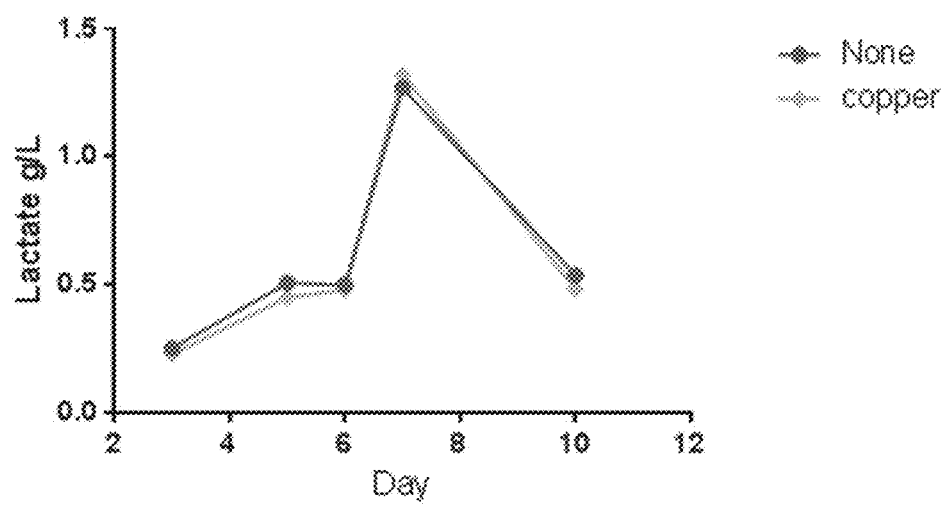

FIG. 7, Panel A shows a graph of % conversion in the presence of $Cu^{2+}$ or absence of $Cu^{2+}$, which indicated a higher % conversion in the presence of $Cu^{2+}$. FIG. 7, Panel B shows a graph of lactate consumption in the presence or absence of $Cu^{2+}$, which indicated no significant difference in lactate consumption in the presence or absence of $Cu^{2+}$. FIG. 7, Panel C shows a graph of glucose consumption in the presence or absence of $Cu^{2+}$, which indicated no significant difference in glucose consumption in the presence or absence of $Cu^{2+}$.

Example 3

$Cu^{2+}$ Reduces Variability in Conversion Efficiency in a 293 Expi System

A 293 Expi transient co-transfection system (Life Technologies) was used for producing antibodies having a form-ylglycine residue at a selected site. The system produced high antibody titers (100-500 mg/L) with variable (10-95%) conversion. To determine whether the addition of $Cu^{2+}$ in the culture medium could reduce the variability in this system, 50 µM copper sulfate was added just prior to transfection of CT-1.1 tagged Her2 or the day following transfection. Expi 293F that were treated with or without 50 µM copper sulfate prior to transfection were transiently co-transfected in three independent experiments with expression plasmids for full-length human FGE with an N-terminal KDEL (SEQ ID NO:7) amino acid sequence (+KDEL) and CT tagged antibody at a ratio of 3:1 antibody:FGE DNA. The culture was harvested at 5-6 days post transfection, titer assessed by ELISA, and the protein was purified and conversion was measured by mass-spectrometry.

Figure 4:
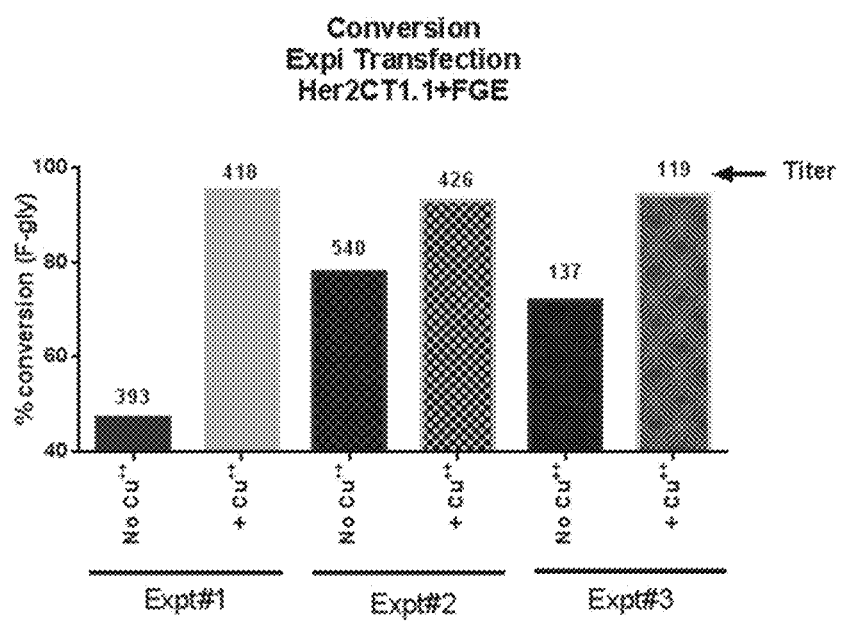
FIG. 4 provides data showing in vivo FGE activation/increased conversion in $Cu^{2+}$-treated cells according to an embodiment of the present disclosure.

The results are shown in FIG. 4 and Table 1 and indicate that $Cu^{2+}$ enhances conversion in 293 cells without a significant reduction in titer.

same experimental conditions as described above in Example 3, experiments were performed to determine the ability of $Cu^{2+}$ to reduce variability in conversion efficiency of non-KDEL forms of human FGE. Expi 293F cells that were treated with or without 50 µM copper sulfate prior to transfection were transiently co-transfected with expression plasmids for various forms of human FGE (+KDEL, WT, myc-His) and CT tagged antibody at a ratio of 3:1 antibody: FGE DNA. The culture was harvested at 5 days post transfection, titer assessed by ELISA, the protein was purified and conversion was measured by mass-spectrometry.

Figure 8:
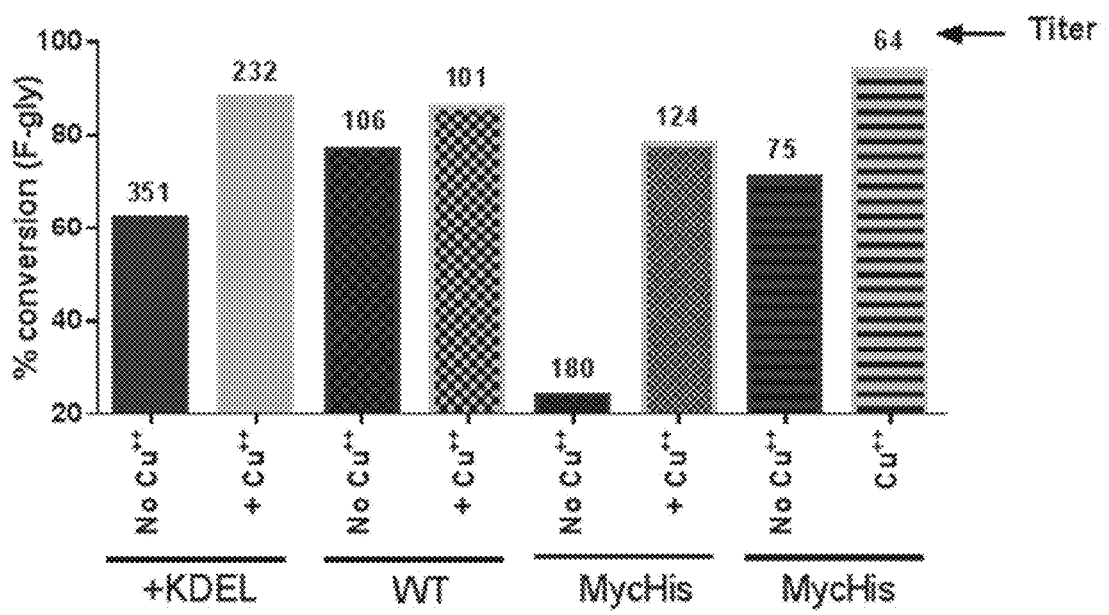
FIG. 8 provides data showing a reduced variability in conversion efficiencies for in vivo FGE activation in $Cu^{2+}$-treated cells according to an embodiment of the present disclosure.

The results are shown in FIG. 8 and Table 2 and indicated that $Cu^{2+}$ reduced variability in conversion efficiency in the Expi system when non-KDEL forms of human FGE were co-transfected with tagged antibody, specifically WT FGE and FGE C-terminally tagged with myc-His.

TABLE 2

| Experiment | FGE form | Copper sulfate (µM) | Antibody | Titer (mg/L) | Harvest day | Conversion (%) |
| --- | --- | --- | --- | --- | --- | --- |
| Exp. 1 | +KDEL | 0 | Her2 CT1.1 | 351 | 5 | 62 |
|  | +KDEL | 50 µM at Day 0 | Her2 CT1.1 | 232 | 5 | 88 |
|  | WT | 0 | Her2 CT1.1 | 106 | 5 | 77 |
|  | WT | 50 µM at Day 0 | Her2 CT1.1 | 101 | 5 | 86 |
|  | myc His | 0 | Her2 CT1.1 | 180 | 5 | 24 |
|  | myc His | 50 µM at Day 0 | Her2 CT1.1 | 124 | 5 | 78 |
| Exp. 2 | myc His | 0 | Her2 CT1.1 | 75 | 5 | 71 |
|  | myc His | 50 µM at Day 0 | Her2 CT1.1 | 64 | 5 | 94 |

Example 5

Effect of Stimulators and Inhibitors of Oxidative Phosphorylation on Conversion

Experiments were performed to determine the effect of stimulators and inhibitors of oxidative phosphorylation on conversion efficiency for human FGE, as compared to $Cu^{2+}$.

Dichloroacetate (DCA) is a pyruvate dehydrogenase kinase inhibitor that stimulates mitochondrial respiration. Rotenone is a mitochondrial complex 1 inhibitor and inhibits oxidative phosphorylation. A dose response for ATP production with both agents (4 hour treatment) was performed and confirmed that each drug affected ATP production as expected. Several experiments were run treating cells with DCA at several concentrations (DCA: 0 µM; 16 µM; 80 µM; 400 µM; 2000 µM; 10,000 µM; and 50,000 µM) and treating cells with $Cu^{2+}$ (copper sulfate) and rotenone (Rotenone: 0 nM; 5 nM; 24 nM; 120 nM; 600 nM; 3000 nM; and 15,000 nM) at several concentrations. Cells were plated and 10 µL of DCA or rotenone was added for a 4 hour treatment. Cells were equilibrated to room temperature 100 µL/well of Cell titerglo reagent (Promega) was added to each well. The plates were shaken of 2 min, incubated at room temperature for 10 min, and then read on a plate reader.

TABLE 1

| Experiment | FGE form | Copper sulfate (µm) | Antibody | Titer (mg/L) | Harvest day | Conversion (%) |
| --- | --- | --- | --- | --- | --- | --- |
| Exp. 1 | +KDEL | 0 | Her2 CT1.1 | 393 | 5 | 47 |
|  | +KDEL | 50 µM at Day 0 | Her2 CT1.1 | 418 | 5 | 95 |
| Exp. 2 | +KDEL | 0 | Her2 CT1.1 | 540 | 5 | 78 |
|  | +KDEL | 50 µM at Day 0 | Her2 CT1.1 | 426 | 5 | 93 |
| Exp. 3 | +KDEL | 0 | Her2 CT1.1 | 137 | 6 | 72 |
|  | +KDEL | 50 µM at Day 0 | Her2 CT1.1 | 119 | 6 | 94 |

Example 4

$Cu^{2+}$ Reduced Variability in Conversion Efficiencies of Various Forms of FGE Variable conversion efficiency of the +KDEL form of human FGE may be reduced by addition of $Cu^{2+}$. Using the The results indicated that there was no effect on conversion with either DCA or rotenone. The DCA treated cells exhibited slightly lower conversion than untreated cells, and cells treated with rotenone and $Cu^{2+}$ had similar conversion efficiencies as cells treated with $Cu^{2+}$ alone. These results indicated that oxidative phosphorylation was likely not involved in the enhanced conversion observed with $Cu^{2+}$ treatment.

Example 6

Effect of Sulfide Quinone Reductase (SQR) on Conversion

Hydrogen sulfide ($H_2S$) is a putative side product of the FGE catalytic cycle. Sulfide quinone reductase (SQR) is a mitochondrial enzyme that oxides and detoxifies $H_2S$. Experiments were performed to determine whether $H_2S$ accumulation over the course of the fed batch inhibited human FGE activity, and if $Cu^{2+}$ counteracted this effect.

Cells were plated. DNA was mixed with Optipro serum free medium (Life Technologies). FreeStyle Max transfection reagent (Life Technologies) and Optipro serum free medium were mixed. DNA and reagents were combined for 10-20 min at room temperature. The resulting complexes were added the cells.

A Western blotting was performed on lysates from cells treated with $Cu^{2+}$ or not treated with $Cu^{2+}$, using antibodies against SQR to determine whether $Cu^{2+}$ increased the levels of SQR. No significant difference in the levels of SQR was observed. Experiments were also performed to test whether overexpression of SQR in Expi cells could be a substitute for $Cu^{2+}$ in increasing conversion. The results indicated that there was no significant difference in conversion in SQR overexpressing cells compared to the control. SQR overexpression was confirmed in a CHO transient transfection. Thus, SQR is not likely involved in maintaining high conversion in the stationary phase.

Example 7

FGE Isolated from $Cu^{2+}$-treated Cells has Increased Specific Activity

To determine whether the enhanced conversion observed in $Cu^{2+}$ treated cells was due to increased specific activity of the FGE enzyme, Expi cells were treated with and without $Cu^{2+}$ and transfected with human FGE-mycHis (pRW529). FGE was purified via nickel chromatography and tested for specific activity, with the FGE isolated from $Cu^{2+}$ treated cells consistently exhibiting significantly higher activity. Experimental conditions were the same as in Example 3 above. Specific activity was measured as described in Example 9 below.

Figure 9:
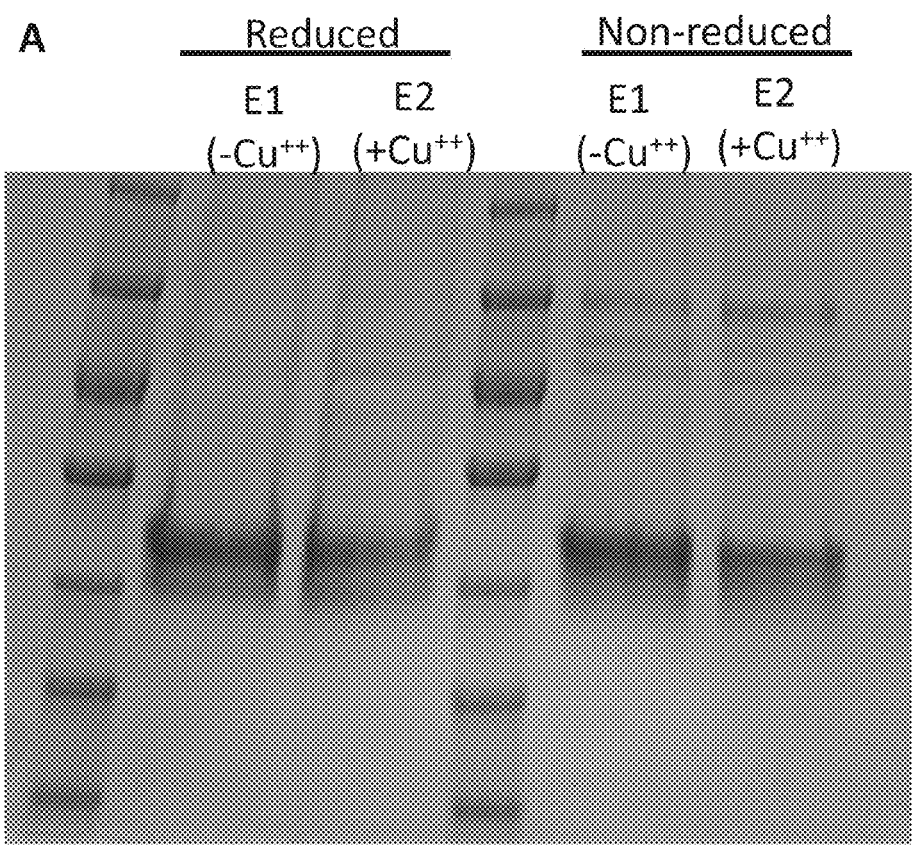
FIG. 9, Panel A, and FIG. 9, Panel B, provide data showing that providing $Cu^{2+}$ in the cell culture medium resulted in similar levels of FGE but the activity of FGE from copper cultures was significantly higher, according to certain embodiments of the present disclosure.
Figure 9:
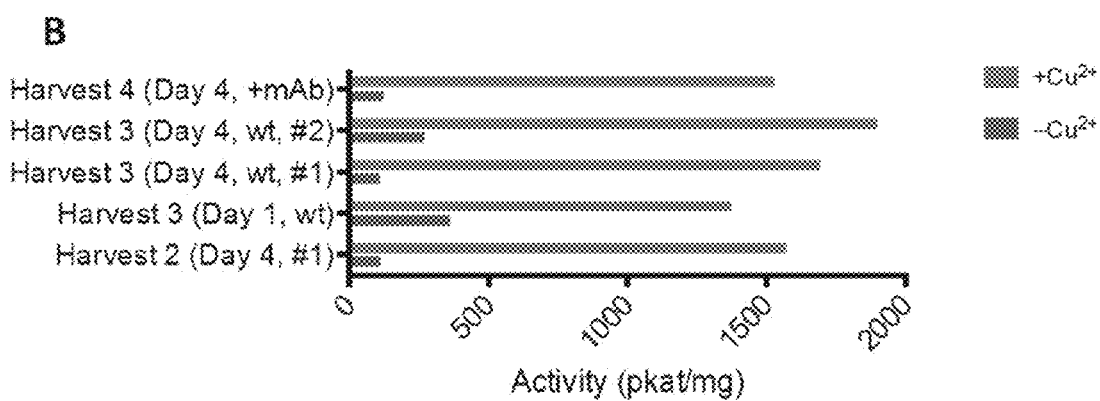

Providing $Cu^{2+}$ in the cell culture medium resulted in activation of the FGE, as indicated by the higher specific activity of FGE isolated from the treated cells as compared to cells cultured in the absence of copper but otherwise under identical conditions. As shown in FIG. 9, Panel A, and FIG. 9, Panel B, levels of FGE were the same (or lower with copper; see FIG. 9, Panel A) but the activity of FGE from copper cultures was significantly higher (see FIG. 9, Panel B).

Example 8

FGE Activation and Enhanced Conversion in Prokaryotic Cells

The ability of $Cu^{2+}$ to activate FGE and enhance conversion in prokaryotic cells was investigated. *E. coli* cells that co-express *S. coelicolor* ("Sc") FGEs and proteins that include FGE recognition sites were cultured in the presence or absence of $Cu^{2+}$. As shown in FIG. 4, conversion was enhanced in the cells treated with $Cu^{2+}$ as compared to the cells cultured in the absence of $Cu^{2+}$.

Figure 5:
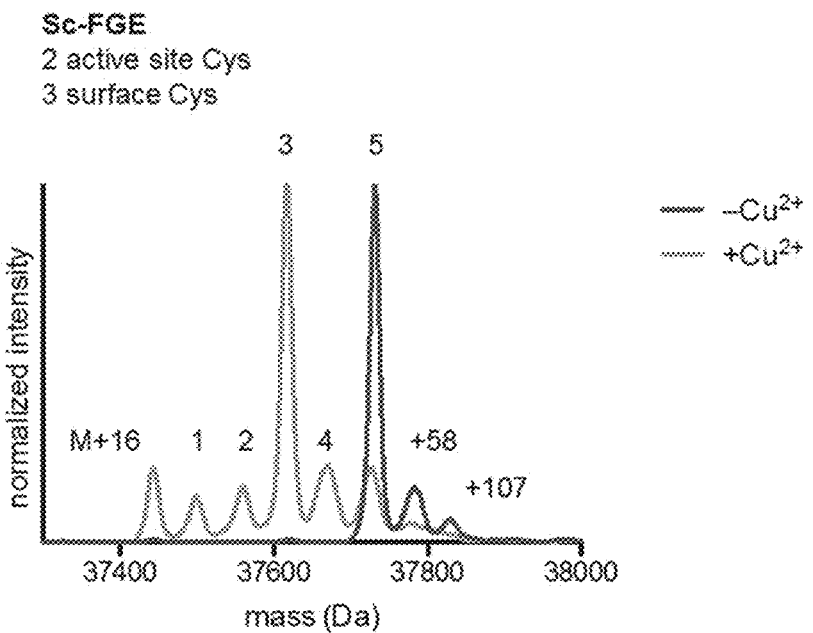
FIG. 5 provides liquid chromatography-mass spectrometry data comparing FGEs isolated from $Cu^{2+}$-treated E. coli cells and untreated E. coli cells.

To investigate the potential mechanism of FGE activation by $Cu^{2+}$, liquid chromatography-mass spectrometry (LCMS) was carried out on Sc-FGEs isolated from *E. coli* cells cultured in the presence or absence of $Cu^{2+}$. As shown in FIG. 5, $Cu^{2+}$ treatment resulted in the oxidation of the two active site thiol groups of the Sc-FGEs, indicating that FGE activation may involve disulfide formation involving the two active site cysteine residues.

Example 9

In Vitro FGE Activation

The present example demonstrates that FGEs may be activated in vitro by treatment with $CuSO_4$, resulting in treated/activated FGEs having greater specific activity as compared to untreated/non-activated FGEs.

Recombinant Expression and Purification of Sc FGE from *E. coli* Cells

Enhanced recombinant expression and purification of *S. coelicolor* (Sc)

FGE was performed. A pET151-D/TOPO vector encoding the wild-type Sc-FGE carrying an N-terminal hexahistidine tag and TEV protease cleavage site was transformed by heat shock at 42° C. into 50 µL ultracompetent *E. coli* BL21 (DE3) cells in LB medium. After plating and overnight growth on LB/agarose at 37° C. under ampicillin selection, individual colonies were amplified to 125 mL in terrific broth (TB). At OD 0.4-0.5, IPTG was added to reach 1 mM. The culture flasks were cooled to 18° C. and shaken at 200 RPM for 16 h. Cells were collected at 6,000 rcf for 20 min. Cells were resuspended in lysis buffer (25 mM triethanolamine, 50 mM NaCl, protease inhibitors, pH 8.0) and lysed with BugBuster® lysis reagent. The solutions were clarified by centrifugation at 25,000 rcf for 25 min. Residual DNA was precipitated by diluting the supernatant into a solution of streptomycin sulfate, reaching a final concentration of 1% w/v. The solution was stirred for 15 min at 4° C., and then centrifuged for 25,000 RPM for 25 min. The supernatant was loaded onto a Ni-NTA sepharose FF column and eluted under gravity flow. Nonspecifically bound protein was removed by washing with 5 CV of wash buffer (25 mM triethanolamine, 250 mM NaCl, 10 mM imidazole, pH 8). The purified protein was isolated with elution buffer (25 mM triethanolamine, 250 mM NaCl, 300 mM imidazole, pH 8). Fractions containing protein (as judged by Bradford assay) were pooled and loaded onto a Sephadex® G-25 column (PD-10, GE Healthcare) equilibrated with storage buffer (25 mM triethanolamine, 50 mM NaCl, 8% v/v glycerol, pH 7.4). The protein was then eluted with storage buffer, concentrated with a 10 kD Amicon® ultrafiltration membrane (Millipore, Inc.), and flash frozen at 77 K. Typical yield of isolated enzyme: 50-75 mg/L media. Purified enzyme was characterized by SDS-PAGE electrophoresis (10% gel, Bio-Rad, Inc.), reversed-phase HPLC, LCMS of the intact globular protein, LCMS of a tryptic digest of the enzyme, UV-Vis absorption spectroscopy, specific activity (as described below).

FGE Activity Assay

The specific activity of FGE was measuring using a discontinuous enzymatic activity assay. The substrate for FGE was a 14 amino acid peptide containing the consensus sequence (H2N-ALCTPSRGSLFTGR-COOH (SEQ ID NO:8)). The rate of reaction was determined by integrating the peak area at 215 nm of the starting material (Cys) and product (fGly) containing peptides on reversed-phase HPLC. The identity of product (and side product) peaks were determined by RP-HPLC MS/MS. Each aqueous reaction solution (60 µL) contained substrate peptide (100 µM), FGE (1 µM), DTT (1 mM), and buffer (25 mM triethanolamine, pH 9). A single time course consisted of 5 data points collected every 2 minutes. The reaction was initiated upon addition of FGE stock solution and vortexing for 3 s. Time points were quenched by diluting 10 µL of reaction mixture into 1 µL of 1 M HCl by hand with a micropipettor. After completion of the reaction, each time point was analyzed by RP-HPLC.

Quantification of FGE Substrate and Product Peptides by HPLC

Substrate, product, and side products of the FGE substrate peptide ALCTPSRGSLFTGR (SEQ ID NO:8) were separated on RP-HPLC over 7 min with isocratic 18% MeCN in water containing 0.1% TFA. The integrated area of the fGly (2.1 min), Cys (3.3 min), βME-DS (3.6 min), and Cys-DS (6.2 min) forms of the substrate were used to calculate total area and each fraction thereof.

Activation of FGE

To a solution of formylglycine-generating enzyme (*S. coelicolor*, 50 µM) in buffered aqueous solution (25 mM triethanolamine, pH 7.4, 50 mM NaCl) was added copper(II) sulfate (100 µM). The mixture was vortexed at 1500 RPM for 1 h at 25° C. The protein was then removed from the reaction mixture by buffer exchange into 25 mM triethanolamine, pH 7.4, 50 mM NaCl using Sephadex® G-25 resin (GE healthcare PD-10 column following manufacturer's instructions). After exchange, the specific activity of FGE was measured using the standard activity assay described herein.

Results

Figure 6:
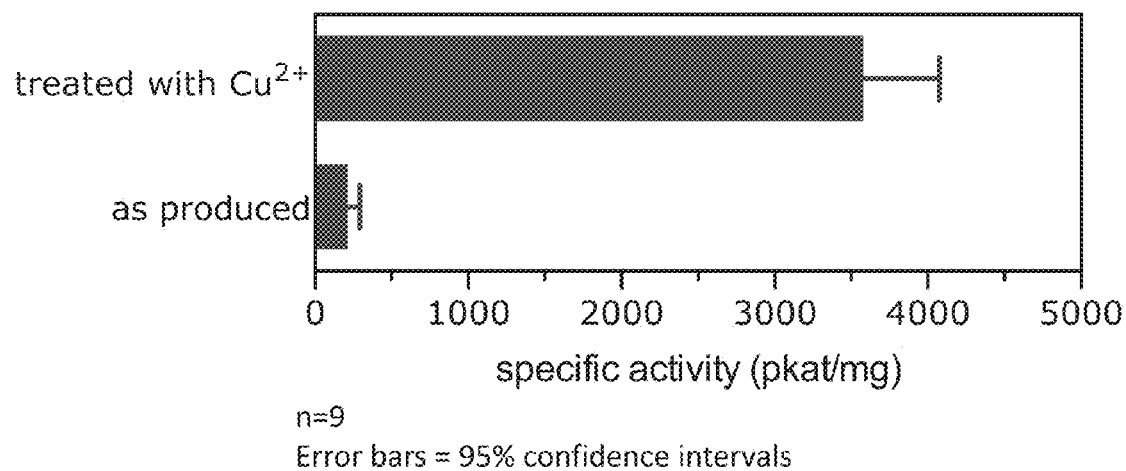
FIG. 6 shows data demonstrating in vitro activation of Sc FGE using $CuSO_4$, according to certain embodiments of the present disclosure.

The results of the in vitro activation experiment are shown in FIG. 6, which shows a graph of the specific activities of FGE treated with $CuSO_4$ as a source of $Cu^{2+}$, and untreated FGE. Treatment with $Cu^{2+}$ resulted in FGE activation, as indicated in this example by the increased specific activity of the treated FGE.

Example 10

Production of Recombinant Baculovirus Encoding for the Core of Human FGE

DNA encoding the catalytic "core" of *H. sapiens* FGE followed by a C-terminal $His_6$ tag for purification (Hs-cFGE) was amplified from a previous construct (see Rabuka, et al., *Nat. Protocols*., (2012), 7, 1052-1067) by PCR. The Hs-cFGE sequence and primers are listed below. Preparation of the Hs-cFGE-encoding baculovirus was performed using the Bac-to-Bac baculovirus expression system (Invitrogen).

Primers Used for Cloning Hs-cFGE for the Bac-to-Bac Expression System.

```
Forward:
GAGGCTAACGCTCCGGGCCC          (SEQ ID NO: 9)

Reverse:
GTCCATAGTGGGCAGGCGGTC         (SEQ ID NO: 10)
```

The Bac-to-Bac baculovirus expression system results in an additional four residues at the N-terminal end to provide a signal sequence of amino acid sequence DRSL (SEQ ID NO:6). The primary sequence of Hs-cFGE as expressed from this expression vector is provided below.

| Primary sequence of Hs-cFGE with TEV protease site and $His_6$ tag |
|---|
| 10 20 30 40 |
| DRSLEANAPG PVPGERQLAH SKMVPIPAGV FTMGTDDPQI |
| 50 60 70 80 |
| KQDGEAPARR VTIDAFYMDA YEVSNTEFEK FVNSTGYLTE |
| 90 100 110 120 |
| VAAAPWWLPV KGANWRHPEG PDSTILHRPD HPVLHVSWND |
| 130 140 150 160 |
| AVAYCTWAGK RLPTEAEWEY SCRGGLHNRL FPWGNKLQPK |
| 170 180 190 200 |
| GQHYANIWQG EFPVTNTGED GFQGTAPVDA FPPNGYGLYN |
| 210 220 230 240 |
| IVGNAWEWTS DWWTVHHSVE ETLNPKGPPS GKDRVKKGGS |
| 250 260 270 280 |
| YMCHRSYCYR YRCAARSQNT PDSSASNLGF RCAADRLPTM |
| 290 |
| DKGENLYFQG HHHHHH (SEQ ID NO: 11) |

Example 11

Expression and Purification of Hs-cFGE from Hi5 Cells

Figure 10:
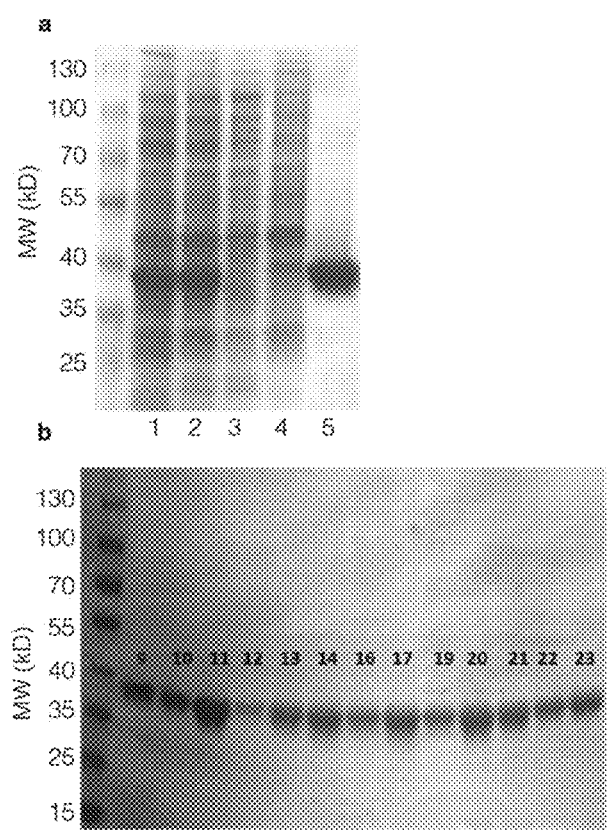
FIG. 10 shows images of purified FGE characterized by SDS-PAGE electrophoresis. Sc-FGE and Hs-cFGE preparations yielded enzyme in good quantity and purity.

Hs-cFGE baculovirus was transfected into Hi5 insect cells (Invitrogen) at an MOI of 0.1. After 72 h in culture, the conditioned media was clarified by centrifugation and filtration (0.45 µm PES), and loaded by FPLC onto HisTrap® Excel resin at 5 mL/min. The resin was washed with 10 column volumes (CVs) of wash buffer (25 mM TEAM, 250 mM NaCl, 5 mM calcium acetate, 10 mM imidazole, pH 8). The enzyme was then removed from the column with elution buffer (25 mM triethanolamine (TEAM), 5 mM calcium acetate, 300 mM imidazole, pH 8). Fractions containing protein (as determined by UV detection of the FPLC elution) were pooled and loaded onto a Sephadex® G-25 column equilibrated with storage buffer (25 mM TEAM, 8% v/v glycerol, pH 7.4). Then, the protein was eluted with storage buffer, concentrated with a 10 kD Amicon® ultrafiltration membrane (Millipore), and flash frozen in liquid nitrogen. The typical yield of isolated enzyme was 10-20 mg/L media. Purified enzyme was characterized by SDS-PAGE electrophoresis (FIG. 10), reversed-phase HPLC, LC/MS of the intact protein, tryptic digestion followed by LC-MS/MS, absorption spectroscopy, and specific activity (as described in the Examples below).

Example 12

Assay of FGE Catalytic Activity

The specific activity of FGE was measured using a discontinuous enzymatic activity assay. The substrate for FGE was a 14 amino acid peptide containing the CXPXR consensus sequence (ALCTPSRGSLFTGR (SEQ ID NO:8)). The rate of reaction was determined by integrating the peak areas at 215 nm of the substrate cysteine ($C_{sub}$) and product (fGly) peptides on reversed-phase HPLC. The identities of product (and side product) peaks were determined by RP-HPLC MS/MS (see below). Each aqueous reaction solution (120 μL) contained $C_{sub}$ (100 μM), FGE (0.1-1 μM), DTT (1 mM), and buffer (25 mM TEAM, pH 9). A single time course included 5 data points collected at evenly spaced intervals. The reaction was initiated upon addition of FGE stock solution and vortexing for 3 s. The reaction vial was vortexed at 1,500 RPM and 25° C. in a thermomixer R (Eppendorf). Time points were hand quenched by adding 20 μL of reaction mixture to 2 μL of 1 M HCl using a micropipettor. After completion of the reaction, each time point was analyzed by RP-HPLC (see below).

Example 13

Identification of FGE Peptide Intermediates by LC-MS/MS and RP-HPLC

Figure 11:
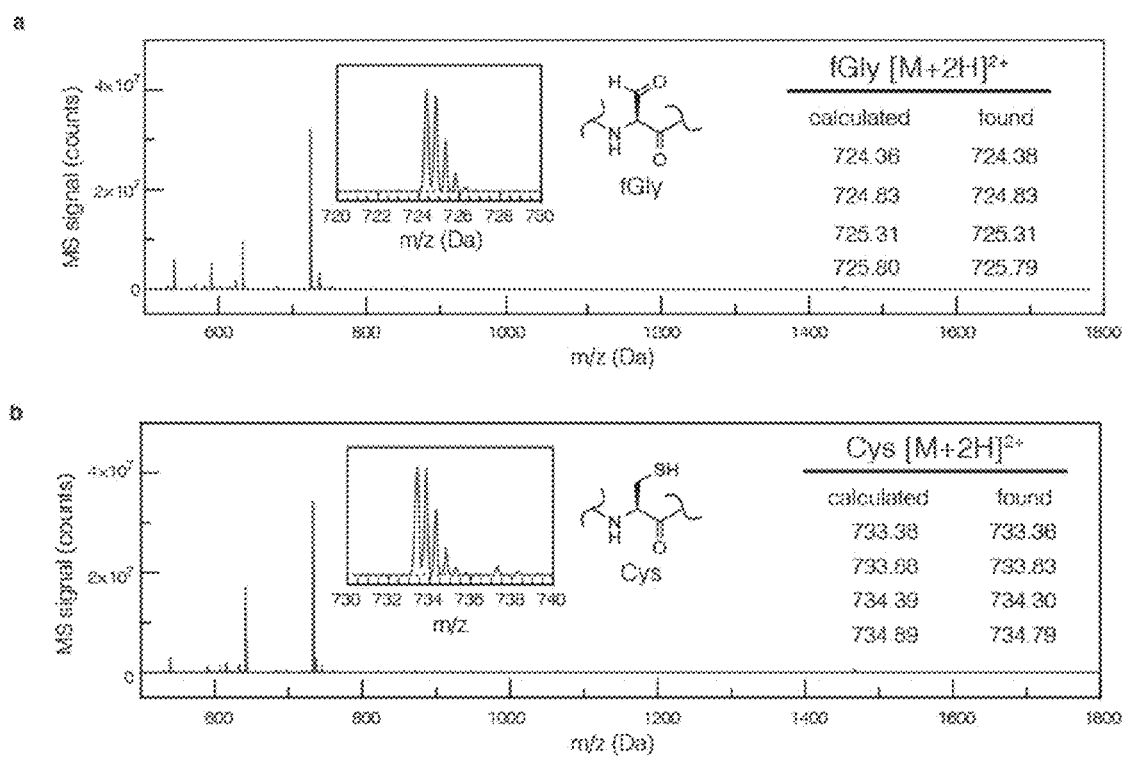
Figure 12:
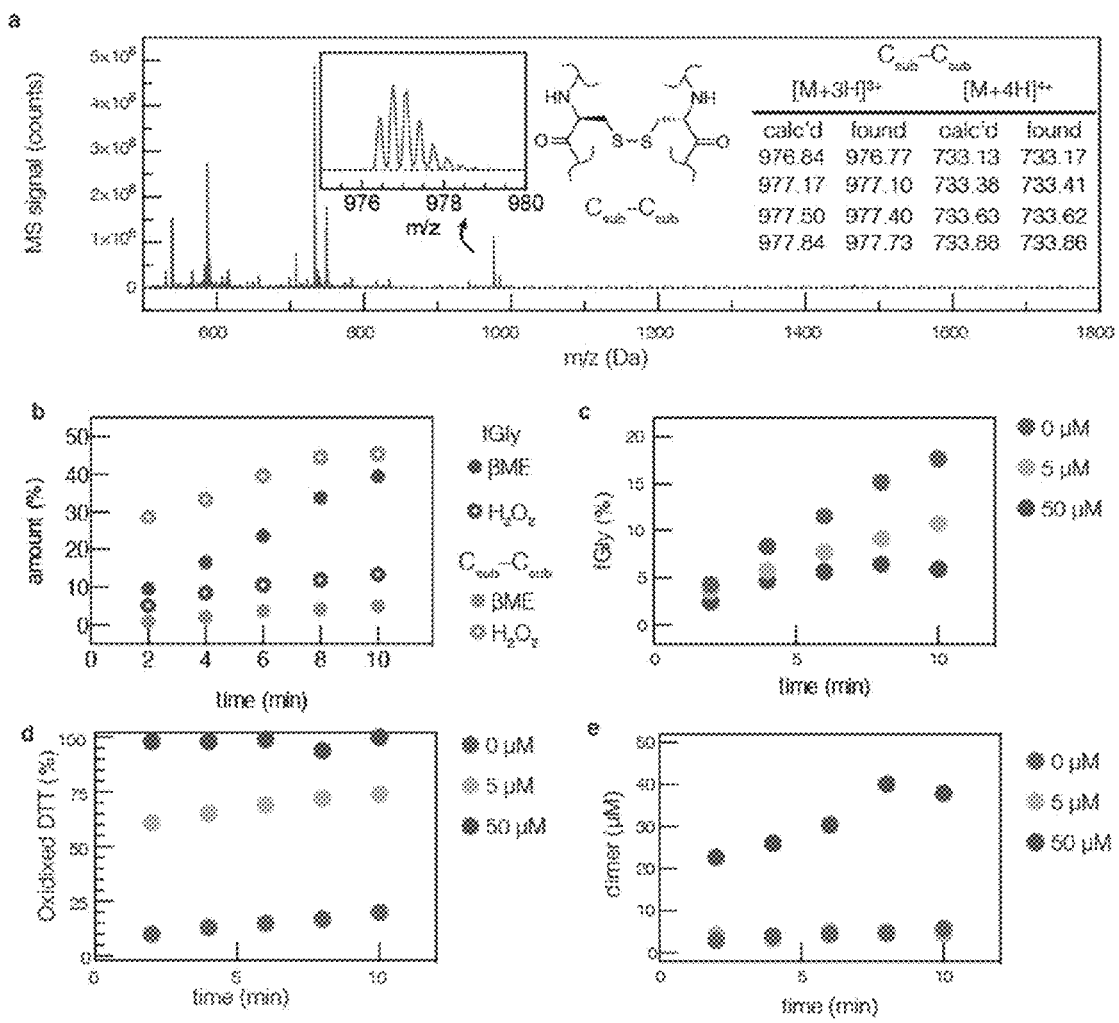
FIG. 12 shows graphs of reaction inhibition as a function of substrate dimerization.
Figure 13:
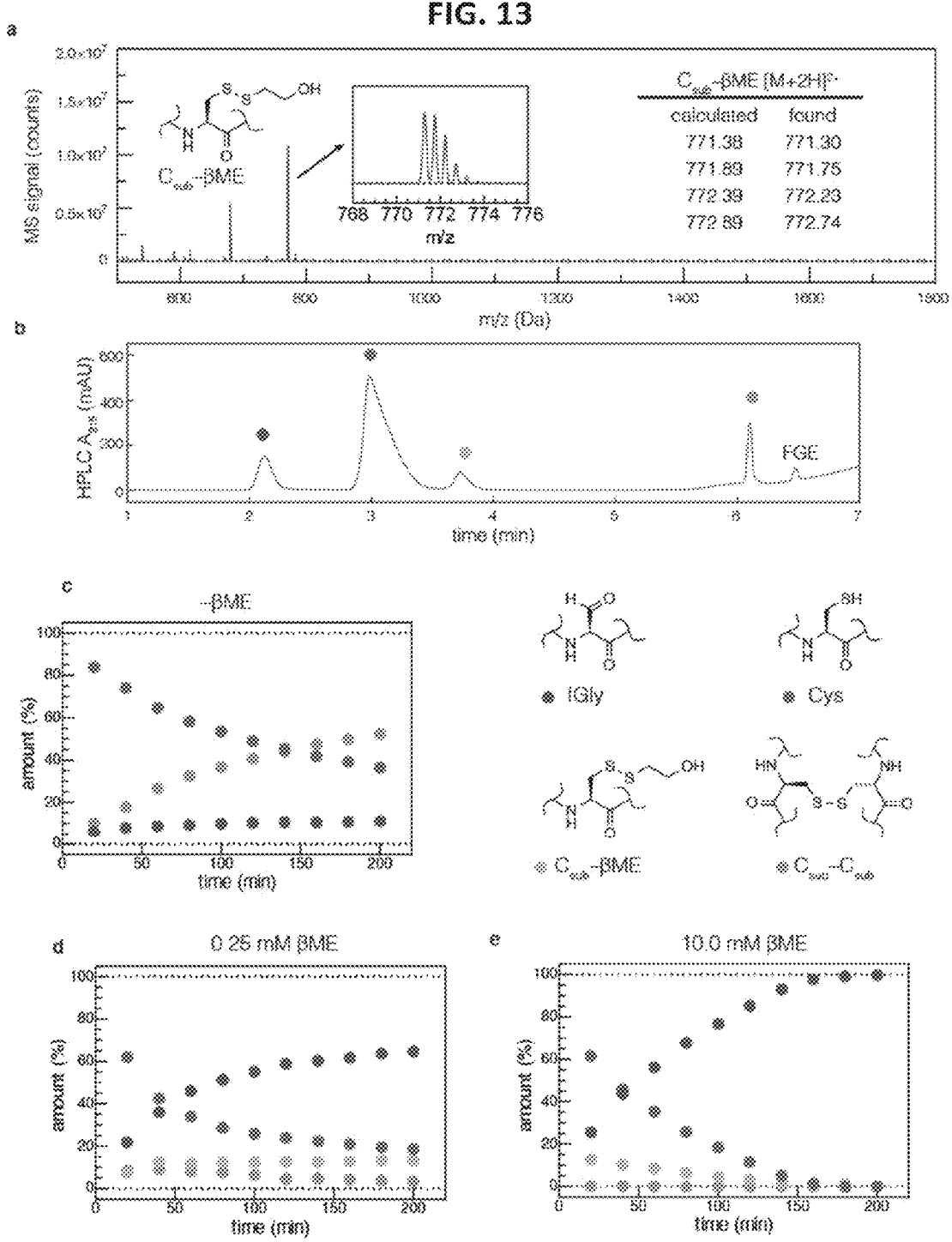
FIG. 13 shows data related to identification and monitoring of substrate disulfides formed by FGE.

To identify the intermediates and products of in vitro conversion by FGE on $C_{sub}$, reaction mixtures from the FGE activity assay were quenched and analyzed by LC/MS. The reaction mixture included 0.5 mM peptide, 0.5 μM human FGE, 5 mM 2-mercaptoethanol (βME), and 25 mM TEAM, pH 9 in a total volume of 200 μL. Time points were prepared by adding 20 μL of reaction mixture to 2 μL of 1 M HCl. The gradient was 5-25% MeCN in water with 0.1% formic acid over 10 minutes. The relative intensities and retention times of the four peptide peaks detected at 215 nm on RP-HPLC were replicated in the LC-MS/MS data, allowing assignment of each peak by mass. The calculated and observed m/z ions, and assignments for each peptide species, are shown in FIG. 11, FIG. 12, and FIG. 13.

Example 14

Quantification of FGE Substrate and Product Peptides by HPLC

Substrate, product, and side products of the FGE substrate peptide ALCTPSRGSLFTGR (SEQ ID NO:8) were separated on RP-HPLC over 7 min with isocratic 18% MeCN in water containing 0.1% TFA. The integrated areas of the fGly (2.1 min), $C_{sub}$ (3.3 min), the $C_{sub}$/βME disulfide ($C_{sub}$-βME, 3.6 min), and substrate/substrate disulfide ($C_{sub}$-$C_{sub}$, 6.1 min) forms of the substrate were used to calculate total area and each fraction thereof.

Example 15

Thiol and Disulfide Mapping of FGE

To determine the oxidation state of thiol residues on either Sc-FGE or Hs-FGE, a procedure was developed for mapping thiols and disulfides by LC/MS using sequential labeling, digestion, and orthogonal labeling. Step 1, initial labeling and tryptic digestion: the reaction mixture was composed of FGE (7.5 μg), NH$_4$HCO$_3$ (50 mM), iodoacetamide (20 mM), and trypsin (0.75 μg) in a total volume of 30 μL. The tube containing the sample was incubated at 37° C. for 16 h. Step 2, quenching: water (6 μL) and DTT (4.8 μL of 0.5 M, 50 mM final concentration) were added to the reaction mixture from step 1. The tube containing the sample was incubated at 37° C. and 1500 RPM for 1 h. Step 3, second labeling: N-ethylmaleimide (7.2 μL of 0.5 M, 150 mM final concentration) was added to the reaction mixture from step 2. The tube containing the sample was then incubated at 37° C. and 1500 RPM for 1 h. After step 3, the reaction mixture was quenched with HCl (4.8 μL of 1 M, 100 mM final concentration). Digested peptides were separated with a gradient of 0-50% MeCN in water with 0.1% formic acid over 15 min. Cysteine-containing peptides were detected by MRM/MS monitoring iodoacetamide, N-ethylmaleimide, and oxidative modifications of Cys residues.

Example 16

Activation of FGE with Copper(II) Sulfate

Copper sulfate (50 μM, 5 molar equiv) was added to a solution of Sc-FGE (100) in buffered aqueous solution (25 mM TEAM, pH 7.4, 50 mM NaCl). The mixture was vortexed at 1500 RPM for 1 h at 25° C. The protein was purified from the reaction mixture by buffer exchange into 25 mM TEAM, pH 7.4, 50 mM NaCl using Sephadex® G-25 resin. Then, the specific activity of FGE was measured using the activity assay described above.

Example 17

Quantification of fGly Content in Intact mAb

DTT (20 mM) was added to a solution of mAb (20 μg) in buffered aqueous solution (25 mM NH$_4$HCO$_3$) to a final volume of 20 μL. The tube containing the sample was incubated at 37° C. for 15 min at 1500 RPM. Then, HCl (50 mM) was added to the solution and the tube was vortexed until mixed. Next, ammonium bicarbonate (100 mM) was added to the solution and the tube was vortexed until mixed. Trypsin (1 μg) and iodoacetamide (50 mM) were added, and the tube was incubated at 37° C. and 1500 RPM for 60 min in the dark. Finally, sodium citrate (150 mM, pH 5.5) and methoxylamine (100 mM) were added to the solution, and the tube was incubated at 37° C. for 16 h. The processed sample was then analyzed by LC-MRM/MS. The MRM transitions included modifications of the Cys-containing peptide including: cysteine, cysteine modified with iodoacetamide, formylglycine, formylglycine hydrate (including loss of water in the collision cell), and formylglycine methyl oxime. The abundance of each species was defined by its 5 most intense precursor/product ion pairs, which were integrated to give the total signal and relative fractions of each component. In the optimized digestion and capping procedure described above, unreacted Cys, fGly, or fGly-hydrate above background was not detected, observing only carboxyacetamidomethyl Cys (CAM) and the methyl oxime of fGly (MeOx). Carboxyacetamidomethyl Cys (CAM) and the methyl oxime of fGly (MeOx) were detectable.

Example 18

In Vitro Conversion of Intact mAb with FGE

Hs-cFGE was added to a solution of IgG containing the aldehyde tag (where the C-terminal K was substituted with SLCTPSRGS (SEQ ID NO:12)) in 25 mM TEAM pH 9.0 with 50 mM NaCl and 1 mM βME. The enzyme was added at 10 mol % relative to the concentration of $C_{sub}$ within the aldehyde tag of the antibody heavy chain. The solution was vortexed at 1,000 RPM for 16 h at 18° C., and then the solution was quenched with 0.25 vol equiv of 0.5 M sodium citrate, pH 5.5 (to a final concentration 100 mM citrate) to decrease the pH of the solution to ~7 for binding to mAb Select protein A resin. The IgG was purified using standard methods. A typical reaction yielded a final fGly content in the antibody of 95-100%, corresponding to a reaction conversion yield of 90-100%. To date, the reaction has been performed across a range of scales from 20 μg to 0.6 g.

Example 19

Generation of FGE Apoenzyme

Ethylenediaminetetraacetic acid (EDTA, 15 mM) and tris(carboxyethyl)phosphine (TCEP, 15 mM) were added to a solution of Sc-FGE holoenzyme (5 μM) in buffered aqueous solution (25 mM TEAM, pH 7.4, 50 mM NaCl). The mixture was vortexed at 750 RPM for 1 h at 37° C. The protein was purified from the reaction mixture by buffer exchange into 25 mM TEAM, pH 7.4, 50 mM NaCl using Sephadex® G-25 resin. Then, the specific activity of FGE was measured using the activity assay described above.

Results

The results from Examples 10-19 are discussed in the following sections.

Sc-FGE and Hs-cFGE had modest catalytic activity as isolated from cell culture. Methods for recombinant expression of FGE were developed. FGEs from two species—S. coelicolor and H. sapiens—were selected for study because they represented both prokaryotic and eukaryotic forms of the enzyme. Sc-FGE was prepared by transfection of E. coli and purification from clarified cell lysates. Hs-cFGE was prepared in high purity and good yield by viral transduction of insect cells. The human form was produced in insect cells.

With respect to the human enzyme, a noncatalytic portion of the enzyme was removed that appeared to facilitate precipitation (described in detail below). With soluble enzyme, the activity of FGEs as produced from cell culture was evaluated, and the reaction conditions required for catalysis.

To measure the specific activity of FGE, a discontinuous assay was performed that used MALDI-MS to quantify the starting material and product of quenched reaction mixtures. In the assay, reversed-phase HPLC was used both to separate and to quantify the Cys and fGly forms of a peptide containing the FGE consensus sequence. The unmodified 14-amino acid peptide ALCTPSRGSLFTGR (SEQ ID NO:8) was used as a substrate for both the Sc- and Hs-forms of the enzyme.

The conversion of Cys to fGly used a 2 $H^+$/2 $e^-$ oxidation of the substrate Cys thiol as well as exchange of sulfur for oxygen. Current data support a mechanism in which molecular oxygen is the terminal electron acceptor. However, because $O_2$ is a 4 $H^+$/4 $e^-$ acceptor, a reducing agent was used to provide a second equivalent of 2 $H^+$ and 2 $e^-$, completing the reduction from $O_2$ to 2 mol $H_2O$. To test if one might be able to bypass use of a reductant by adding a 2 $H^+$/2 $e^-$ oxidant directly to the in vitro reaction, the oxidant $H_2O_2$ was added, but resulted in dimerization of the substrate by generating a disulfide (Csub-Csub), which halted the reaction (FIG. 12, panel a and FIG. 12, panel b). A mixture of reductant (DTT) and $O_2$ was used for routine activity measurements.

Figure 14:
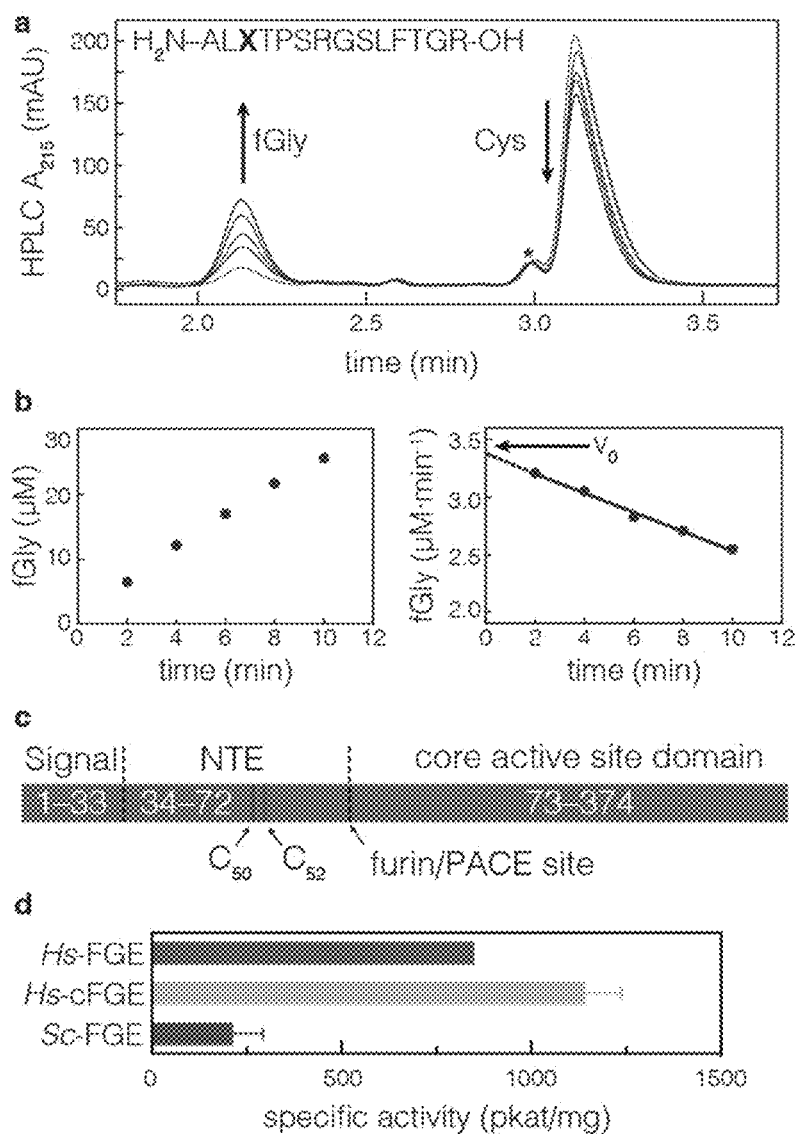
FIG. 14 presents data showing the specific activity of FGEs was measured using a discontinuous activity assay.

Individual FGE reactions were initiated by rapidly mixing FGE into a premixed buffered solution of $C_{sub}$ and reducing agent. It was assumed that all buffered solutions contained oxygen at ~270 μM at 25° C. (based upon Henry's law). Time points were chemically quenched by hand with HCl. As described below, the specific activity of FGE can vary as a function of the chemical state of its active site, and so enzyme concentrations in this assay spanned the range of 0.1-10 μM (0.1-10 mol %) enzyme. The identities of both the Cys- and fGly-containing peptides were confirmed by LC-MS/MS (FIG. 11). These assignments were then correlated with HPLC retention times (FIG. 14, panel a). The integrated peak areas of substrate and product were used to calculate the initial velocity of FGE (FIG. 14, panel b) using the method described by Boeker (*Biochem. J.*, (1984), 223, 15; and *Biochem. J.*, (1985), 226, 29).

Hs-FGE contains three primary domains: a signal peptide, an N-terminal extension (NTE), and a core that binds substrate and performs turnover (FIG. 14, panel c). After transport to the ER and proteolytic removal of the signal peptide, the "full length" wild-type enzyme (Hs-FGE) contains both the NTE and the core. The NTE may facilitate ER retention through disulfide bond formation between $C_{50}$ and/or $C_{52}$ with ERp44. The border between the NTE and the core is a proteolytic cleavage site for proprotein convertases such as furin and PACE. When FGE encounters these enzymes in the secretory pathway, the NTE is removed and the truncated core can be secreted. In vitro, the full-length FGE had a propensity to aggregate at high concentrations, and as such the truncated core (cFGE) was prepared. The specific activity of Hs-cFGE (1,143 pkat·mg$^{-1}$, 33.3 kD) was similar to Hs-FGE that contained the NTE (850 pkat·mg$^{-1}$, 36.9 kD). In addition, Sc-FGE expressed in E. coli had a significantly lower specific activity (214 pkat·mg$^{-1}$), relative to the human enzyme expressed in insect cells (FIG. 14, panel d). Thus, the experiments showed the production of active FGEs in good yield and high purity from both species. Further experiments were performed as described above to investigate the mechanism by which FGE performs catalysis and to enhance the activity of FGE.

In some instances, the activity of FGE depended upon the presence of a copper cofactor, and not the redox state of active site cysteine residues. Experiments were performed to test whether FGE requires the presence of an active site disulfide residue. Reduced and oxidized forms of FGE were prepared and their specific activities were measured.

Figure 15:
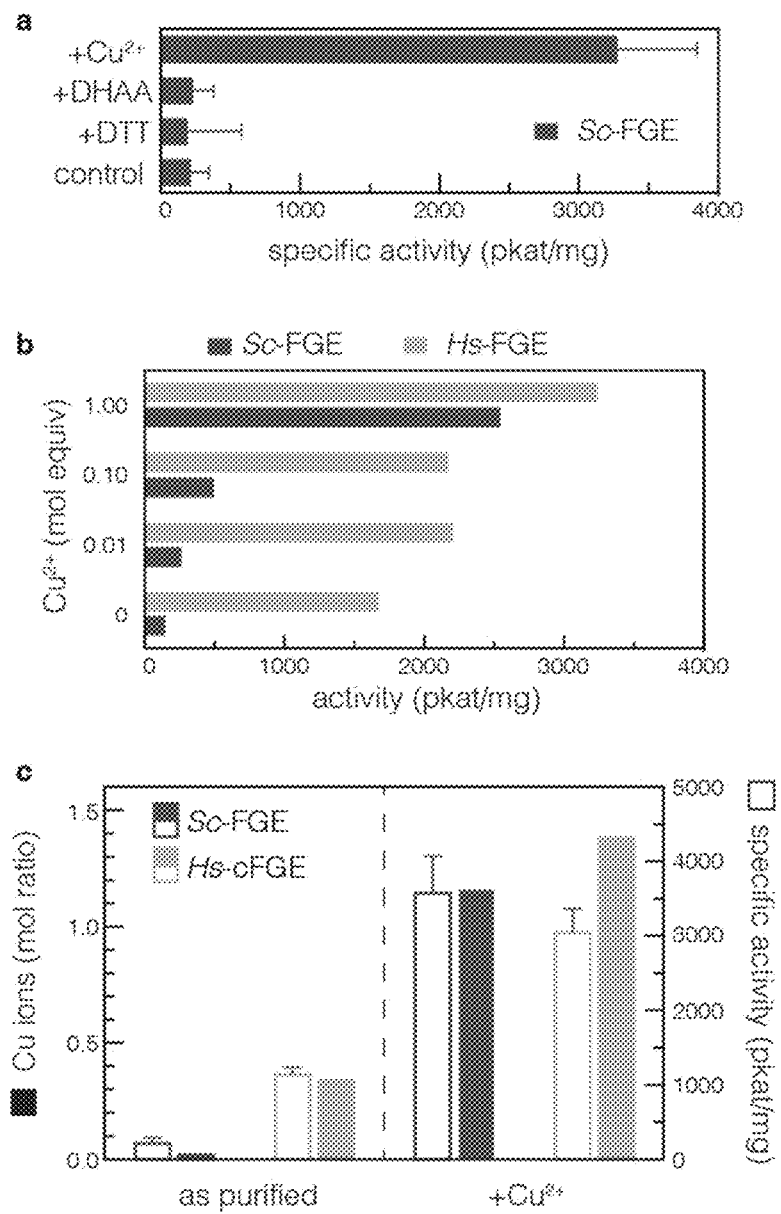
FIG. 15 show data indicating that the specific activity of FGE increased significantly upon treatment with stoichiometric amounts of copper(II).

Formation of the reduced active site Cys residues was accomplished by pretreatment of Sc-FGE with an excess (100 molar equiv) of a strong reducing agent (DTT) for 1 h at 25° C., after which the reagent was removed by gel filtration. Formation of the oxidized active site was accomplished by pretreatment of the enzyme either with an excess (100 molar equiv) of (L)-dehydroascorbic acid (DHAA) or CuSO$_4$ for 1 h at 25° C., followed by removal of the reagents by gel filtration. DHAA can form disulfides stoichiometrically, and Cu$^{2+}$ can rapidly, and cleanly, catalyze disulfide formation with dissolved oxygen. After these treatments, the specific activities of each enzyme were measured using the standard kinetic assay. Only pretreatment with CuSO$_4$ resulted in any significant change in activity (FIG. 15, panel a).

Since pretreatment and removal of copper led to more active FGE, experiments were performed to investigate the quantity of copper that could activate Sc-FGE. Treatment of FGE with 1, 10, or 100 mol % CuSO$_4$ demonstrated that stoichiometric amounts of copper generated a highly active enzyme (FIG. 15, panel b). Amounts less than 1 molar equiv resulted in proportionally lower activity, an observation that is inconsistent with the catalytic activation of active site thiols.

Experiments were performed to determine whether it is possible to enhance the FGE reaction rate by adding copper directly to the reaction mixture. The data confirmed that product formation was significantly inhibited by the inclusion of copper in the reaction (FIG. 12, panel c). Rapid formation of the oxidized form of DTT (FIG. 12, panel d) as well as $C_{sub}$-$C_{sub}$ (FIG. 12, panel e) as a result of copper-catalyzed disulfide formation was observed.

Both Sc-FGE and Hs-cFGE could be efficiently activated with 5 molar equiv of $CuSO_4$ for 1 h at 25° C. followed by removal of excess copper. The specific activity of Sc-FGE increased by more than an order of magnitude—from 214±34 pkat·mg$^{-1}$ to 3579±215 pkat·mg$^{-1}$; Hs-cFGE specific activity increased by a factor of 3, from 1,143±84 pkat·mg$^{-1}$ to 3,050±115 pkat·mg$^{-1}$ (FIG. 15, panel c). Experiments were performed to determine whether FGE that was treated with copper contained the metal after purification. The quantities of copper in both the unactivated and the activated FGE samples were measured using ICP-MS. The Sc-FGE produced in *E. coli* contained almost no copper above the level of the noise of the measurement. By contrast, Hs-cFGE—as isolated from insect cells—contained 0.35 mol Cu per mol FGE. Both of the copper treated "activated" forms of FGE contained just above 1 mol Cu/FGE. Furthermore, the specific activity of each of these enzyme preparations correlated with the ratio of Cu/FGE, indicating that copper is an integral component of the active form of FGE (FIG. 15, panel c).

It was then considered whether it is possible to enhance the FGE reaction rate by adding copper directly to the reaction mixture. The data indicated that product formation was significantly inhibited by the inclusion of copper in the reaction. Specifically, very rapid formation of the oxidized form of DTT as well as $C_{sub}$-$C_{sub}$ was observed as a result of copper-catalyzed disulfide formation (FIG. 15, panel d). The vertical bars from left to right for each of fGly, $C_{sub}$-$C_{sub}$ and $DTT_{OX}$ correspond to $Cu^{2+}$ concentrations of 0 μM, 5 μM and 50 μM.

To confirm that catalytic activity in the activated form of FGE did not depend upon an active site disulfide, experiments were performed to determine whether addition of strong reducing agents to the activated enzyme would decrease the specific activity of the resulting material. If the integrity of the active site disulfide was important for turnover, then strong reducing agents should have decreased FGE turnover rates.

Figure 16:
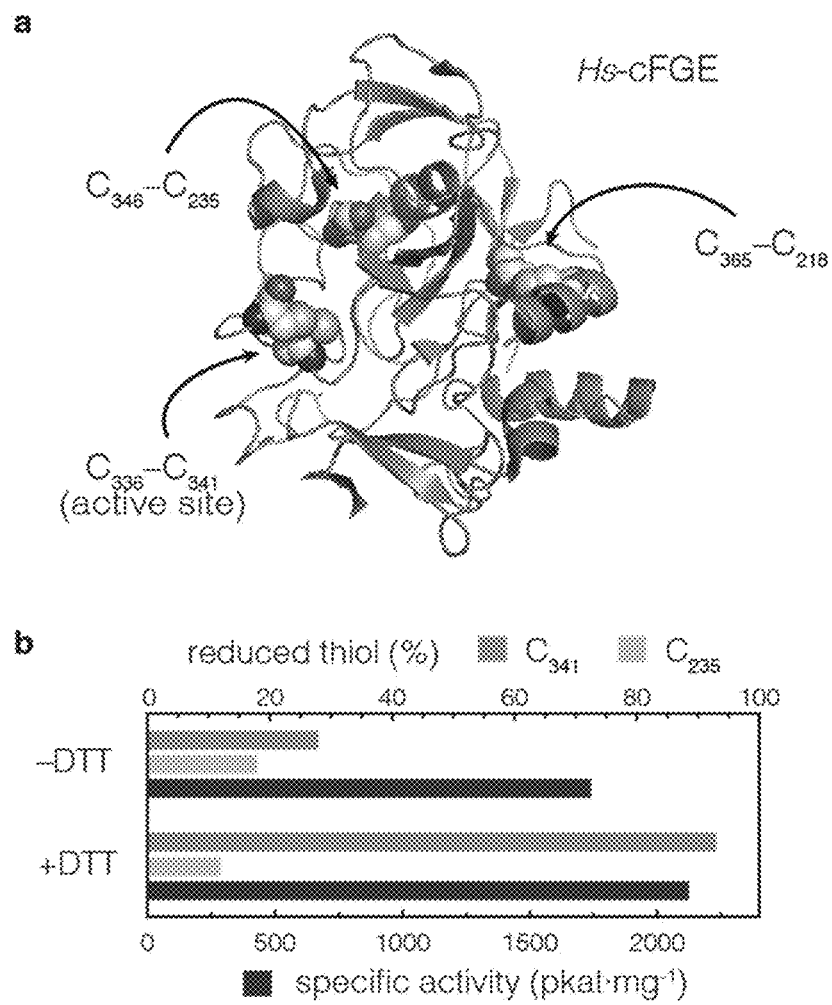
FIG. 16 shows data indicating that specific activity of Hs-cFGE did not correlate with the redox state of active site residue $C_{341}$.

Hs-cFGE may form the active site disulfide ($C_{336}$-$C_{341}$) as well as two structural disulfides ($C_{346}$-$C_{235}$ and $C_{365}$-$C_{218}$) elsewhere in the protein (FIG. 16, panel a). Treatment of Hs-cFGE with 20 mM DTT (or 20 mM TCEP, not shown) produced an FGE with unchanged specific activity (FIG. 16, panel b). To confirm that the relevant Cys residues changed redox state as a result of this treatment, an LC-MRM/MS assay was used to detect solution-accessible Cys residues in the active site. With this method, both the $C_{341}$- and $C_{235}$-containing peptides were monitored. Treatment with DTT increased the proportion of accessible active site $C_{341}$ from 28% to 93%. $C_{235}$, which participated in a buried structural disulfide, was inaccessible (and thus, in a disulfide) independent of DTT treatment. Taken together, these data confirmed that reductive treatment generated almost quantitatively reduced active site thiols, did not perturb other structural disulfides, but had no effect on the catalytic activity of FGE.

Figure 17:
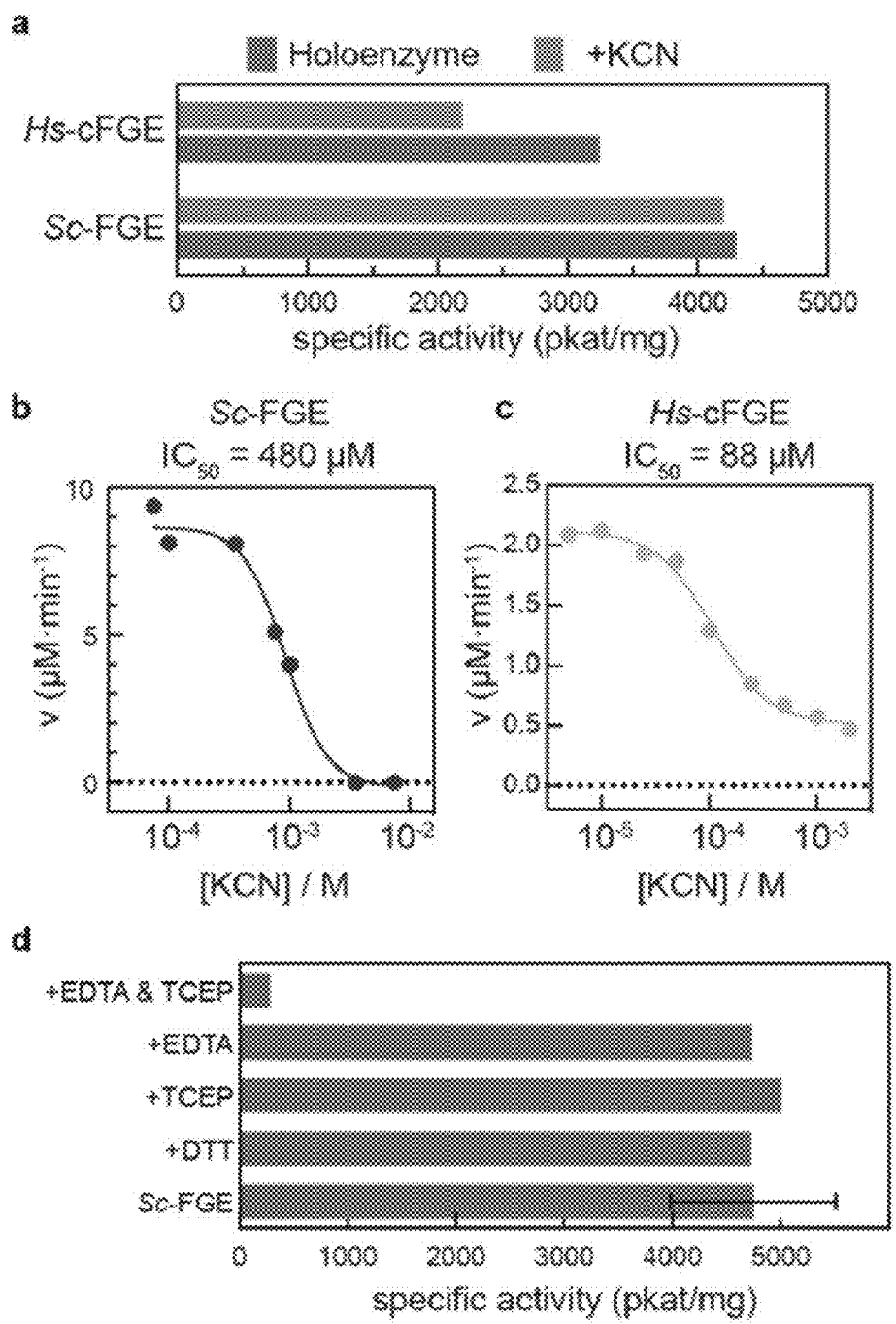
FIG. 17 shows data indicating that FGE catalysis was inhibited by cyanide.

After observing that FGE contained ~1 copper atom per enzyme, experiments were performed to remove the metal in order to determine whether it was required for catalytic activity. Attempts to remove copper through the addition of 5 molar equiv EDTA did not change the catalytic activity of copper-treated Sc-FGE or Hs-cFGE (FIG. 17, panel a). KCN, however, did decrease the activity of Hs-cFGE by a modest amount, suggesting that it could gain access to the bound copper. Since pretreatment with KCN slightly decreased the activity of Hs-cFGE, experiments were performed to test whether FGE turnover could be inhibited by inclusion of KCN in the reaction mixture. As shown in FIG. 17, panel b, a concentration-dependent inhibition of activity on both Sc-FGE ($IC_{50}$=480 μM) and Hs-cFGE (88 μM) was observed. In the case of copper amine oxidases, apoenzyme has been generated by extracting copper with KCN from enzyme that was pre-reduced with sodium dithionate. In a similar manner, this approach was also successful for FGE. Activity decreased significantly upon treatment (1 h, 37° C.) with both a reductant and chelator (15 mM TCEP and EDTA), but not with each component individually (FIG. 17, panel d).

Figure 18:
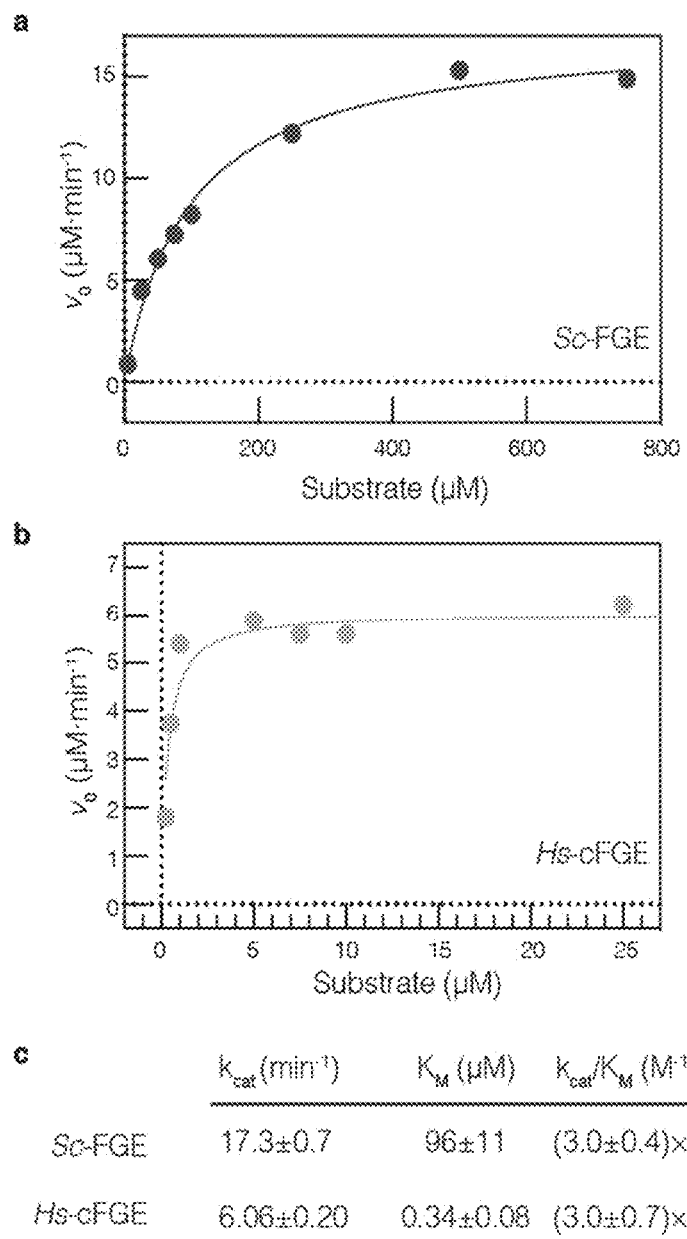
FIG. 18 shows data of kinetic parameters of Sc-FGE and Hs-cFGE as determined by nonlinear regression.

Experiments were performed to determine the standard enzymatic parameters of both Sc-FGE and Hs-cFGE (FIG. 18). They differed significantly between the two species. Sc-FGE did not interact with substrate very strongly ($K_M$=96 μM) and exhibited a relatively rapid $k_{cat}$ (17.3 min$^{-1}$), which together resulted in a modest enzyme efficiency with $k_{cat}/K_M$=3.0×10$^4$ M$^{-1}$·s$^{-1}$ (FIG. 18, panel 1). By comparison, Hs-cFGE turned over substrate with a slower catalytic rate constant ($k_{cat}$=6.06 min$^{-1}$) but demonstrated a strong interaction with the substrate peptide ($K_M$=0.34 μM). Taken together, the Hs-cFGE ($k_{cat}/K_m$=3.0×10$^6$ M$^{-1}$·s$^{-1}$) was approximately 10-fold more efficient than its bacterial counterpart (FIG. 18, panel b).

The data demonstrated that the modestly active forms of FGE isolated from cell culture were a mixture of the apoenzyme, lacking the copper cofactor, and the holoenzyme, which was highly active and efficiently converted Cys to fGly on peptide substrates. Experiments were performed to develop conditions for using the FGE holoenzyme in biocatalytic reactions on folded protein substrates.

FGE was an efficient biocatalyst for in vitro conversion of Cys to fGly on folded proteins. In order to use in vitro conversion for the production of aldehyde-tagged mAbs, the following reaction conditions were tested. For most substrates, 5-10 molar equiv of DTT was sufficient to achieve complete conversion. Turnover was also possible with tris (carboxyethyl) phosphine (TCEP), lipoic acid, and bis(2-mercaptoethyl)sulfone (BMS). However, the presence of even 1 molar equiv of a strong reducing agent (e.g., DTT, TCEP, lipoic acid, or BMS) could cleave disulfides that were present in a mAb substrate. To avoid substrate disulfide cleavage, an alternate reducing agent was used for the reaction. Weaker reducing agents—e.g., βME or GSH—were tolerated by antibody substrates, and also enabled FGE catalysis. However, changing from a cyclizing (DTT) to a non-cyclizing reducing agent (βME) resulted in side products that had not previously been observed (discussed below). In order to reduce side product formation and increase product yield, experiments were performed to determine the role(s) of the reducing agent in enzymatic turnover.

X-ray crystallography of FGE (apoenzyme) bound to a substrate peptide showed $C_{341}$ and $C_{sub}$ covalently linked by a disulfide in the active site. If the substrate was anchored by this $C_{341}$-$C_{sub}$ disulfide during turnover, an exogenous thiol might be able to react with the enzyme-substrate complex (E•S) by thiol-disulfide exchange to release substrate in the form of a thiol-$C_{sub}$ disulfide. Two off-pathway products were formed by FGE during turnover. First, when reducing agent was not added to the reaction, $C_{sub}$-$C_{sub}$ dimer formation was observed. Second, when a monothiol was added as the reductant (e.g., βME), rapid production of the $C_{sub}$-βME disulfide was observed (FIG. 13, panel a). In control reactions lacking enzyme, neither $C_{sub}$-$C_{sub}$ nor $C_{sub}$-βME were generated.

Figure 19:
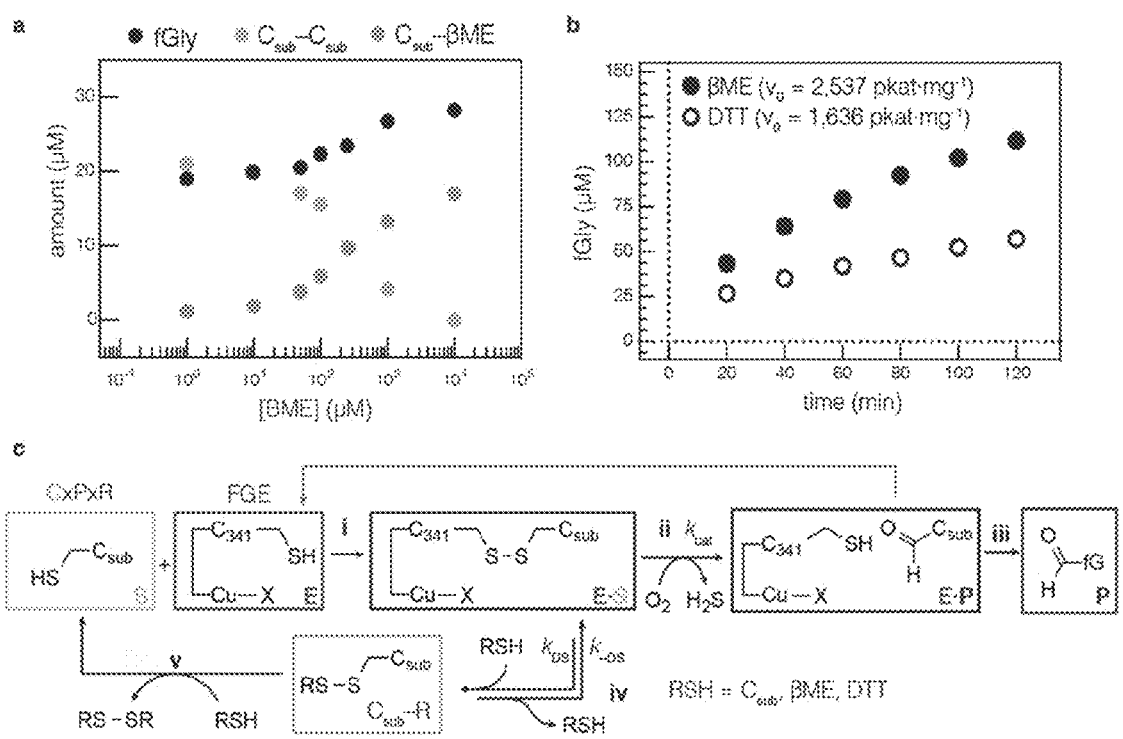
FIG. 19 shows data indicating that FGE can catalyze substrate/reductant disulfide formation, which can be inhibitory to product yield, and confirms that substrate was bound in the active site as a disulfide.

The formation of $C_{sub}$-$C_{sub}$ and $C_{sub}$-βME was monitored as a function of reaction conditions. First, the concentration of reducing agent in the reaction was varied, and the reactions were quenched when they were half complete. At low [βME] v. [$C_{sub}$], the $C_{sub}$-$C_{sub}$ predominated (FIG. 19, panel a). Increasing [βME] resulted in a concurrent decrease in $C_{sub}$-$C_{sub}$, and an increase in $C_{sub}$-βME. Increasing [βME] also resulted in a higher yield of fGly.

Experiments were performed to determine the effect of [βME] as the reaction evolved over time (FIG. 13, panel b). As described above, in the absence of exogenous reducing agent product did form, but a significant proportion of $C_{sub}$-$C_{sub}$ was generated (FIG. 13, panel c), indicating that $C_{sub}$ can act in place of the reducing agent during turnover, but at the expense of product yield. At low [βME] (0.25 mM, 2.5 molar equiv vs. $C_{sub}$), the $C_{sub}$-$C_{sub}$ initially grew in at a rate competitive with product formation (FIG. 13, panel d), but as the reaction proceeded, it reached a maximum, and then decayed away slowly. At this [βME], the $C_{sub}$-$C_{sub}$ was consumed, the $C_{sub}$-βME rapidly reached a plateau of 13% of total peptide, where it remained. In a subsequent reaction with higher [βME] (10 mM), the consumption of $C_{sub}$-$C_{sub}$ was more rapid (FIG. 13, panel e). In addition, while $C_{sub}$-βME quickly rose to 10% of the total substrate, it also decayed rapidly, in contrast to lower [βME]. In all cases, the consumption of both $C_{sub}$-$C_{sub}$ and $C_{sub}$-βME correlated with a higher yield of product formation. Since disulfide production during turnover was competitive with product formation, and did not occur in the absence of enzyme, these data confirmed that disulfide formation between FGE and substrate was part of the FGE catalytic cycle.

In contrast to βME, when DTT was used as the stoichiometric reductant neither the intermediate $C_{sub}$-$C_{sub}$ nor the $C_{sub}$-DTT disulfides were observed. This was likely because DTT can cyclize to form an intramolecular disulfide and release substrate. However, the rates of product formation in reaction using βME or DTT were not the same (FIG. 19, panel b). Specifically, the rates of product formation were 5.07 or 3.27 $min^{-1}$ in the presence of βME or DTT, respectively. Since reducing agent was present in large excess versus both the substrate and enzyme, it may be involved in limiting the rate of turnover.

If the reductants were acting by a one-electron mechanism, their relative reaction rates should depend directly upon their reduction potentials:

$E_0'$(βME)=−207 mV and $E_0'$(DTT)=−323 mV. If instead, the reductants were acting by thiol-disulfide exchange, their reaction rate should correlate with their thiol-disulfide exchange rate constants: $k_{\beta ME}=1$ and $k_{DTT}=6\times10^5$, as measured versus glutathione disulfide. Both of these scenarios predict that reactions performed in the presence of DTT should have a faster rate than those performed in the presence of βME. By contrast, reactions performed with DTT were slower than those with βME, and so the role of the thiol in the reaction may not depend on the reaction rate of the thiol alone.

The covalent disulfide in E•S that was confirmed by the experiments above may be the source of the difference in reaction rates described above (FIG. 19, panel c). From this state, E•S can either proceed to product with a rate constant of $k_{cat}$, or it can react with an exogenous thiol by thiol-disulfide exchange with a rate constant of $k_{DS}$. For any given reducing agent, $k_{cat}$ is likely the same based upon the mechanisms of analogous copper-dependent oxidases, in which substrate release, and not redox chemistry, is rate limiting. However, $k_{DS}$ may depend directly upon the identity of the reducing agent in solution and its thiol-disulfide reaction rate constant. Said another way, E•S should dissociate faster in the presence of a stronger reducing agent, in competition with product formation. In addition, if the substrate was released as a disulfide that does not decay quickly (as with βME-DS), it could react with the enzyme again to regenerate E•S. Therefore, stronger reductants should slow turnover by dissociating the E•S complex. This aspect of the cycle may also explain the faster turnover rate observed at pH 9 relative to pH 7; thiol-disulfide exchange was faster under basic conditions.

Figure 20:
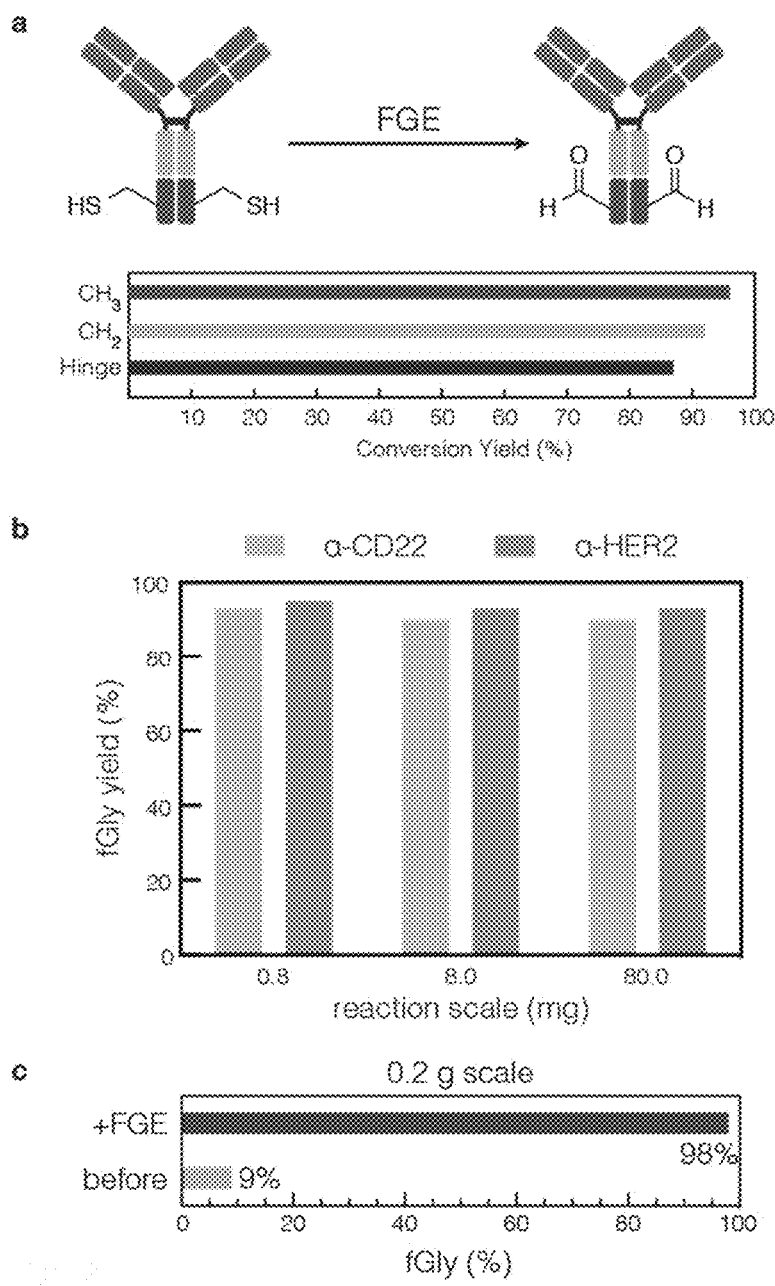
FIG. 20 shows data indicating that FGE can be used to produce aldehyde tagged mAbs in high yield.
Figure 21:
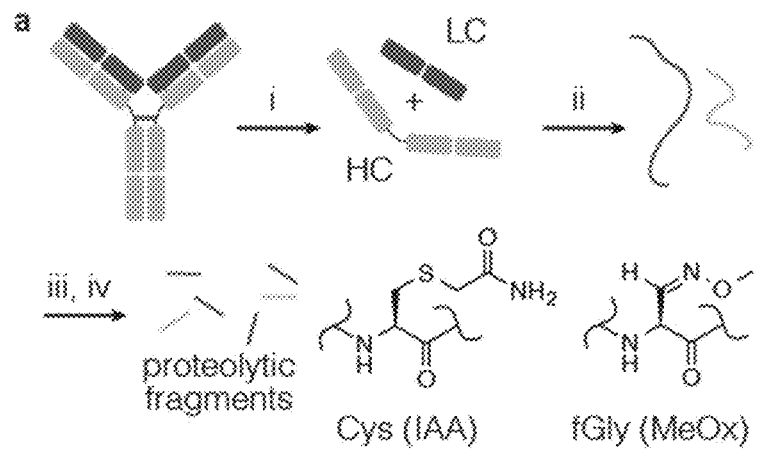
FIG. 21 shows data related to LC-MRM/MS characterization of Cys- and fGly-containing proteins.
Figure 21:
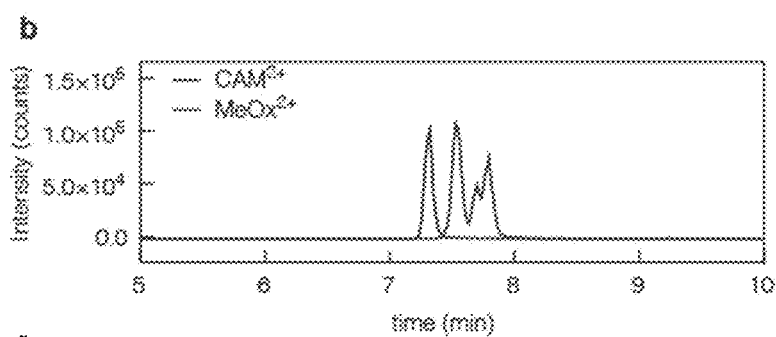
Figure 21:
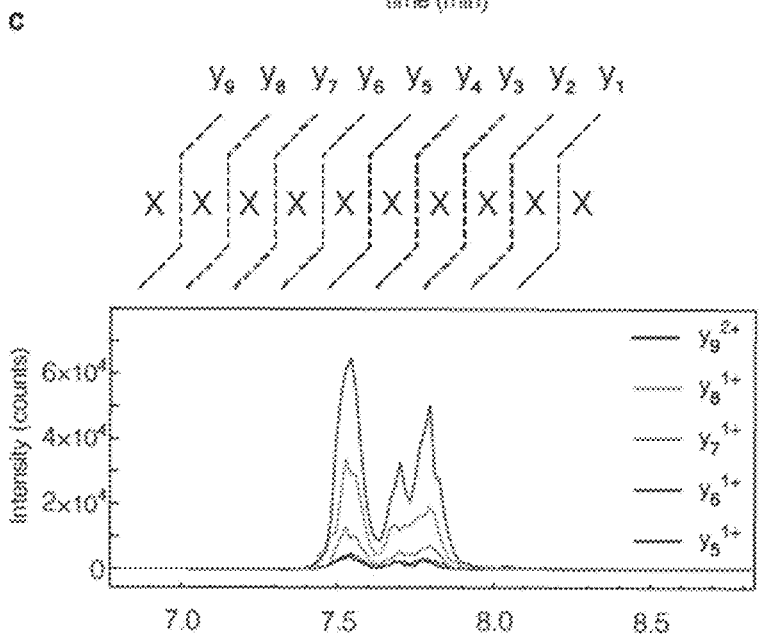
Figure 22:
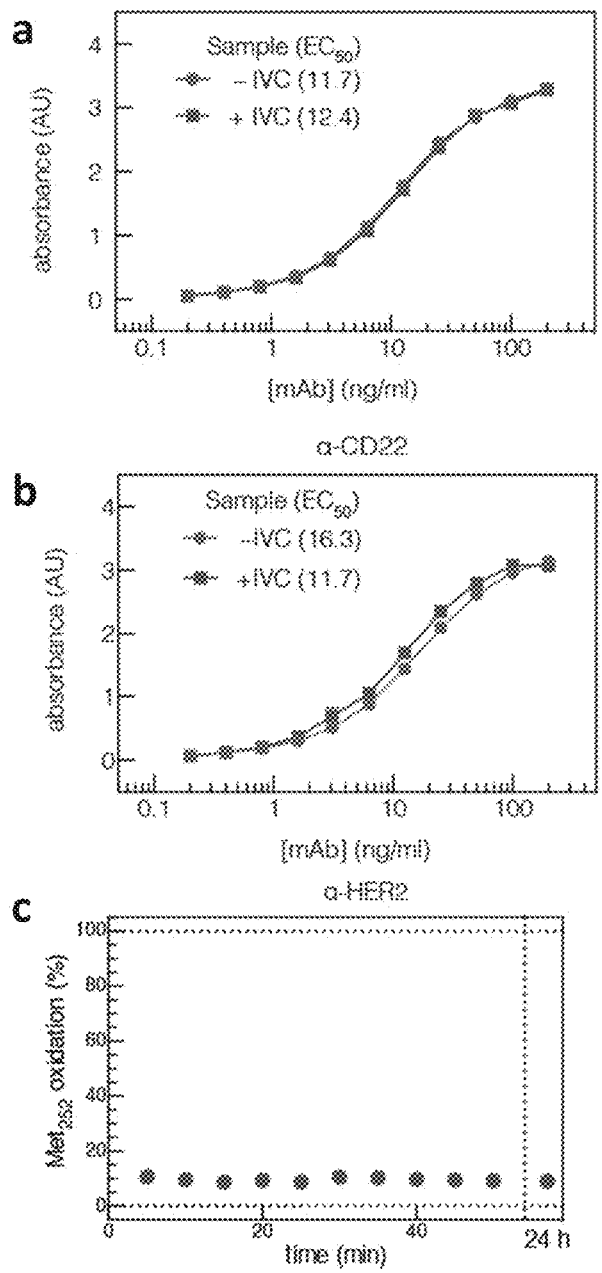
FIG. 22 shows data related to the biophysical properties of mAbs subjected to in vitro conversion reaction conditions.

The aldehyde tag can be introduced at the N- or C-terminus or at any solvent accessible internal sequence. Here, Cys was converted to fGly in high yield by Hs-cFGE in three independent regions of a mAb (FIG. 20, panel a) and across a wide range of reaction scales (from 0.8-200 mg) on three independent mAbs (FIG. 20, panel b, and FIG. 20, panel c). In each case, the in vitro conversion yield was >90%, as measured by LC-MRM/MS (FIG. 21). Furthermore, the pH 9 reaction conditions did not affect antigen binding affinity (FIG. 22, panel a, and FIG. 22, panel b) or oxidation at Met252 (FIG. 22, panel c), a residue that is important for FcRn binding and mAb circulation in vivo.

DISCUSSION

Methods for recombinant production of both Sc-FGE and Hs-cFGE in good yield are described herein. In addition, a discontinuous HPLC assay to measure the kinetic parameters of both FGEs is described. These results indicated that the N-terminal extension of Hs-FGE was not required for catalytic activity in vitro. As isolated from insect cell culture, the human enzyme was significantly more active than the bacterial form of FGE from S. coelicolor as produced in E. coli.

Experiments were performed to determine the mechanism of FGE turnover. The existing mechanistic hypotheses focus on the redox state of the FGE active site cysteine residues as revealed by crystallography. When Hs-cFGE was isolated previously, $C_{336}$ ($C_{272}$ in Sc-FGE) and $C_{341}$ ($C_{277}$) were present in the enzyme in a mixture of reduced and oxidized forms. The oxidation state of $C_{336}$ and $C_{341}$ can be manipulated using chemical reagents in solution, either to form the $C_{336}$-$C_{341}$ disulfide, or with $H_2O_2$ over a longer period of time, to form a sulfonic acid at both positions. In addition, a $C_{336}$S mutation enabled the "trapping" of $C_{sub}$ as an intermolecular disulfide with $C_{341}$. This indicated that FGE uses a thiol-disulfide interchange to anchor $C_{sub}$ and activate $C_{336}$. This residue may then perform the activation of molecular oxygen to form a higher oxidation state Cys residue (either sulfenic acid or cysteine peroxide) and subsequently oxidize the substrate.

FGE was able to catalyze the formation of disulfides at the substrate Cys when monothiol reducing agents were present in solution. This indicated that FGE bound $C_{sub}$ in a disulfide, and that when $k_{cat}$ was slower than the rate of reaction with reducing agent in solution, $C_{sub}$ can be released as a disulfide. When dithiol reagents such as DTT were used, any intermolecular disulfide was quickly abolished by DTT cyclization.

FGE incorporates copper as a cofactor for catalysis. The results indicated that recombinant expression of FGE most often resulted in the apoenzyme, which can be reconstituted as the holoenzyme by the addition of copper(II) sulfate at pH 7. The catalytic rates of both human and bacterial FGE were significantly increased upon activation with stoichiometric amounts of $Cu^{2+}$, and turnover was inhibited by the addition of cyanide to FGE reaction mixtures.

The data indicated that FGE may be a copper oxidase that performs $2 H^+/2 e^-$ oxidation, activates molecular oxygen, and requires exogenous reductants to complete a catalytic cycle.

Figure 23:
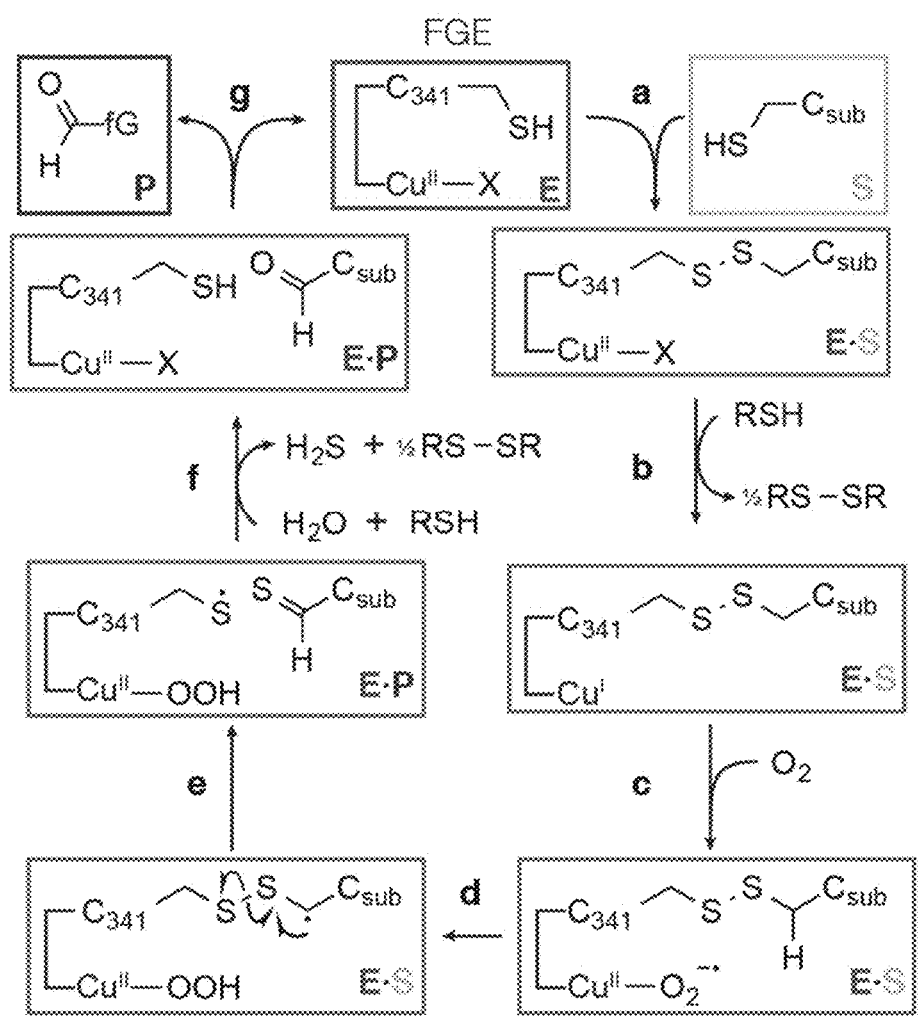
FIG. 23 shows a schematic of the proposed catalytic mechanism for FGE that accounts for the copper cofactor. As shown in step a, substrate S binds enzyme E and is covalently attached through $C_{341}$. This covalent bond formation may be catalyzed by $Cu^{2+}$, or it could result from thiol-disulfide exchange between an existing $C_{341}$ disulfide and substrate. As shown in step b, reduction of $Cu^{2+}$ to $Cu^{1+}$ would enable binding of molecular oxygen (step c), as the $Cu^{2+}$ superoxo intermediate. As shown in step d, oxidation of substrate by the $Cu(II)$-$O_2^-$ through proton-coupled electron transfer (likely hydrogen atom transfer) would generate a disulfide radical, which would rapidly collapse, (step e), to thioaldehyde and thiyl radical. A second 1 $H^+$/1 $e^-$ reduction and hydrolysis would regenerate $C_{341}$. The way in which this reduction occurs could proceed through a number of pathways, including, but not limited to: direct thiyl radical reduction and hydrolysis of copper-peroxide to release $H_2O_2$; or oxo transfer from $Cu(II)$-OOH to the radical to generate a sulfenic acid, followed by copper-oxyl reduction and sulfenic acid hydrolysis.

From the data described above, the formation of side products indicated that the [E•S] complex involved a covalent disulfide bridge (FIG. 23, step a). Reducing agent would serve to generate the Cu(I) state of the active site (FIG. 23, step b), which is an intermediate for binding of molecular oxygen (FIG. 23, step c) as the cupric superoxo $Cu(II)-O_2^-$ that is poised for substrate oxidation. The substrate cysteine sidechain could then react by proton-coupled electron transfer, most likely in the form of hydrogen atom transfer (FIG. 23, step d). After oxidation, the disulfide radical may collapse to the thioaldehyde and a thiyl radical (FIG. 23, step e). The second equivalent of $1 H^+/1 e^-$ would regenerate the active site Cys, and the thioaldehyde would rapidly hydrolyze to the product fGly (FIG. 23, step f and step g). Formally the oxidation reaction would be complete simply by displacing $H_2O_2$ as a reaction product, but the cupric peroxide Cu(II)-OOH might also undergo further reduction to generate only $H_2O$ as a byproduct. At this point, the resting state ligand on copper may be a hydroxide, although direct involvement of $C_{341}$ through an alternative mechanism may be possible.

As described above, reaction conditions were developed for efficient production of fGly without disrupting existing intramolecular disulfides in the substrate protein. FGE was produced in good yield and used as a biocatalyst for the production of aldehyde-tagged proteins in vitro. Reactions with FGE scaled across at least three orders of magnitude in mass with no significant decrease in yield, and proceeded without perturbing existing disulfides or modifying residues that were important for mAb performance in vivo.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of producing a protein comprising a formylglycine residue, the method comprising:
   expressing a combining an activated formylglycine-generating enzyme (FGE) and a protein comprising an FGE recognition site in a cell-free reaction mixture comprising $Cu^{2+}$ to activate the FGE, under conditions in which the activated FGE converts a cysteine residue or a serine residue of the FGE recognition site to a formylglycine residue, to produce a protein comprising a formylglycine residue.

2. The method according to claim 1, wherein the activated FGE and the protein comprising the FGE recognition site are combined in a reaction mixture comprising a reducing agent.

3. The method according to claim 2, wherein the reducing agent promotes conversion of the cysteine residue or the serine residue of the FGE recognition site to the formylglycine residue.

4. The method according to claim 3, wherein the reducing agent is 2-mercaptoethanol.

5. The method according to claim 1, wherein the $Cu^{2+}$ is provided by a source of $Cu^{2+}$ selected from copper sulfate, copper citrate, copper tartrate, Fehling's reagent, and Benedict's reagent.

6. The method according to claim 1, wherein the source of $Cu^{2+}$ is copper sulfate.

7. The method according to claim 1, wherein the FGE is an N-terminally truncated FGE.

8. The method according to claim 7, wherein the FGE is a N-terminally truncated human FGE.

9. The method according to claim 1, wherein the protein is an antibody, an antibody fragment, a ligand, an enzyme, or an antigen.

10. The method according to claim 1, wherein the protein is an antibody or antibody fragment.

11. The method according to claim 10, wherein the antibody or antibody fragment is selected from the group consisting of: an IgG or fragment thereof, a Fab, a F(ab')2, a Fab', an Fv, an ScFv, a bispecific antibody or fragment thereof, a diabody or fragment thereof, a chimeric antibody or fragment thereof, a monoclonal antibody or fragment thereof, a humanized antibody or fragment thereof, and a fully human antibody or fragment thereof.

12. The method according to claim 10, wherein the antibody specifically binds to a tumor-associated antigen or a tumor-specific antigen.

13. The method according to claim 12, wherein the tumor associated antigen or tumor-specific antigen is selected from the group consisting of: HER2, CD19, CD22, CD30, CD33, CD56, CD66/CEACAM5, CD70, CD74, CD79b, CD138, Nectin-4, Mesothelin, Transmembrane glycoprotein NMB (GPNMB), Prostate-Specific Membrane Antigen (PSMA), SLC44A4, CA6, and CA-IX.

14. The method according to claim 1, wherein the protein is a ligand.

15. The method according to claim 14, wherein the ligand is a growth factor.

16. The method according to claim 14, wherein the ligand is a hormone.

* * * * *

UNITED STATES PATENT AND TRADEMARK OFFICE
CERTIFICATE OF CORRECTION

PATENT NO. : 9,951,367 B2
APPLICATION NO. : 14/975403
DATED : April 24, 2018
INVENTOR(S) : David Rabuka et al.

Page 1 of 1

It is certified that error appears in the above-identified patent and that said Letters Patent is hereby corrected as shown below:

In the Claims

At Column 57, Line 57, "expressing a combining an activated formylglycine-gen-" should read
-- expressing a formylglycine-gen- --

Signed and Sealed this
Fourth Day of December, 2018

Andrei Iancu
*Director of the United States Patent and Trademark Office*